US012629282B1

(12) United States Patent
Zaun et al.

(10) Patent No.: US 12,629,282 B1
(45) Date of Patent: May 19, 2026

(54) METHOD AND EYEWEAR APPARATUS FOR LOWER VISUAL FIELD OBSTRUCTION

(71) Applicants: Drew Richard Zaun, Des Moines, IA (US); Thomas Raymond Goetz, West Des Moines, IA (US)

(72) Inventors: Drew Richard Zaun, Des Moines, IA (US); Thomas Raymond Goetz, West Des Moines, IA (US)

( * ) Notice: Subject to any disclaimer, the term of this patent is extended or adjusted under 35 U.S.C. 154(b) by 0 days.

(21) Appl. No.: 19/288,464

(22) Filed: Aug. 1, 2025

Related U.S. Application Data

(60) Provisional application No. 63/678,722, filed on Aug. 2, 2024.

(51) Int. Cl.
A61F 9/04 (2006.01)
A61M 21/00 (2006.01)
(Continued)

(52) U.S. Cl.
CPC ............... A61F 9/04 (2013.01); A61M 21/00 (2013.01); A61B 10/0041 (2013.01); A61B 10/0233 (2013.01); A61M 2021/0044 (2013.01)

(58) Field of Classification Search
CPC ................. A61F 9/04–045; G02C 7/16; G02C 5/001–003
See application file for complete search history.

(56) References Cited

U.S. PATENT DOCUMENTS

| | | | |
|---|---|---|---|
| 4,022,466 A | 5/1977 | Kaiser | |
| 4,963,013 A | 10/1990 | Bononi | |

(Continued)

FOREIGN PATENT DOCUMENTS

| | | | |
|---|---|---|---|
| CN | 201886220 U | * | 6/2011 |
| CN | 211583173 U | * | 9/2020 |

(Continued)

*Primary Examiner* — Thaddeus B Cox
(74) *Attorney, Agent, or Firm* — McKee, Voorhees & Sease, PLC

(57) ABSTRACT

A method and eyewear apparatus for reducing visual triggers during vascular access or interventional procedures or other medical procedures or treatments. One method uses a vision-restricting eyewear apparatus comprising a lens with an opaque lower region and an affixed compressible foam pad that together obstruct the subject's lower field of vision while preserving partial forward or upward visibility. When worn, the apparatus forms at least a substantially continuous, gapless visual barrier that limits exposure to procedural stimuli for effective blocking. The method and apparatus aim to reduce physiological and psychological distress, including vasovagal responses. In one non-limiting embodiment, a vision-restricting apparatus and associated method are provided for reducing visual triggers during vascular access, breast biopsy, or other interventional procedures. The apparatus includes a lens or eyeshield having an opaque lower region configured to obstruct the user's inferior visual field while preserving forward or upward visibility through a transparent upper region. Affixed along the lower edge of the lens is a compressible, skin-safe foam or other interface that deforms by folding or bending against itself, forming a continuous, gapless visual barrier that conforms to a variety of facial anatomies. In some embodiments, the apparatus comprises a single continuous lens or eyeshield body or discrete lenses for each eye, and may further include a support frame or adhesive interface for facial adhesive of the apparatus to a patient. The method comprises applying the apparatus immediately prior to a needle-based or image-guided procedure to position the visual obstruction in place, thereby reducing physiological or psychological distress— such as vasovagal responses—by blocking distress-inducing stimuli within the lower visual field. The apparatus is suitable for single-use disposable application.

25 Claims, 36 Drawing Sheets

(Continued)

(11 of 36 Drawing Sheet(s) Filed in Color)

(51) Int. Cl.
    *A61B 10/00*         (2006.01)
    *A61B 10/02*         (2006.01)

(56)                References Cited

U.S. PATENT DOCUMENTS

| | | | |
|---|---|---|---|
| 5,394,567 | A | 3/1995 | Vatterott |
| 5,543,864 | A | 8/1996 | Hirschman et al. |
| D623,683 | S | 9/2010 | Rohrbach |
| 9,300,949 | B2 | 3/2016 | Ahearn |
| 9,709,828 | B2 | 7/2017 | Farris |
| 10,126,570 | B2 | 11/2018 | Sotto, II |
| D870,171 | S | 12/2019 | Chae |
| 2002/0174872 | A1* | 11/2002 | Cyphers ................ A61M 25/02 |
| | | | 128/888 |
| 2004/0161730 | A1 | 8/2004 | Urman |
| 2005/0146674 | A1 | 7/2005 | Foulke et al. |
| 2007/0132943 | A1 | 6/2007 | Kurzrok |
| 2009/0262299 | A1 | 10/2009 | Viktor |
| 2016/0089272 | A1 | 3/2016 | Li et al. |
| 2017/0097522 | A1 | 4/2017 | Parks |
| 2018/0059438 | A1 | 3/2018 | Rao |
| 2020/0008687 | A1* | 1/2020 | Friedlander ............. A61B 3/16 |

FOREIGN PATENT DOCUMENTS

| | | | | |
|---|---|---|---|---|
| CN | 219921060 | U | * 10/2023 | |
| CN | 118806277 | A | * 10/2024 | ........... A61M 21/00 |
| EP | 3940451 | A1 | 1/2022 | |
| FR | 3110714 | A1 | 11/2021 | |
| WO | WO-2024086527 | A1 | * 4/2024 | ............. G06F 3/013 |

\* cited by examiner

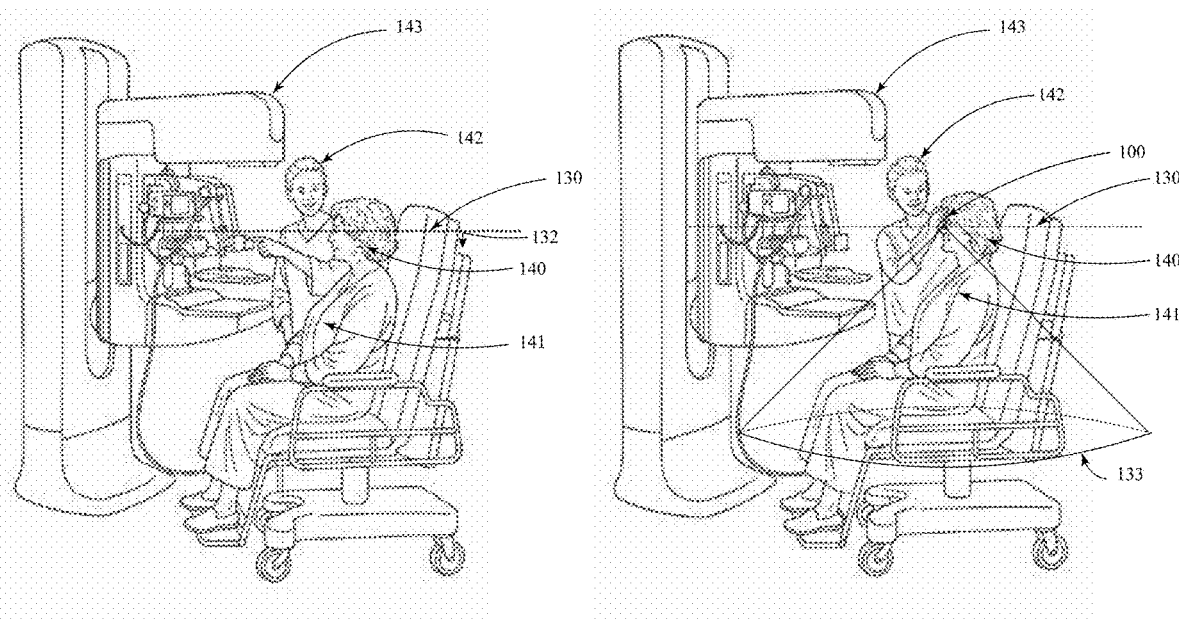
Figure 1 - Baseline Procedure Setup
Figure 2 - Application of Eyewear Apparatus
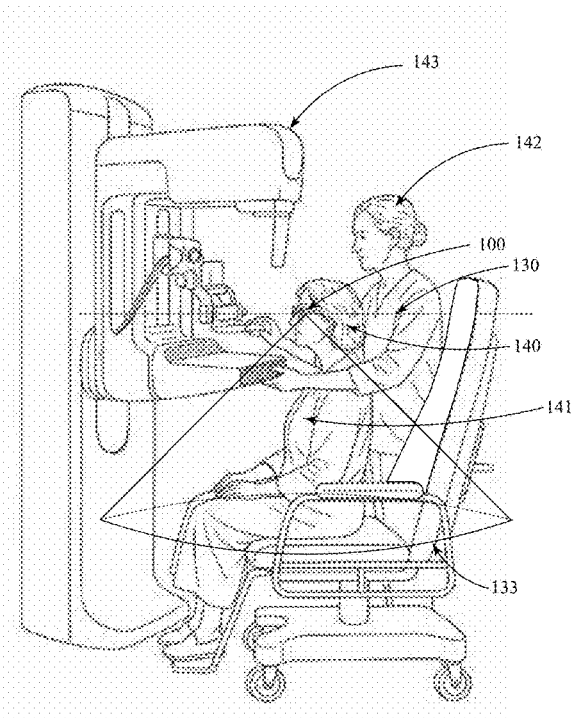
Figure 3 – Procedure Performed with Eyewear in Place

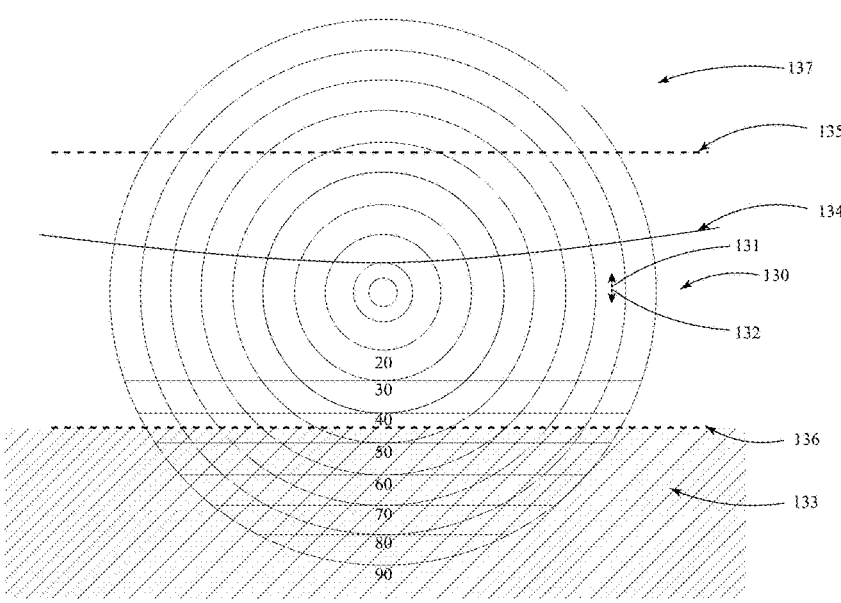
Figure 4 – Goldmann Visual Field Obstruction Limits
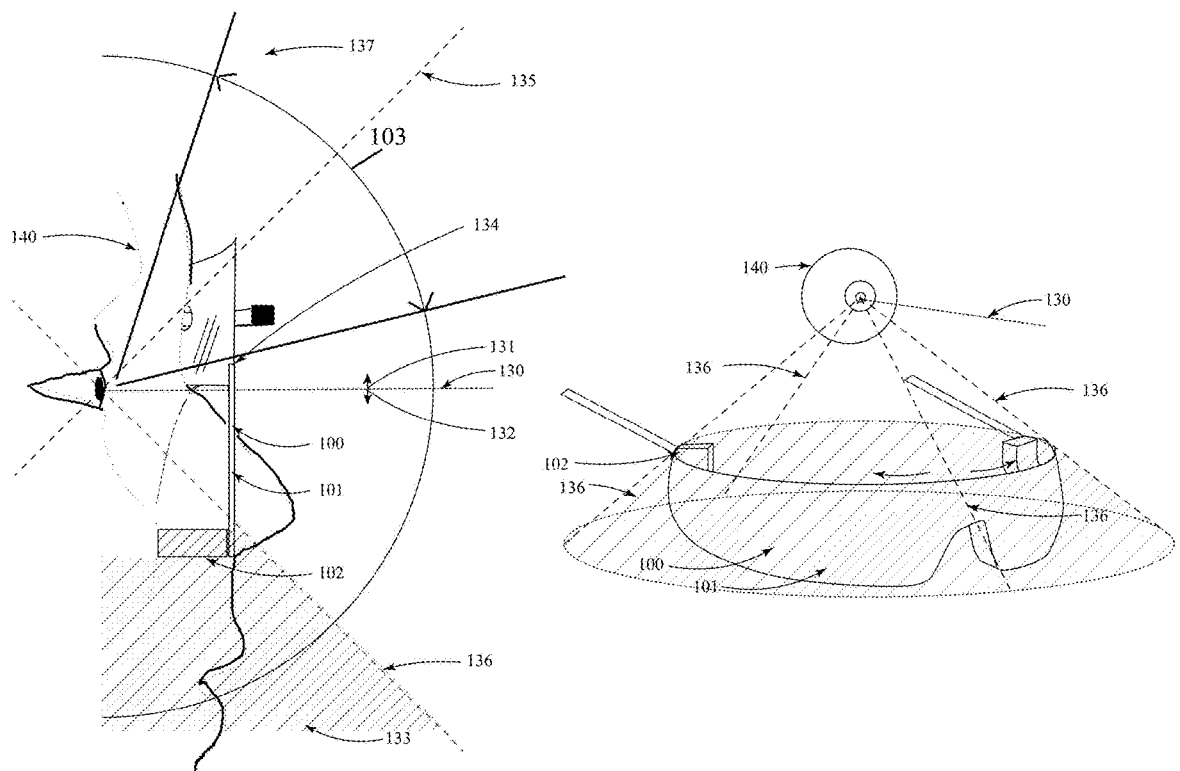
Figure 5 – Section – Visual Field Obstruction Limits
Figure 6 – Perspective Cone of Blocked Lower Visual Field

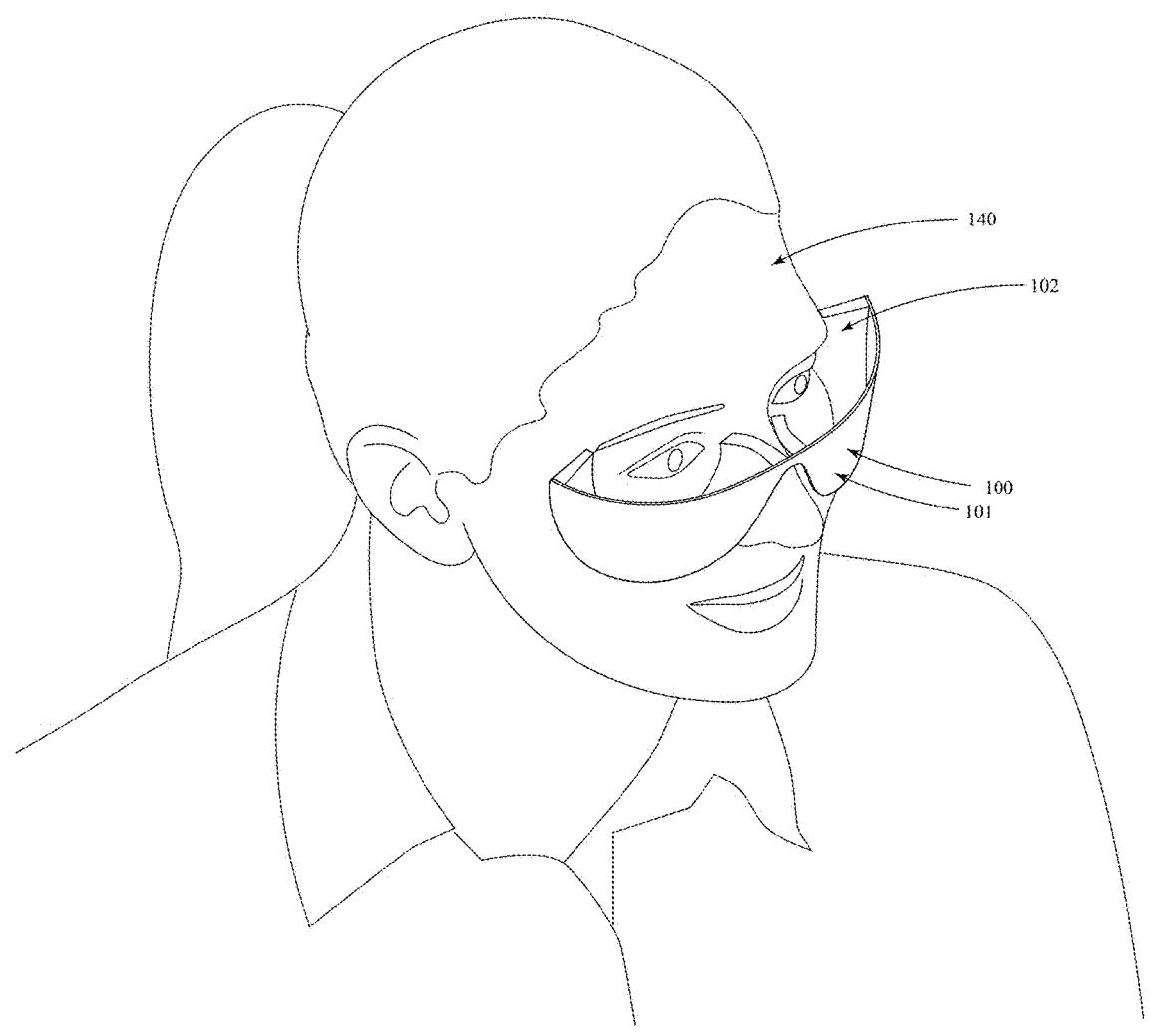
Figure 7 – Perspective View of Eyewear Apparatus in Use

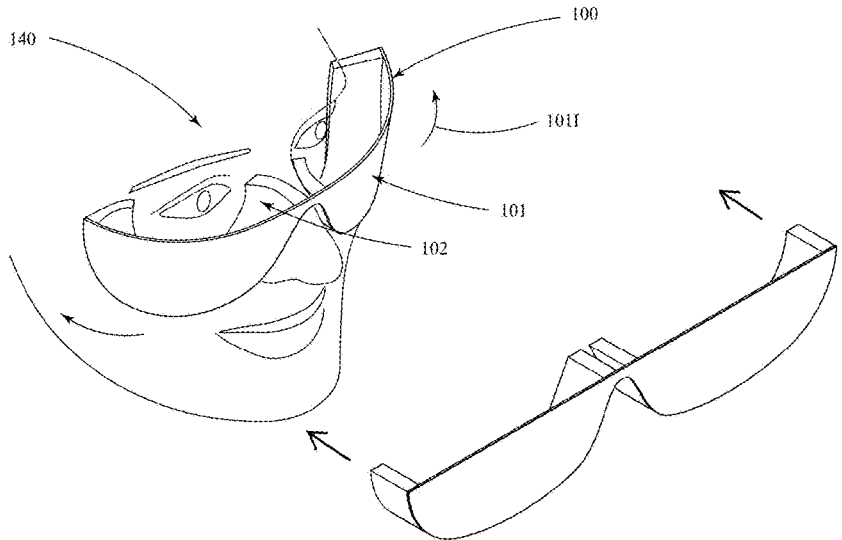
Figure 8 – Flexible Interface Conforming to Face
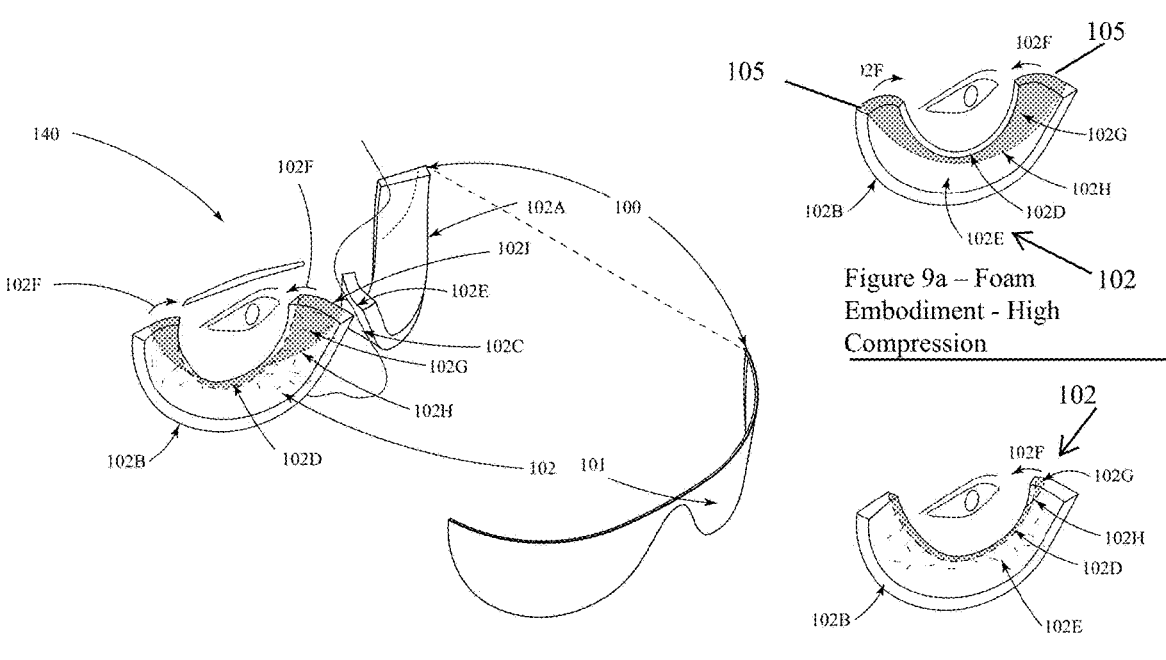
Figure 9 – Detail – Embodiments of Foam Interface Against Countoured Surface
Figure 9a – Foam Embodiment - High Compression
Figure 9b – Foam Embodiment - Low Compression

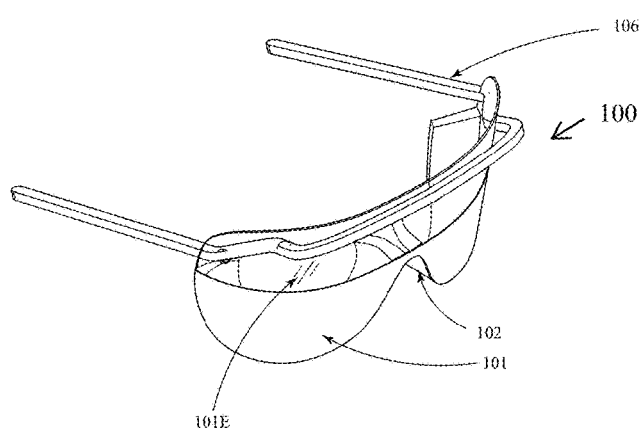
Figure 10 – Apparatus Embodiment with Transparent Upper Lens and Frame
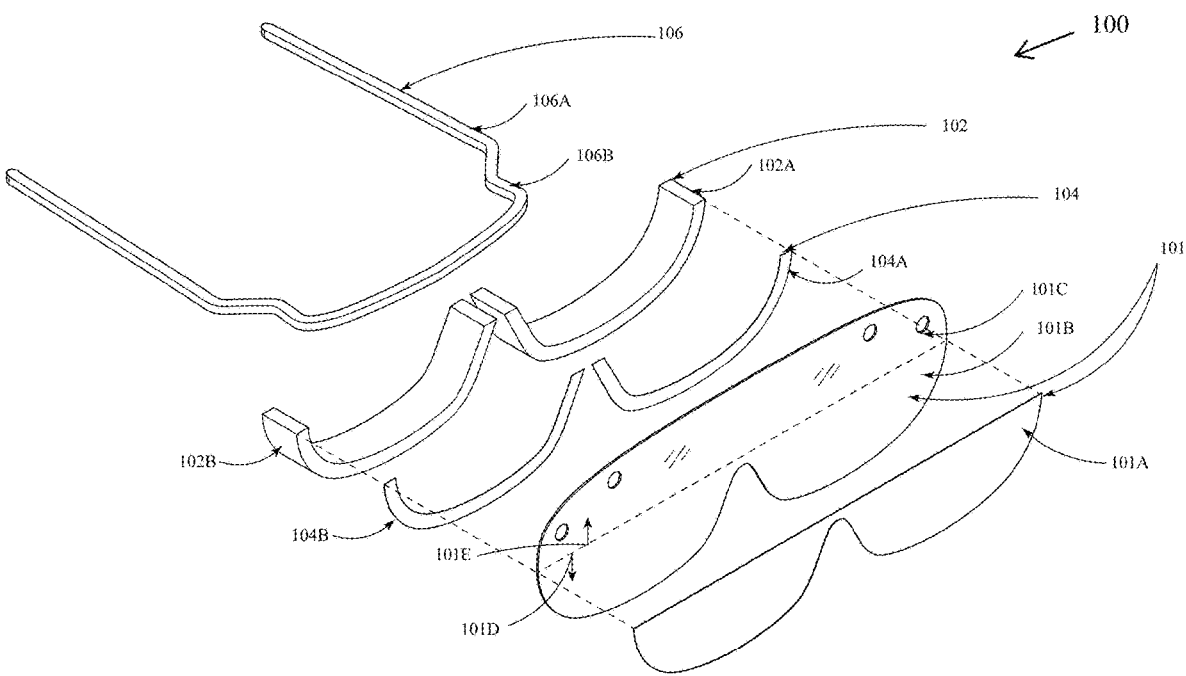
Figure 11 – Exploded Isometric of Single-Lens Embodiment

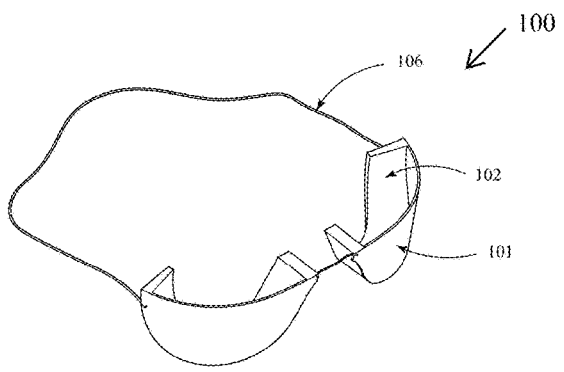
Figure 12 – Split-Lens Embodiment with Tensile Strap Frame
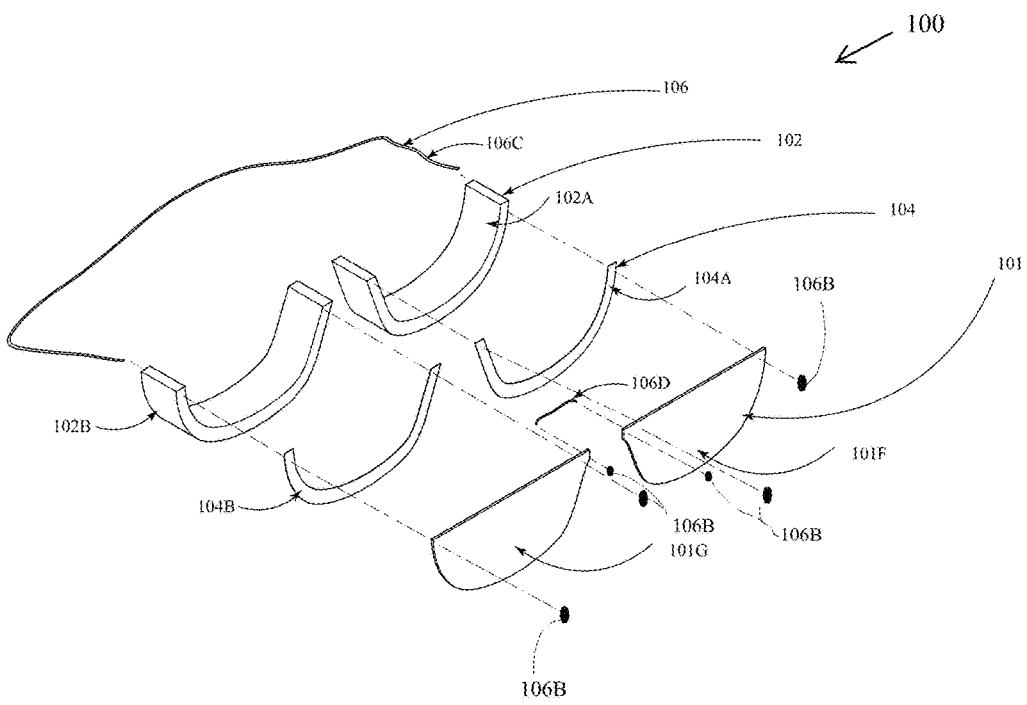
Figure 13 – Exploded Isometric of Split-Lens Embodiment

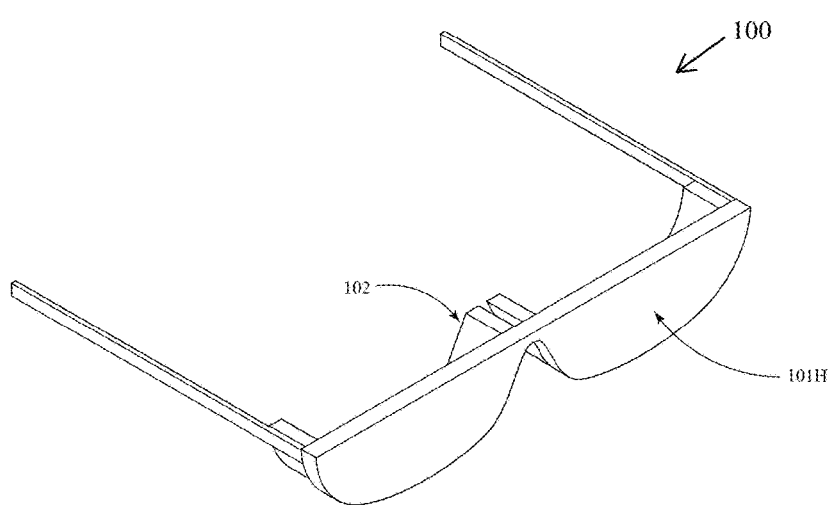
Figure 14 – Rigid Frame Embodiment with Opaque Lower Shield and Foam
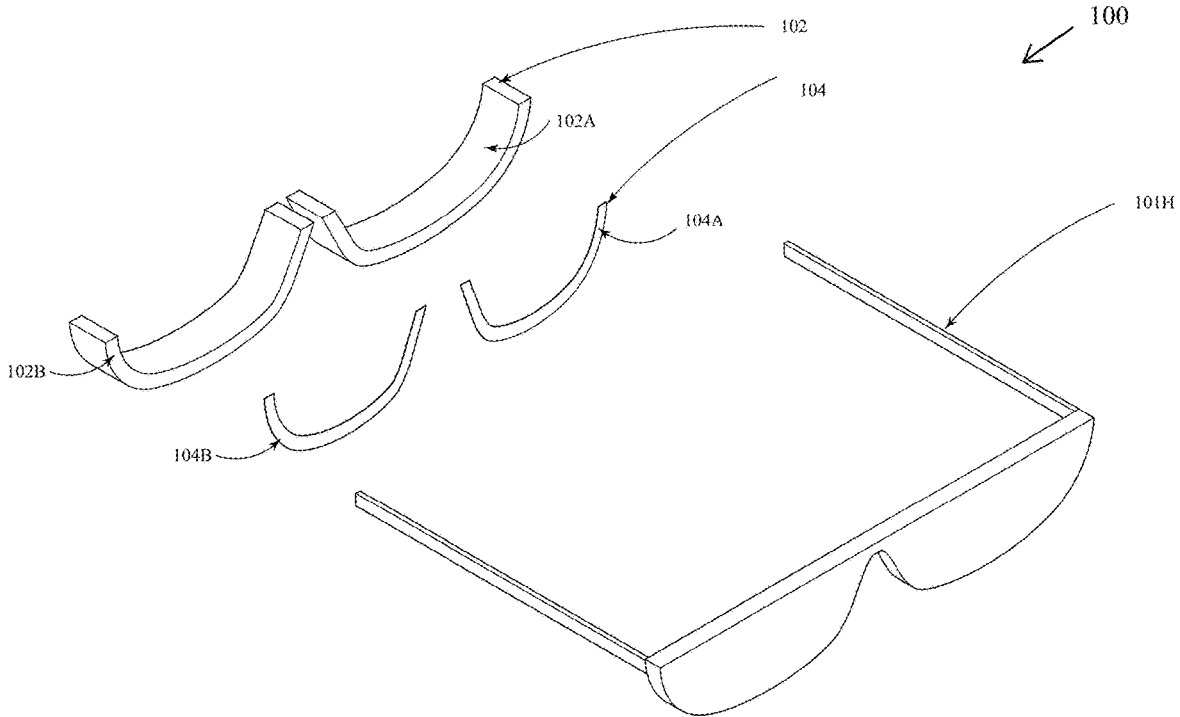
Figure 15 – Exploded Isometric of Rigid Frame Embodiment

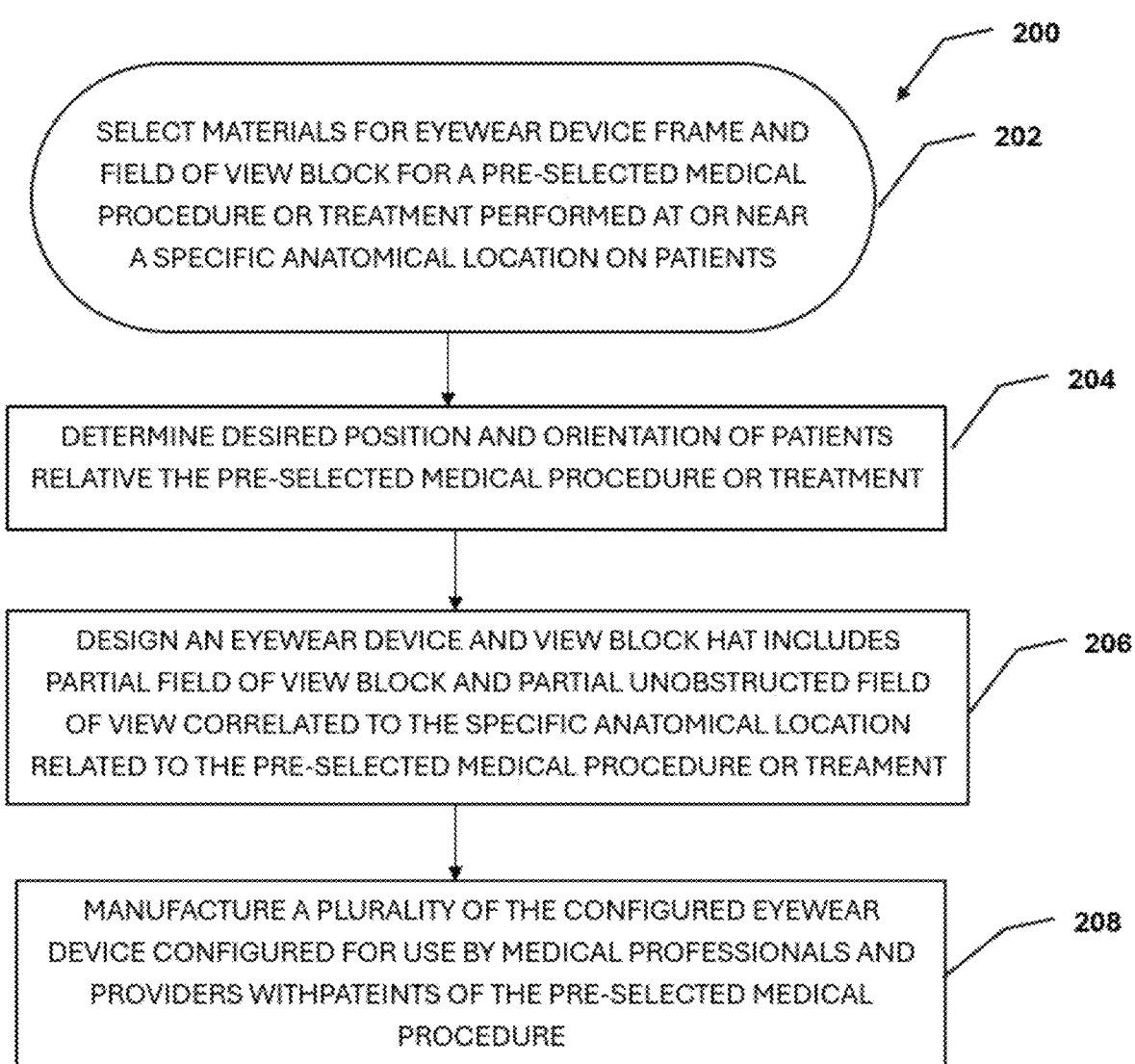

SELECT MATERIALS FOR EYEWEAR DEVICE FRAME AND FIELD OF VIEW BLOCK FOR A PRE-SELECTED MEDICAL PROCEDURE OR TREATMENT PERFORMED AT OR NEAR A SPECIFIC ANATOMICAL LOCATION ON PATIENTS

DETERMINE DESIRED POSITION AND ORIENTATION OF PATIENTS RELATIVE THE PRE-SELECTED MEDICAL PROCEDURE OR TREATMENT

DESIGN AN EYEWEAR DEVICE AND VIEW BLOCK HAT INCLUDES PARTIAL FIELD OF VIEW BLOCK AND PARTIAL UNOBSTRUCTED FIELD OF VIEW CORRELATED TO THE SPECIFIC ANATOMICAL LOCATION RELATED TO THE PRE-SELECTED MEDICAL PROCEDURE OR TREAMENT

MANUFACTURE A PLURALITY OF THE CONFIGURED EYEWEAR DEVICE CONFIGURED FOR USE BY MEDICAL PROFESSIONALS AND PROVIDERS WITHPATEINTS OF THE PRE-SELECTED MEDICAL PROCEDURE

FIG. 18B

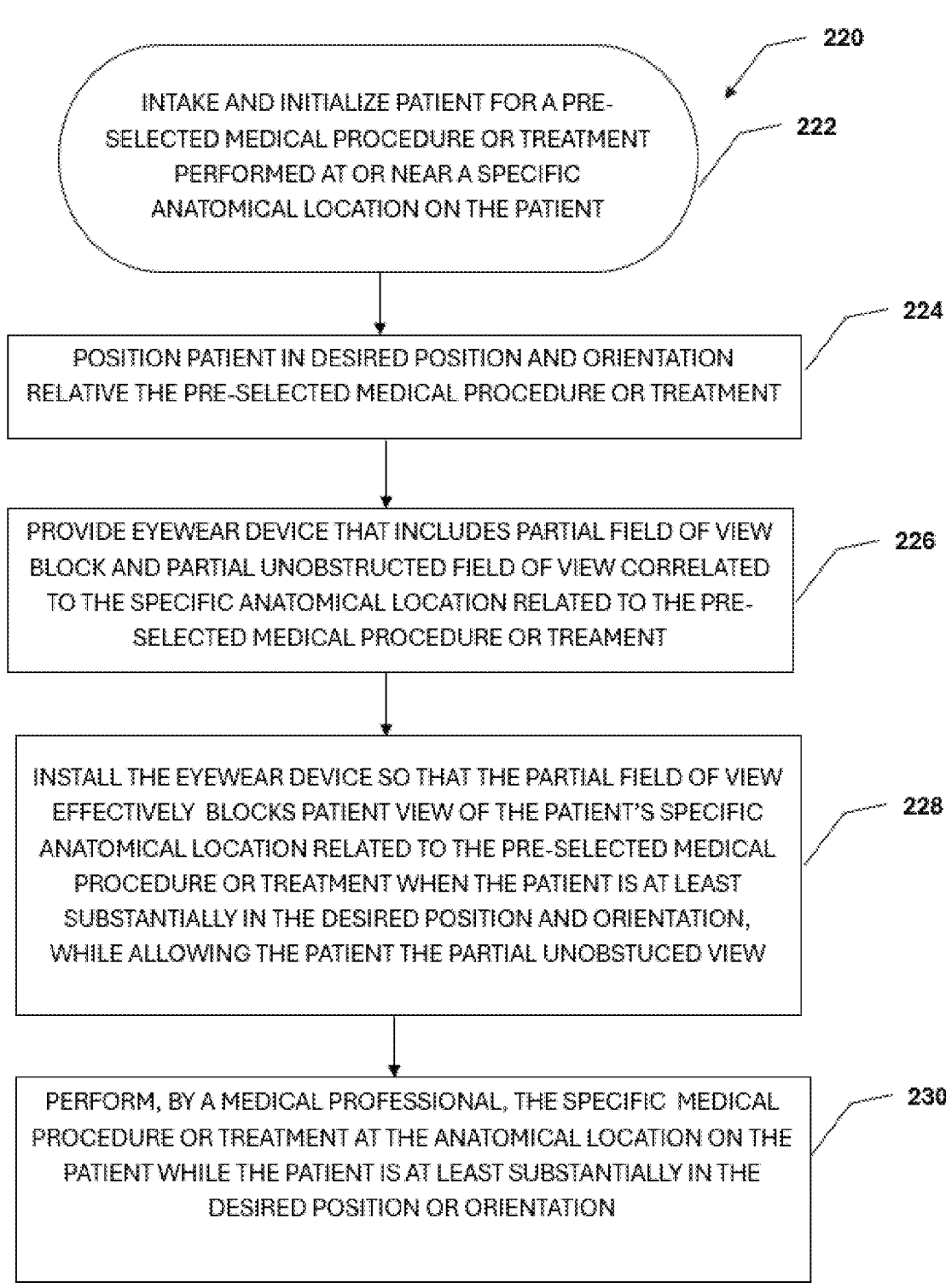

220

INTAKE AND INITIALIZE PATIENT FOR A PRE-
SELECTED MEDICAL PROCEDURE OR TREATMENT
PERFORMED AT OR NEAR A SPECIFIC
ANATOMICAL LOCATION ON THE PATIENT

222

POSITION PATIENT IN DESIRED POSITION AND ORIENTATION
RELATIVE THE PRE-SELECTED MEDICAL PROCEDURE OR TREATMENT

224

PROVIDE EYEWEAR DEVICE THAT INCLUDES PARTIAL FIELD OF VIEW
BLOCK AND PARTIAL UNOBSTRUCTED FIELD OF VIEW CORRELATED
TO THE SPECIFIC ANATOMICAL LOCATION RELATED TO THE PRE-
SELECTED MEDICAL PROCEDURE OR TREAMENT

226

INSTALL THE EYEWEAR DEVICE SO THAT THE PARTIAL FIELD OF VIEW
EFFECTIVELY BLOCKS PATIENT VIEW OF THE PATIENT'S SPECIFIC
ANATOMICAL LOCATION RELATED TO THE PRE-SELECTED MEDICAL
PROCEDURE OR TREATMENT WHEN THE PATIENT IS AT LEAST
SUBSTANTIALLY IN THE DESIRED POSITION AND ORIENTATION,
WHILE ALLOWING THE PATIENT THE PARTIAL UNOBSTUCED VIEW

228

PERFORM, BY A MEDICAL PROFESSIONAL, THE SPECIFIC MEDICAL
PROCEDURE OR TREATMENT AT THE ANATOMICAL LOCATION ON THE
PATIENT WHILE THE PATIENT IS AT LEAST SUBSTANTIALLY IN THE
DESIRED POSITION OR ORIENTATION

XY = FRONTAL PLANE
YZ = SAGITTAL PLANE
XZ = TRANSVERSE PLANE

100

Optional
Indicia

100

100

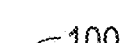
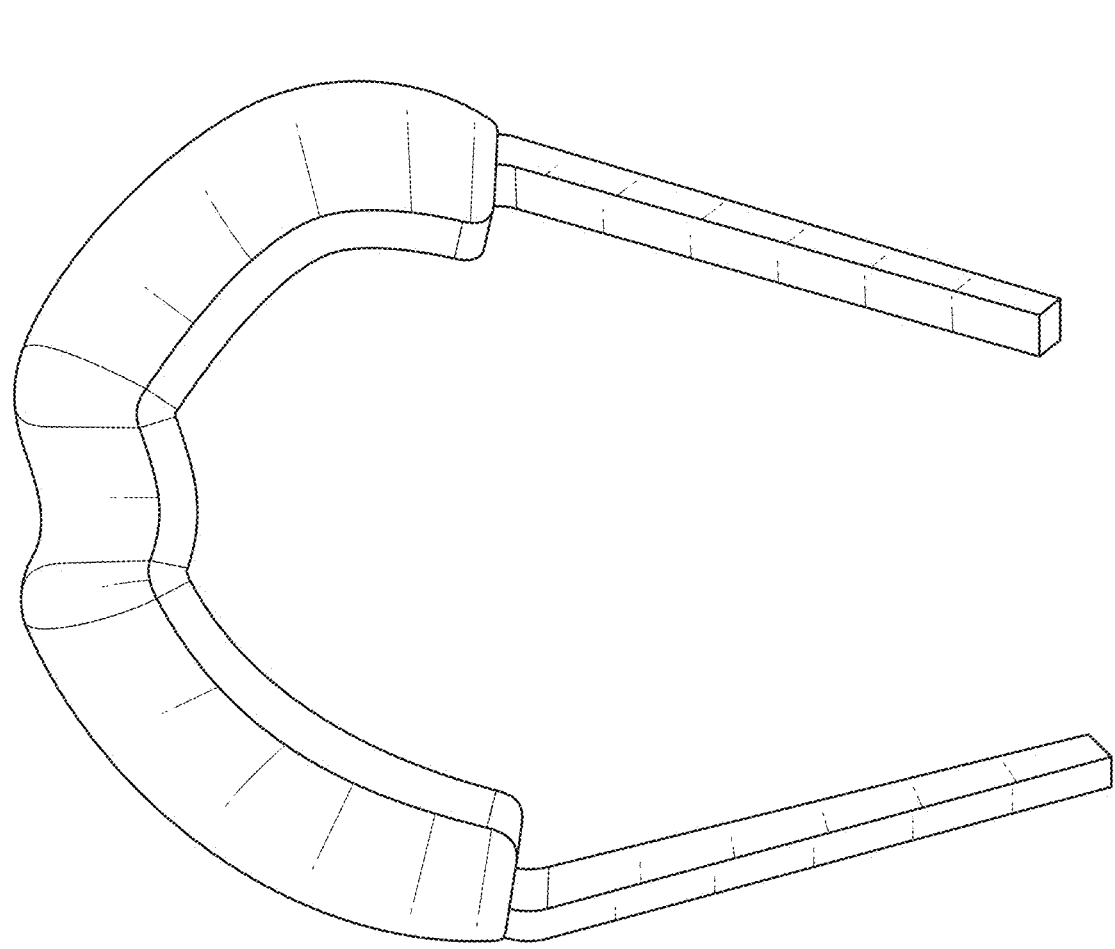
FIG. 25

100

Optional
Indicia

METHOD AND EYEWEAR APPARATUS FOR LOWER VISUAL FIELD OBSTRUCTION

CROSS-REFERENCE TO RELATED APPLICATIONS

This application claims the benefit of Provisional Application U.S. Ser. No. 63/678,722 filed on Aug. 2, 2024, all of which is herein incorporated by reference in its entirety.

TECHNICAL FIELD

This disclosure relates to vision-restricting devices, and more particularly to methods and apparatuses for obstructing the lower or a partial visual field using wearable eyewear to reduce visual exposure to procedural stimuli during medical interventions, including vascular access and soft-tissue biopsy procedures, including for partially obstructing patient visual field related to a specific anatomical location or area on a patient when the patient is appropriately positioned and oriented during a pre-selected medical procedure or treatment, while allowing a partial unobstructed patient visual field.

BACKGROUND

Breast biopsy procedures, including the relatively new upright biopsy method, present significant challenges in maintaining patient comfort and procedural efficiency. The upright method requires the patient to sit in a chair and look away from the incision point. During these procedures, patients often experience vasovagal syncope (fainting), which poses serious risks. Fainting during the procedure can lead to unintentional movement, resulting in tissue tearing, widening of the incision, increased bleeding, and the formation of hematomas. Additionally, such incidents necessitate the halting of the procedure to manage the patient's condition, which often involves reestablishing sterile fields and potentially replacing medical equipment, such as biopsy needles. This interruption not only increases patient discomfort but also demands additional time and resources from medical staff and facilities (Malave, Brian, and Bruce Vrooman. "Vasovagal Reactions during Interventional Pain Management Procedures—A Review of Pathophysiology, Incidence, Risk Factors, Prevention, and Management." Medical Sciences 10, no. 3 (2022): 39. https://doi.org/10.3390/medsci10030039, incorporated by reference herein). Current measures to enhance patient comfort, such as adjusting arm positions, have proven insufficient. Therefore, there is a need for a solution that can prevent patients from viewing the procedure, thereby reducing anxiety and the likelihood of fainting. The technical solution of the present disclosure addresses this need by introducing eyewear specifically designed to block the patient's view of the medical procedure at the patient's anatomy, thereby enhancing both patient comfort and procedural efficiency. By the terms "effectively block" and "effective blocking" of a patient's view, or similar terms, it is meant that, when a device or technique according to the present disclosure is properly installed and used on a patient, and the patient is at least substantially in appropriate position and orientation relative the procedure, a typical patient cannot visually resolve what is in the blocked field of view sufficient to process and recognize what is occurring in the blocked field of view. This can range from complete vision blockage or enough so that a patient cannot visually recognize or resolve what is occurring at the procedure area or location at the patient's anatomy. In some embodiments, the blocking is by materials of or integrated into eyewear that provide opaqueness to substantially opaque or, in some embodiments, substantially translucent or light dispersive such that some movement can be perceived but without sufficient shape resolution to visually process and recognize specific anatomy, structures, medical tools or equipment, or a medical professional's hands. It some embodiments, the effective blockage is substantially of all lower forward and peripheral field of view relevant to medical procedures or treatments on or at the patient below the patient's eye level, including at and around the patient's nose, cheek bones, and temples, including effective blockage of gaps that typical eyewear have between the periphery of typical eyewear and the wearer's nose, checks, or temples. Embodiments of the disclosure can allow for some forward and upward field of view which can reduce patient anxiety and allow for non-verbal communication with the patient during the medical procedure. In other embodiments, the blocking is correlated to a specific anatomical location or region on the patient for a medical procedure or treatment when the patient is placed in a desired or appropriate position, posture, and orientation for the procedure or treatment.

Research has consistently shown that visual and auditory distractions can significantly reduce fear and anxiety during invasive medical procedures. For instance, a study demonstrated that visual distraction techniques, such as virtual reality, effectively lower anxiety levels in patients by diverting their attention away from the procedure (See, e.g., National Center for Biotechnology Information, 2021. "Looking at the needle versus looking away did not have a significant impact on pain but did significantly impact fear, with those who were told to look at the needle reporting significantly more fear." https://www.ncbi.nlm.nih.gov/pmc/articles/PMC8730672/, incorporated by reference herein; and Mithal, P, Simmons P, Cornelissen T, Wong H, Pillai Riddell R, McMurtry C M, Burry L, Stephens D, Taddio A. To look or not to look during vaccination: A pilot randomized trial. Can J Pain. 2018 Jan. 5; 2(1):1-8. doi: 10.1080/24740527.2017.1412254. PMID: 35005359; PMCID: PMC8730672 (incorporated by reference herein), which describes adverse patient reactions to needles such as during vaccination procedures).

Further supporting this, a study found that looking at a needle versus looking away significantly impacts fear, with those instructed to look at the needle reporting substantially higher fear levels (National Center for Biotechnology Information, 2021, supra). This aligns with findings from virtual reality research, which shows that immersive VR can significantly reduce procedural pain and anxiety by blocking out the physical surroundings and engaging the patient's attention (Frontiers, 2019. "The Effects of Virtual Reality on Procedural Pain and Anxiety in Pediatrics: A Systematic Review and Meta-Analysis." https://www.frontiersin.org/articles/10.3389/fpsyg.2019.02352/full.; and Lui C and Ma J-L (2019) Adult Attachment Style, Emotion Regulation, and Social Networking Sites Addiction. Front. Psychol. 10:2352. doi: 10.3389/fpsyg.2019.02352 (both incorporated by reference herein).

Additionally, research on the use of immersive environments like VR suggests that completely blocking the patient's view of the procedure helps to minimize anxiety and prevent vasovagal reactions. These studies collectively underscore the importance of visual field blockage in enhancing patient comfort and procedural efficiency (Academic OUP, 2021. "Visual and auditory distraction techniques can significantly reduce fear during invasive medical procedures." https://academic.oup.com/abm/article/55/11/1062/6209758; and Kilic A, Brown A, Aras I, Hui R, Hare J, Hughes L D, McCracken L M. Using Virtual Technology for Fear of Medical Procedures: A Systematic Review of the Effectiveness of Virtual Reality-Based Interventions. Ann Behav Med. 2021 Oct. 27; 55(11):1062-1079. doi: 10.1093/abm/kaab016. PMID: 33821879; PMCID: PMC8557375, both incorporated by reference herein).

By integrating these insights, the technology solution of the present disclosure aims to effectively block the patient's view of the medical procedure, thereby reducing anxiety and the likelihood of fainting. This innovation addresses the critical need for improved patient comfort and operational efficiency during medical procedures, which can include medical treatments or other processes on, at, or into a person's body.

In light of the foregoing, in medical procedures that pertain to anatomy below the patient's head, while the primary benefit of blocking the visual field is to prevent patients from seeing the procedure itself, a specific objective is to obstruct the view of the patient's own body below the head. Using coverings, walls, or complete field of vision blocks of the patient's body and surroundings might do so, but can interfere with the procedure, are cumbersome, and costly. They can make the patient feel isolated, which can promote anxiety. It can be crucial to maintain the upper field of vision to allow patients to see and communicate with medical staff, and to remain generally aware of their surroundings. This visibility can be beneficial for patient reassurance and for the medical staff to provide verbal or non-verbal instructions, which can help in maintaining a calm and cooperative patient during the procedure. Thus, some embodiments of the present disclosure focus on small, economical, wearable medical eyewear that completely blocks the lower field of vision while maintaining the upper field of vision right at or near the patient's eyes. It does not interfere with the procedure or surroundings. It is engineered to provide a partial restriction to field of view with a wearable device that is not cumbersome for the patient or clinicians. It also allows medical staff to better monitor physical indications of the patient's state by monitoring the patient's expressions, and with an engineered concurrent partial unobstructed field of view the patient does not feel isolated. Subtle, but important, benefits in medical procedures include both patient and medical professional. A technical solution is needed to improve patient experience and both physical and psychological comfort during a medical procedure.

This promotes improved patient outcomes from a medical procedure by minimizing patient movement or anxiety to allow medical professionals to perform their jobs without disruption. It also fosters non-verbal as well as verbal direct communication with the clinician(s) performing or attending the procedure because of partial unobstructed patient field of view of the clinician's face(s).

Many others have attempted to address visual field blockage with eyewear type devices for different purposes, yet none provide either a specific technological solution regarding medical procedures of the type described above or a comprehensive technological solution to the technological issues addressed by the invention. Here are a few examples, each incorporated by reference herein, to illustrate the gaps in previous attempts "Keyboard Practice Glasses" (U.S. Pat. No. 5,561,480, issued Oct. 1, 1996, incorporated by reference herein):

These glasses block the lower field of vision but do not address the peripheral vision, leaving gaps that can still cause distraction.

"Peripheral View Blinders" (U.S. Pat. No. 4,298,991, issued Nov. 10, 1981, incorporated by reference herein): Many attempts, like this one, focus on blocking the peripheral vision but fail to transition the blockage to the main field of vision, and do not effectively separate the lower and upper fields of vision.

"Eyewear for Blocking Lower Vision Field" (WO2023146415A1, published Aug. 10, 2023, incorporated by reference herein): While addressing the lower field of vision and contouring to the face, these glasses do not sufficiently block the peripheral lower field of vision, leading to incomplete visual obstruction.

"Therapeutic Glasses and Method for Using the Same" (U.S. Pat. No. 6,145,983, issued Nov. 14, 2000, incorporated by reference herein): These glasses are designed for therapeutic needs and blocking visual fields but do not focus on the lower region specifically, nor do they eliminate gaps in the lower field of vision.

Other Documents

Other documents the inventors are aware of are:

| Publication Date | Publication Title | Patent Number |
|---|---|---|
| Oct. 19, 1971 | Dribble Teaching Aid | U.S. Pat. No. 3,613,116 |
| May 9, 1972 | Under-the-Eye Shade | U.S. Pat. No. 3,660,852 |
| Nov. 10, 1981 | Peripheral View Blinders | U.S. Pat. No. 4,298,991 |
| Oct. 16, 1990 | Protective Spectacles | U.S. Pat. No. 4,963,013 |
| Mar. 7, 1995 | Side Shield for Spectacles | U.S. Pat. No. 5,394,567 |
| Aug. 6, 1996 | Method and Kit for Attaching Side Shields to Eyeglass Temples | U.S. Pat. No. 5,543,864 |
| Oct. 1, 1996 | Keyboard Practice Glasses | U.S. Pat. No. 5,561,480 |
| Nov. 14, 2000 | Therapeutic Glasses and Method for Using the Same | U.S. Pat. No. 6,145,983 |
| Aug. 19, 2004 | Adjustable Glasses for Viewing Objects | US20040161730 A1 |
| Jul. 7, 2005 | Head-Mounted Display Device | US20050146674 A1 |
| Jun. 14, 2007 | Therapeutic Device for Reducing Anxiety | US20070132943 A1 |
| Oct. 22, 2009 | Corrective Eyeglasses | US20090262299 A1 |
| May 2, 2013 | Eyewear for Limiting Wandering Vision | US20130107198 A1 |
| Mar. 31, 2016 | Virtual Reality Therapy Apparatus and Method | US20160089272 A1 |
| Apr. 6, 2017 | Method and Portable Aid for Mindfulness Meditation | US20170097522 A1 |
| Jul. 18, 2017 | Athletics Visual Aid Focus Device | U.S. Pat. No. 9,709,828 |
| Feb. 15, 2018 | Protective Eyewear with Augmented Reality Display | US20180059438 A1 |
| Nov. 13, 2018 | Indoor Outdoor Sunglasses | U.S. Pat. No. 1,012,6570 |
| Dec. 4, 2020 | Vision Obstruction Device for Sports Training | FR3110714A1 |
| Sep. 28, 2023 | Eyewear for Enhanced Visual Perception | WO2023146415A1 |
| May 10, 1977 | Hockey Helmet Attachment | U.S. Pat. No. 4,022,466 |
| Jan. 19, 2022 | Vorrichtung als Sichtblende zum Abdecken des unteren Sichtfeldes | EP3940451A1 |

Despite the efforts in these prior attempts, none have successfully addressed the complete or effective blockage of the lower field of vision, including both direct and peripheral vision. Each cited invention demonstrates various degrees of blockage but also reveals significant limitations. For instance, the Keyboard Practice Glasses (U.S. Pat. No. 5,561,480) primarily address the immediate downward vision but fail to prevent peripheral distractions. Similarly, the Peripheral View Blinders (U.S. Pat. No. 4,298,991), while effective in blocking side views, do not extend the visual blockage to the main field of vision where medical procedures are often visible.

The Eyewear for Blocking Lower Vision Field (WO2023146415A1) addresses the contouring to the face and partially blocks the lower vision field but leaves gaps that can allow for peripheral distractions. The Therapeutic Glasses (U.S. Pat. No. 6,145,983) focus on altering psychological states through partial visual field blockage but do not provide a comprehensive solution for medical procedure settings, as they do not eliminate gaps in the lower visual field.

These examples underscore the need for a technological solution to issues such as with medical procedures. The present disclosure provides a significant advancement by offering a wearable device that ensures complete or effective blockage of the lower visual field, including both direct and peripheral vision. This design can effectively eliminate the user's view of their own body and the medical procedure, thereby addressing the shortcomings of previous solutions. The solution of the present disclosure is a small form factor eyewear sized and type device that controls patient field of view right at the patient's eyes instead of sheets, covers, walls, or enclosures around the procedure site, with the controlled field of view related to partial effective blockage of field of view to the procedure site on the patient's body but with a concurrent unobstructed partial field of view. This comprehensive approach not only enhances patient comfort and reduces anxiety but also increases procedural efficiency by minimizing interruptions due to patient reactions, as well as other benefits to both the patient and the medical provider.

Goldman Visual Field

To understand the field of visual obstruction addressed by present disclosure, imagine a subject seated at a standard visual field assessment station, placing their chin on a rest to stabilize the head while gazing directly forward. In this neutral position, the horizontal meridian spans across the visual field from left to right. If the subject then shifts their gaze downward to 45 degrees, everything visible below that point—across the full arc of vision—is considered the lower visual field. The apparatus and method described herein are configured to block this region specifically. See, e.g., FIGS. 4-6, 16A-B and 17A-B.

This zone—from 45 degrees to 90 degrees inferior—is fully and continuously obstructed through a combination of an opaque lens (sometimes referred to as an eyeshield as it does not have to be optical in quality or function) and a conformable, compressible foam pad (sometimes referred to as a compressible resilient member). The lens provides optical occlusion, while the foam ensures there are effectively no gaps at the skin-facing surface. Together, they create a wraparound visual barrier that extends laterally and downward, even into the lower peripheral zones.

This specific angular range is not arbitrary. Studies evaluating human gaze and head movement have found that the 30-45 degree inferior boundary effectively delineates the threshold below which the body becomes visible, even with moderate tilts or turns of the head. In other words, visual stimuli like a patient's chest, limbs, or procedural field remain hidden when obstruction begins at 45 degrees, making it a clinically meaningful and repeatable threshold for preventing unwanted visual triggers.

The Goldmann visual field test is a standard method used in ophthalmology to map and evaluate the extent of an individual's visual field. Sec, e.g., Dersu, Inci & Wiggins, Michael & Luther, Anne & Harper, Richard& Chacko, Joseph. Understanding Visual Fields, Part I; Goldmann Perimetry, January 2006, https://222.researchgate.net/publication/237684037, incorporated by reference herein, also found at Journal of Ophthalmic Medical Technology, Vol. 2, No. 2, June 2006, incorporated by reference herein.

Some of the devices mentioned earlier fall short of this standard. Some obstruct only the frontal downward view, failing to address the lateral peripheral vision. Others rely solely on rigid materials or partial coverage, allowing visibility through gaps or edges. The current disclosure's unique combination of materials and geometry ensures continuous obstruction of the defined field.

Embodiments of one or more aspects of the present disclosure includes this 45-90 degree inferior region. However, they also can allow for partial coverage between 45 degrees inferior and 45 degrees superior depending on configuration-such as the upper edge of the foam or lens. That upper limit can be intentionally left unobstructed or transparent, preserving ambient awareness and minimizing disorientation. While some embodiments support higher coverage if desired, the region above 45 degrees superior can be functionally excluded from full occlusion, helping maintain a user's comfort and spatial orientation. Other embodiments can allow for other partial field of view blockage as correlated to need or desire of the designer or relative to a specific anatomical location or area for a specific medical procedure or treatment.

SUMMARY OF THE INVENTION

According to embodiments that include one or more aspects of the disclosed invention, an eyewear apparatus is configured to obstruct the lower visual field of a user during procedures where visual exposure to the body may induce anxiety, discomfort, or vasovagal response. The apparatus comprises a lens or eyeshield with a lower opaque region that blocks the lower field of vision, and a compressible foam pad or other compressible material affixed along the lower region of the lens or shield to promote a continuous, gapless visual barrier. This configuration ensures that no discernible form (including any tool, any part of related procedural equipment, or any part of a clinician) is visible within the lower field while preserving ambient awareness through an unobstructed upper visual region. This is particularly suited for use during vascular access or other interventional procedures or treatments and may improve patient comfort and outcomes by eliminating procedural visual triggers.

According to embodiments that include one or more aspects of the disclosed invention, an eyewear device for a patient and method of use is designed to effectively block patient field of vision of medical procedures or treatments at or on the patient. Patient field of view of the area(s) at or around the location of the medical procedure or treatment is effectively blocked by structure(s), materials, or techniques on the wearable device right at and around the patient's eyes. This allows for temporary field of patient vision control that can be selectively quickly and easily installed on and removed from the patient. Its form factor can be at least similar to typical eyewear. It can be made of materials and manufacturing processes that make it relatively small in size, weight, and cost, and thus can be one-time use and disposable, which can be mandated in certain medical situations. The effectively blocked field of view can be engineered relative to the specific medical procedure or treatment, the procedural area or location the medical procedure or treatment is conducted on the patient's body, and the position, posture, and orientation of the patient relative to earth during the procedure or treatment. In some non-limiting embodiments, the eyewear and method block a lower and at least some peripheral field of view of the patient for medical procedures or treatments below eye level of the patient at least when the patient is in the correct body posture and orientation for the medical procedure or treatment. In some non-limiting embodiments, the eyewear and method block a lower and at least some peripheral field of view for medical procedures or treatments below eye level of the patient when the patient posture and orientation is sitting upright or at some upright angle to horizontal and not supine.

In some non-limiting embodiments of the disclosed invention, a wearable device for a patient and method of use is designed to both effectively block patient field of view of medical procedures or treatments at or on the patient while retaining or allowing some field of view in at least some other directions. One example is retaining or allowing a field of view away from the medical procedure(s) or treatment(s) procedural area. This can reduce patient anxiety and promote patient comfort as compared to complete blockage of all or most of the patient's field of view, and can benefit both patient and medical providers by allowing or facilitating at least non-verbal communication between patient and medical provider(s) before, during, and after a medical procedure or treatment; which can also improve verbal communication by allowing both persons to see each other's non-verbal cures and mouthing's of words with the auditory reception of speech.

In one non-limiting embodiment of the disclosed invention, a wearable device for a patient and method of use is designed to both effectively block patient field of view of medical procedures or treatments at or on the patient while retaining or allowing some field of view in at least some other directions. One example is retaining or allowing a field of view away from the medical procedure(s) or treatment(s) procedural area(s). This can reduce patient anxiety and promote patient comfort as compared to complete blockage of most or all of the patient's field of view, and can benefit both patient and medical providers by allowing or facilitating at least non-verbal communication between patient and medical provider(s) before, during, and after a medical procedure or treatment; which can also improve verbal communication by allowing both persons to see each other's non-verbal cures and mouthing's of words with the auditory reception of speech.

In one non-limiting embodiment of the disclosed invention, a wearable device for a patient and method of use is designed to both effectively block patient field of view of medical procedures or treatments at or on the patient while retaining or allowing some field of view in at least some other directions, by fashioning the form factor and function of a frame to essentially emulate typical eyewear for familiarity to the patient, and also be lightweight and easily mounted or removed from the patient. The frame can carry or support an eye shield or shields configured to either cover some partial field of view of the wearer with an effective block of field of view relevant to a procedural area for a medical procedure or treatment, while leaving unobstructed and unblocked the patient's remaining normal field of view. Alternatively the eye shield or shields, when installed, can essentially cover at least most or even all the patient's field of view, but have portions which partially effectively block field of view of the procedural area but have light transmissive or transparent portions that do not obstruct a partial field of view different from the blocked one. In some embodiments, the field-of-view blocking structure or techniques is at the eye shield(s) and frame to create the effective blocking of the desired partial patient field of view.

One configuration of the foregoing embodiment is that the eye shield(s) effectively block(s) vision through at least a portion of the eye shield(s) relative to field of view of the relevant medical procedure or treatment, and the frame and eye shield form factors hug the patient's face to effectively block the intended patient field of vision to be blocked. This can be by nature of the eye shield material itself (e.g., the blocking portion is opaque or substantially opaque). Alternatively, a structure can be placed over the eye shield to do so (e.g., a vision-blocking film, layer, or substance). Alternatively, both the material of the eye shield and other structure can be placed on the eye shield to engineer the intended effective blocking of patient field of view. The frame can also have some efficacy in field of view blocking, whether at or around the eyes, the nose, or the temples.

Another configuration of the foregoing embodiment is that in addition to effective vision blocking by at least part of the eye shield and frame, other vision blocking components or techniques can be added. For example, structure can be mounted on the frame to extend from and effectively close possible gaps between frame and eye shields and the patient's face. Non-limiting examples are small vision blocking pieces between one or more of frame or eye shield and a wearer's nose, and/or a wearer's check bones, and/or a wearer's temples. Non-limiting embodiments of these pieces can be thin, substantially solid flaps or walls, compressible materials such as foam or rubber, or a combination of the same. Such supplemental pieces can enhance the effective blocking of patient vision by blocking possible view through even small gaps between frame/eye shield(s) and the patients' facial anatomy.

In some non-limiting embodiments of the disclosure, the wearable device can be made of relatively low-cost materials which are approved for medical use (e.g., by the federal Food and Drug Administration (FDA)) (e.g. non-optical plastic for frame and eye shield(s)), and by low-cost manufacturing techniques (e.g., economical mass production techniques such as plastic molding, additive manufacturing, etc.), including the vision blocking features (e.g., films or thin layers that block vision, or built-in to frames/eye shield(s)), which promotes the ability to make them sufficiently cost-effective for one-time, disposable use for each patient.

According to one or more aspects of the disclosed invention, an integrated wearable device is configured to effectively block a partial field of the view of the wearer with a frame and eye shield(s) that have an aesthetic appeal. That appeal can, inter alia, include form factor, proportions, and other design features.

According to one or more aspects of the disclosed invention, a wearable device is configured to effectively block a partial field of view of the wearer for medical procedures or treatments that can include selectable color(s), form factor, and/or indicia. The color(s) can be selected according to either need or desire of a designer or a customer of the wearable devices. They can be selected for psychological effects on patients (to reduce anxiety) and/or aesthetic appeal. For example, FIGS. 28A-B, 29-24, and 35A-E illustrate the color pink The indicia can be selected according to either need or desire of a designer or customer of the wearable devices. The indica can communicate information regarding usage of the wearable devices (e.g., one-time use only) or information about the medical provider of the medical procedure or treatment (e.g., trademark branding or provider identification).

According to one or more aspects of the disclosure, a method of making eyewear devices includes selecting the materials and form factor, selecting a field of view to partially effectively block when installed on a patient (e.g., what type of procedure or treatment on what procedural area of the patient), and then forming or assembling the materials to promote that effective field of vision blocking when the devices are installed on patients. This can include intentionally effectively blocking a relevant partial field of vision with the devices. Alternatively, the devices can cover all or most of the wearer's field of vision, but have portions that effectively block a relevant partial field of vision and portions that do not obstruct another partial of field of vision. An example of the latter is to effectively block a generally downward field of vision to block view of a medical procedure or treatment below the patient's head but leave an unobstructed partial field of vision upwardly so that the patient can see the room or clinicians.

According to one or more aspects of the disclosure, a method of reducing anxiety and increasing comfort of a patient during a medical procedure or treatment comprises at least partially effectively blocking the patient's field of view of the relevant procedural location and tools used on the patient during the procedure or treatment. Non-limiting examples are effectively blocking a patient's field of view below the patient's eye level and at least partially the patient's peripheral vision on both sides during an invasive procedure such as an interventional biopsy below the patient's head (e.g. needle-based breast biopsy) or a vascular access (e.g., needle-based access for blood donors or for insertion of catheters).

According to embodiments of the present disclosure, the eyewear device with field of view control can be of a form factor and configuration that universally fits a variety of typical human head sizes and shapes. Alternatively, different models can be configured to fit sub-ranges of different sized/shaped human heads (e.g., small, medium, large, extra-large). Additionally, embodiments can have a form factor, shape, and size that comfortably and stably mounts to a patient's head over the patient's optical glasses (in the manner some sunglasses fit over and although a wearer to wear them concurrently over the wearer's optical glasses).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1—Perspective—Procedure Setup Without Eyewear

Figure 16A:
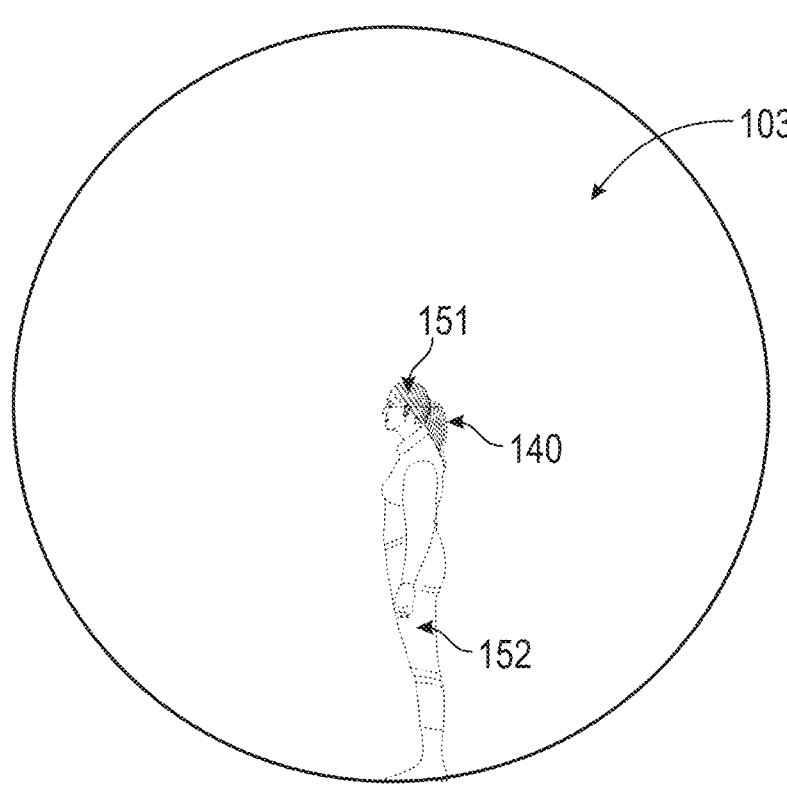

Depicts diagrammatically a representative medical procedure environment involving a subject and clinician, prior to application of an exemplary embodiment of a vision-restricting apparatus according to one or more aspects of the invention.

FIG. 2—Perspective—Application of Eyewear Apparatus

Depicts diagrammatically the application of an exemplary embodiment of a vision-restricting apparatus to a subject prior to a medical procedure, according to one or more aspects of the invention.

FIG. 3—Perspective—Procedure Performed with Eyewear in Place

Depicts diagrammatically a medical procedure being performed on a subject wearing an exemplary embodiment of a vision-restricting apparatus, according to one or more aspects of the invention.

FIG. 4—Diagram—Visual Field with Claimed Partial Inferior Obstruction

Depicts diagrammatically a Goldmann-style visual field chart illustrating the claimed blocked region extending downward from a fixed top boundary, as well as an upper transparent region that remains visible to the subject.

FIG. 5—Section—Visual Field Obstruction Limits

Depicts a vertical sectional diagram showing the subject wearing the apparatus and illustrating the resulting inferior visual obstruction. The figure includes the subject, an exemplary embodiment of an apparatus, and its components, according to one or more aspects of the invention, along with the visual field regions and the adjustable range for the top boundary of the blocked region.

FIG. 6—Perspective-Cone of Blocked Lower Visual Field

Depicts a perspective view of an exemplary embodiment of a vision-restricting apparatus from below the subject's eye, illustrating the spatial relationship between the apparatus and the inferior field of vision, according to one or more aspects of the invention. Dashed lines show the angular limits of the blocked region originating from the user's eye.

FIG. 7—Perspective View of Eyewear Apparatus in Use

Depicts a perspective view of an exemplary embodiment of a vision-restricting apparatus including labeled components according to one or more aspects of the invention, as positioned adjacent to a user for illustrative context.

FIG. 8—Isometric View of Apparatus with Flexible Lens Wrapping Around Contour Depicts an embodiment of an exemplary embodiment of a vision-restricting apparatus with a flexible lens structure configured to bend around contoured surfaces according to one or more aspects of the invention, supporting continuous visual obstruction without reliance on a rigid frame.

FIG. 9—Detail—Nasal Bridge Interface with Dual Foam Pad Segments

Depicts a detailed sectional view of an exemplary embodiment of a vision-restricting apparatus according to one or more aspects of the invention at the nasal bridge region, illustrating the dual U-shaped foam segments and their configuration to form a continuous seal beneath the lens.

FIG. 9*a*—Depicts a high-compression embodiment of an exemplary embodiment of a foam interface with a wearable device according to one or more aspects of the invention in which the foam folds inward against itself under pressure, with the outer surface forming the sole contact interface against the user's face.

FIG. 9*b*—Depicts a low-compression embodiment of an exemplary embodiment of a foam interface with a wearable device according to one or more aspects of the invention wherein the foam retains more of its original shape, with the inner surface forming the sole contact interface against the user's face.

FIG. 10—Isometric View of Apparatus Embodiment with Transparent Upper Lens and Frame Depicts an assembled configuration of an exemplary embodiment of a vision-restricting apparatus 100 according to one or more aspects of the invention, showing the integration of the frame 106, foam interface 102, and a multi-zone lens that includes both an opaque lower region 101 and a transparent upper region 101E.

FIG. 11—Exploded Isometric View of Vision-Restricting Apparatus Components

Depicts the layered construction of an exemplary embodiment of a vision-restricting apparatus 100 with a wearable device according to one or more aspects of the invention, showing the relationship between the frame assembly 106, foam interface 102, adhesion layer 104, and lens structure 101. Each component is labeled to illustrate assembly orientation and material function.

FIG. 12—Isometric View of Split-Lens Embodiment with Tensile Strap Frame

Depicts an isometric view of an exemplary embodiment of a split-lens vision-restricting apparatus 100 according to one or more aspects of the invention including two opaque lens segments 101, a bilateral foam interface 102, and a flexible tensile strap frame 106 for retaining the structure in position.

FIG. 13—Exploded Isometric View of Split-Lens Embodiment

Illustrates the disassembled configuration of a split-lens version of an exemplary embodiment of the vision-restricting apparatus 100 with a wearable device according to one or more aspects of the invention, featuring two separate lens segments 101L, 101R, foam pads 102A, 102B, optional adhesive interfaces 104A, 104B, and a flexible tension frame 106 that wraps around the user's head or ears.

FIG. 14—Isometric View of Rigid Frame Embodiment with Opaque Lower Shield and Foam Depicts an isometric view of an exemplary embodiment of a vision-restricting apparatus 100 with a wearable device according to one or more aspects of the invention, featuring a rigid visor body 101H that integrates the lower shield and frame structure into a single molded component, with a foam interface 102 affixed along the interior.

FIG. 15—Isometric View of Rigid Visor Embodiment with Integrated Frame and Lens

Illustrates an exemplary embodiment of a vision-restricting apparatus 100 according to one or more aspects of the invention featuring a rigid visor body 101H combining the lower opaque region and frame structure into a single molded component, with a conforming foam interface 102 affixed to the interior surface.

FIG. 16A—Elevation-Visual Field—Without Eyewear

Depicts diagrammatically the elevational visual range of a person without eyewear according to any exemplary embodiment of the invention.

Figure 16B:
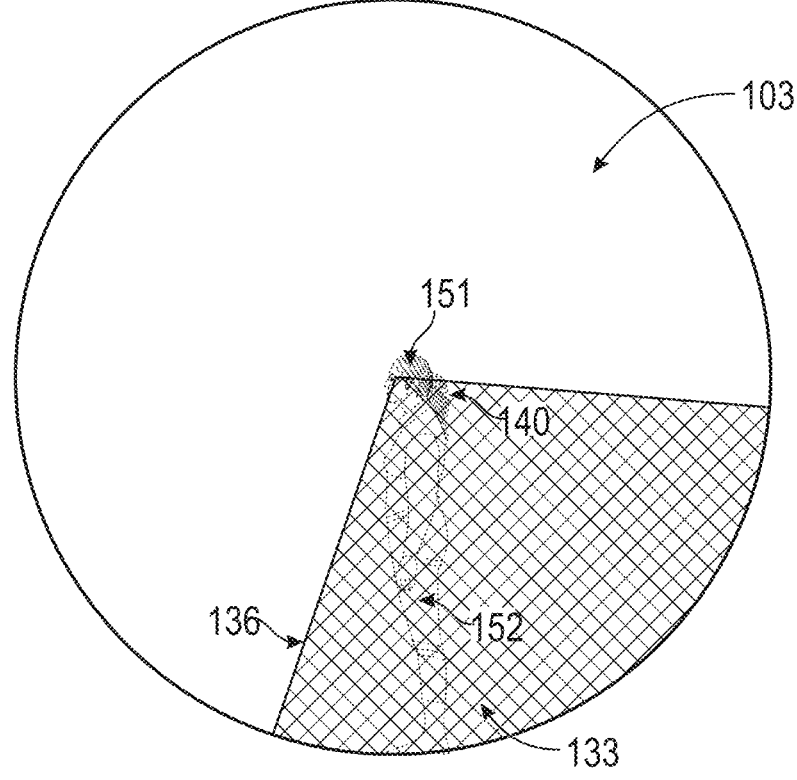

FIG. 16B—Elevation-Visual Field—With Eyewear

Depicts diagrammatically the elevational visual range of a person with an exemplary embodiment of eyewear according to one or more aspects of the invention.

Figure 17A:
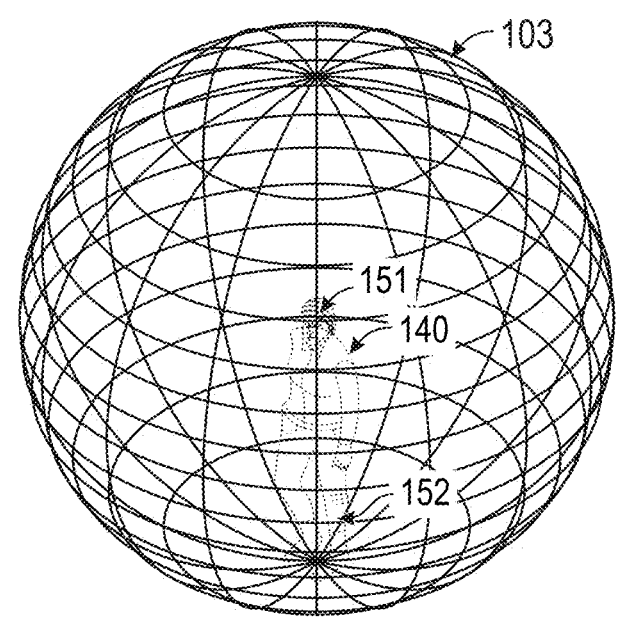

FIG. 17A—Isometric-Visual Field—Without Eyewear

Depicts diagrammatically an isometric view of the visual range of a person without eyewear according to any exemplary embodiment of the invention.

Figure 17B:
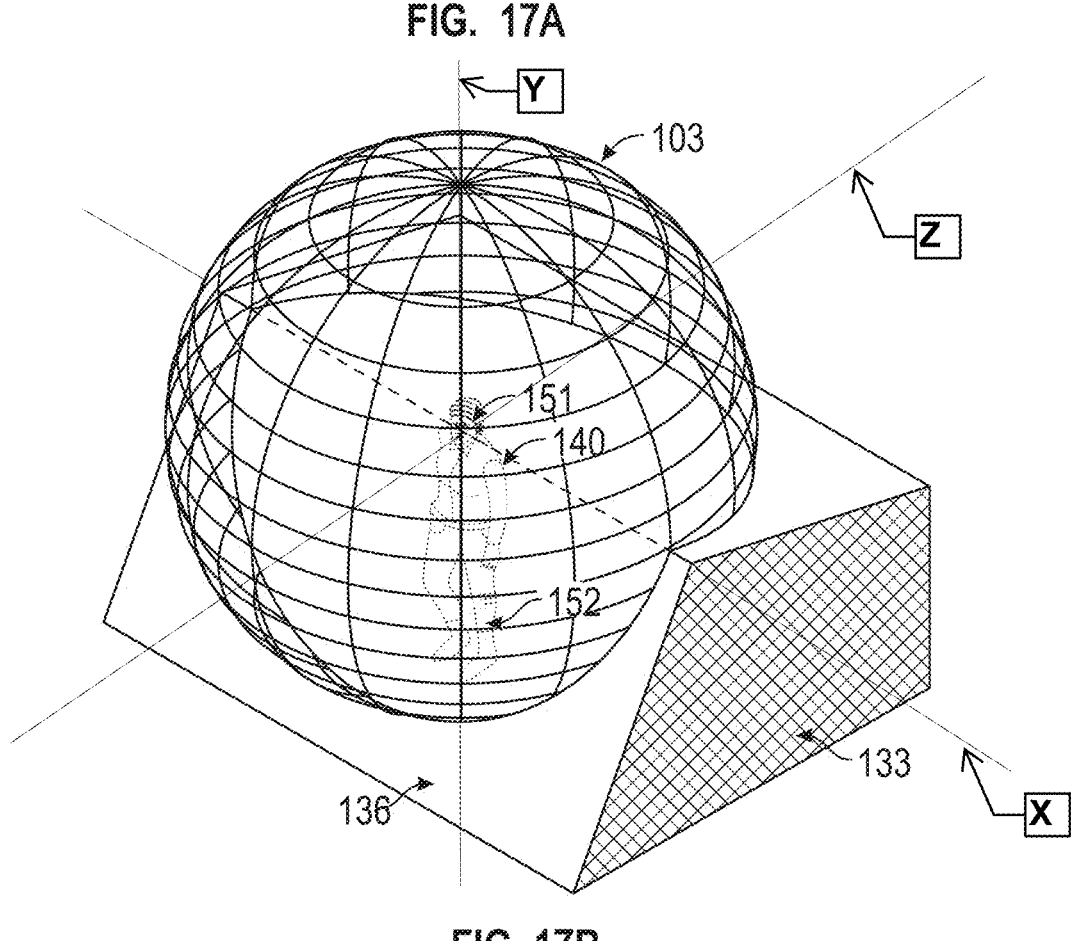

FIG. 17B—Isometric-Visual Field—With Eyewear

Depicts diagrammatically an isometric view of the visual range of a person with an exemplary embodiment of eyewear according to one or more aspects of the invention with XYZ axes superposed relative to an origin at or near a person's nose bridge. The YZ plane is a sagittal plane through the person. The XY plane is a frontal plane at the person's eyes. The XZ plane is a transverse plane along the top of the eyewear vision block of the eyewear according to exemplary embodiments of the present disclosure.

Figure 18A:
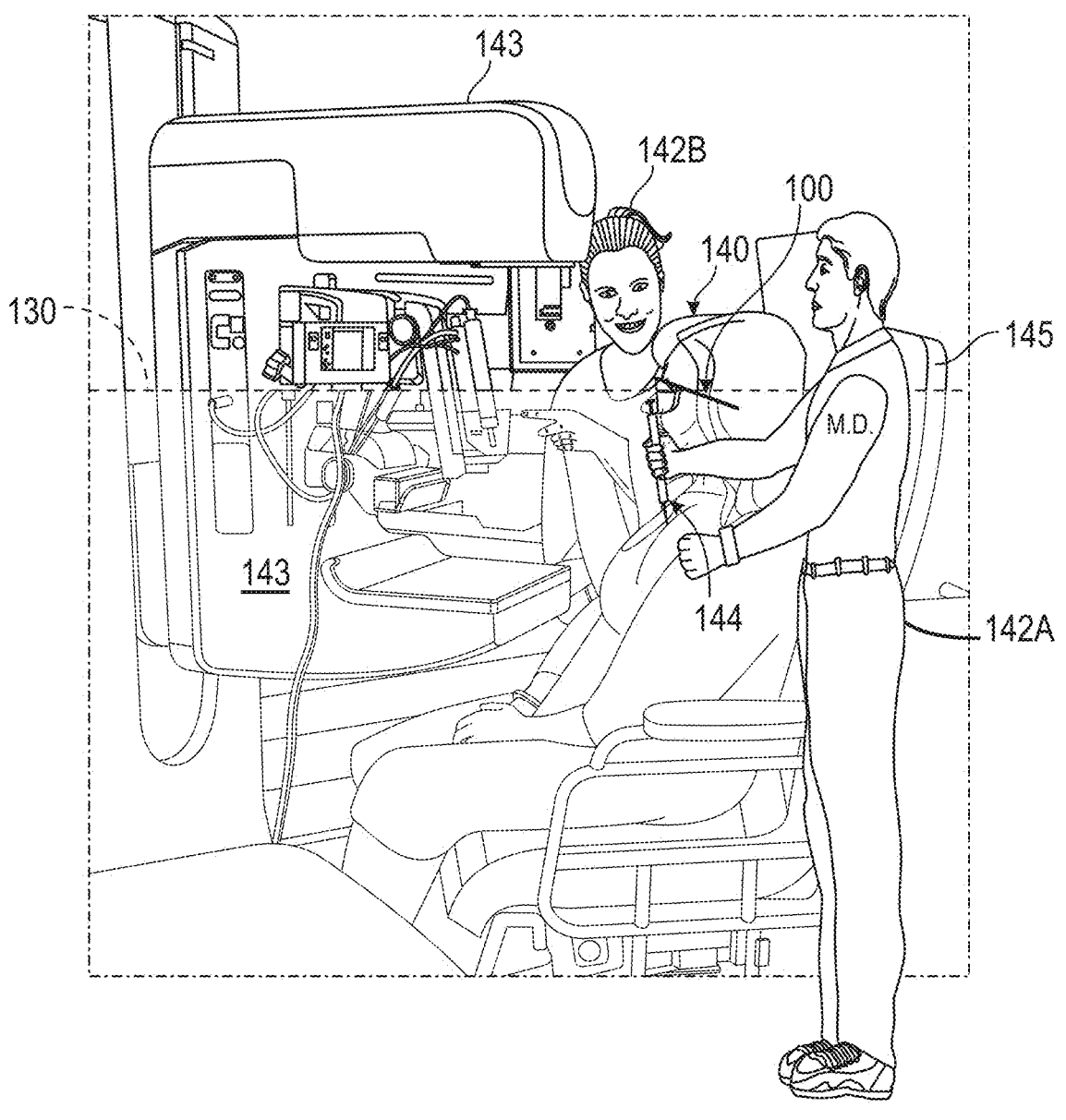
Figure 19A:
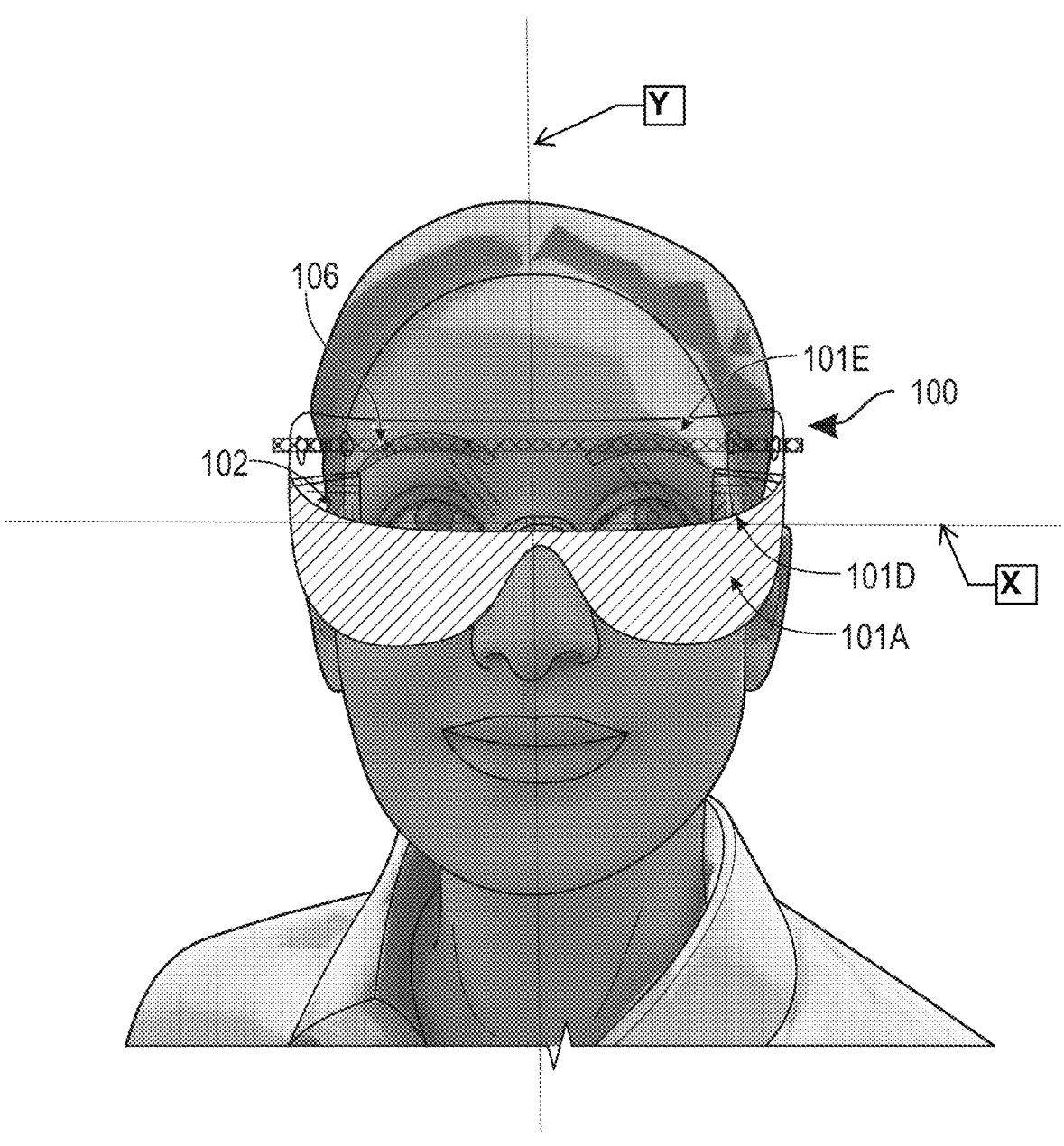
Figures 19B, 19C, 19D:
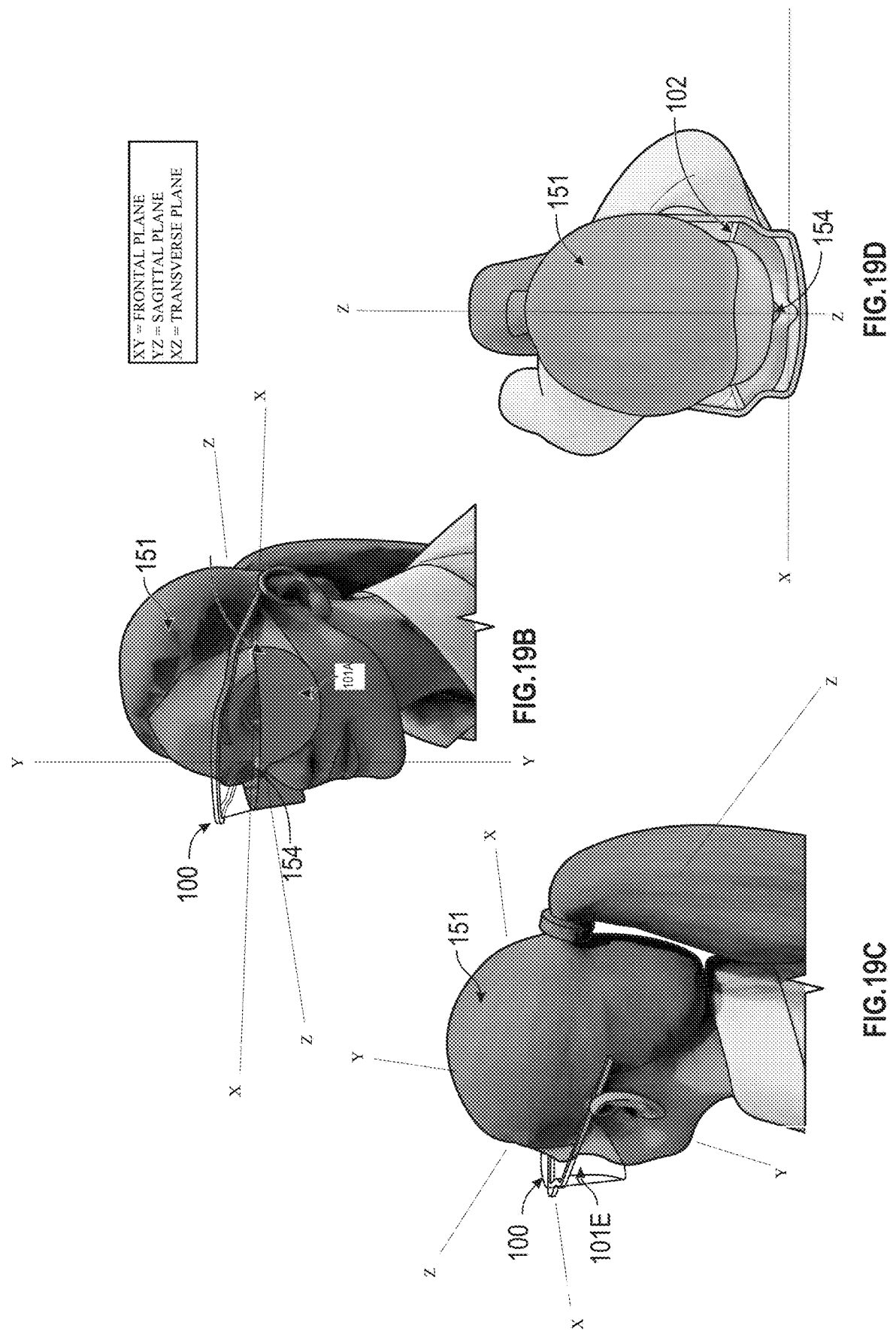
Figure 20A:
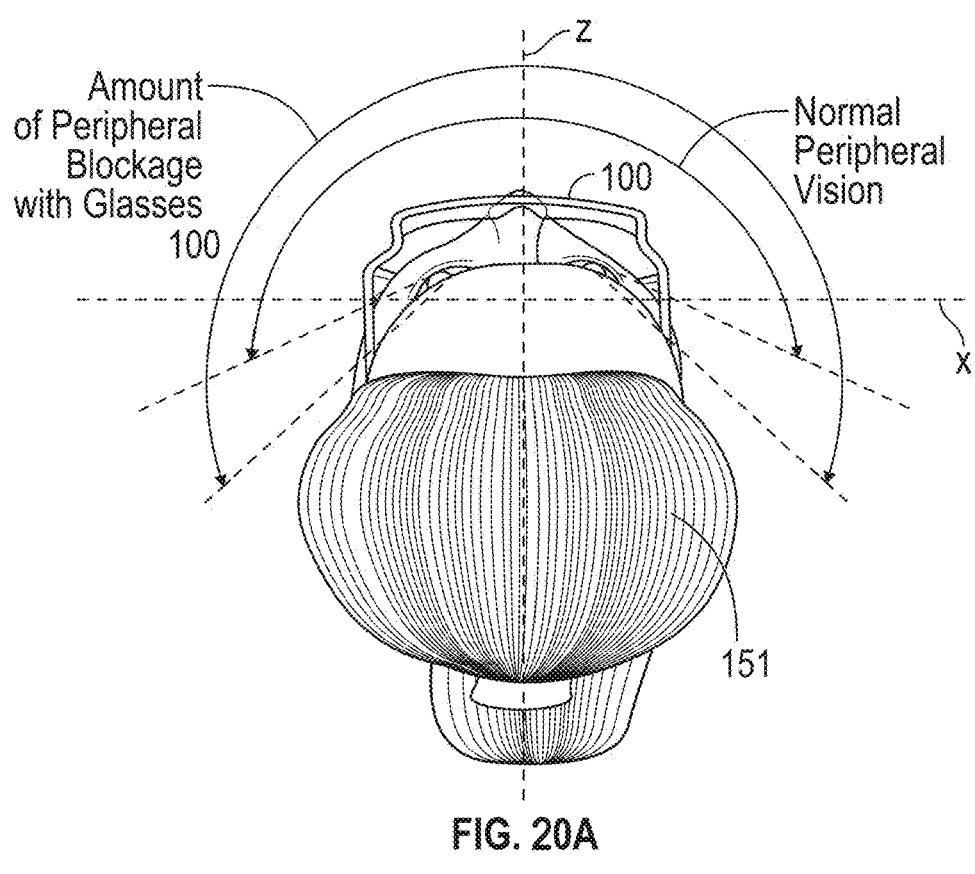
Figure 20B:
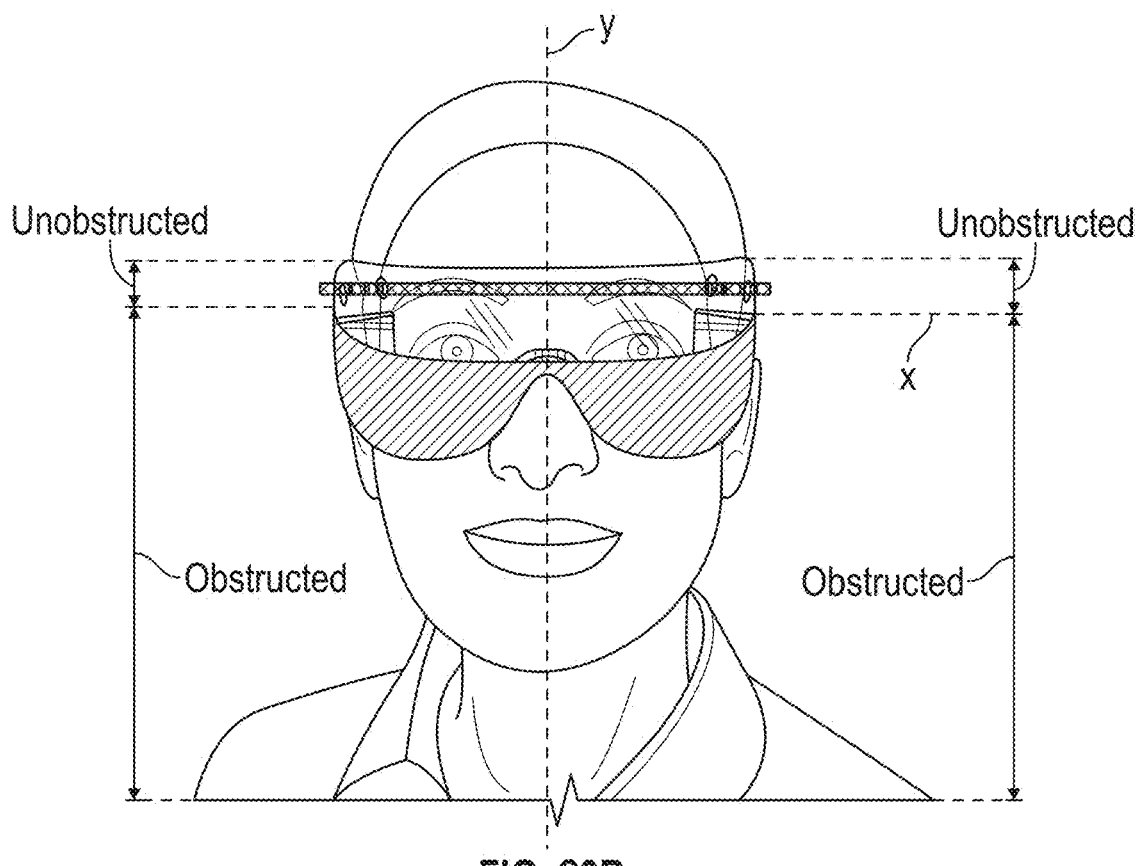

FIG. 18A—Upright Biopsy Procedure

Depicts diagrammatically effective visual blockage of patient's field of view during an Upright Biopsy Procedure on a patient, and illustrating diagrammatically a procedure apparatus including an invasive biopsy tool and related medical equipment, the first clinician conducting the biopsy at a procedural region of the patient (here, the patient's breast), and a second clinician attending to the patient during the medical procedure in relation to the effectively blocked patient field of view of at least the procedural region and the biopsy tool according to one or more aspects of the invention.

FIG. 18B—Method of Making

Depicts by flow chart a non-limiting exemplary method or process of making an eyewear device according to one or more aspects of the present disclosure.

FIG. 18C—Method of Treatment

Depicts by flow chart a non-limiting exemplary method or process of conducting a medical procedure or treatment on a patient according to one or more aspects of the present disclosure.

FIGS. 19A-D

Depicts an exemplary embodiment of a wearable device according to one or more aspects of the invention as installed on a wearer of the wearable device, showing the installed device from different viewing angles with superposed XYZ axes indicating frontal, sagittal, and transverse planes relevant to the eyewear devices and methods utilizing one or more aspects of the present disclosure.

FIGS. 20A-B

Depicts the installed device of FIGS. 19A-D with diagrammatical annotations added illustrating the effective blockage of field of view by the installed embodiment of the device relative to the wearer of the device to provide obstructed and unobstructed partial fields of view for the patient.

FIG. 21A

A perspective view of one exemplary embodiment according to one or more aspects of the present invention diagrammatically effective field of view blocking forward and peripherally according to one or more aspects of the invention on a patient wearing a device according to one or more aspects of the invention.

FIG. 21B

A perspective view of the exemplary embodiment of FIG. 16A from a different viewing angle.

FIG. 22

Front elevational view of the embodiment of FIG. 16A.

FIG. 23

Back elevational view of the embodiment of FIG. 16A.

FIG. 24

Top plan view of the embodiment of FIG. 16A.

FIG. 25

Bottom plan view of the embodiment of FIG. 16A.

FIG. 26

Side view of the embodiment of FIG. 16A.

FIG. 27

Opposite side view of the embodiment of FIG. 16A.

FIG. 28A

A perspective view of one exemplary embodiment according to one or more aspects of the present invention, including aesthetic design.

FIG. 28B

Figure 28A:
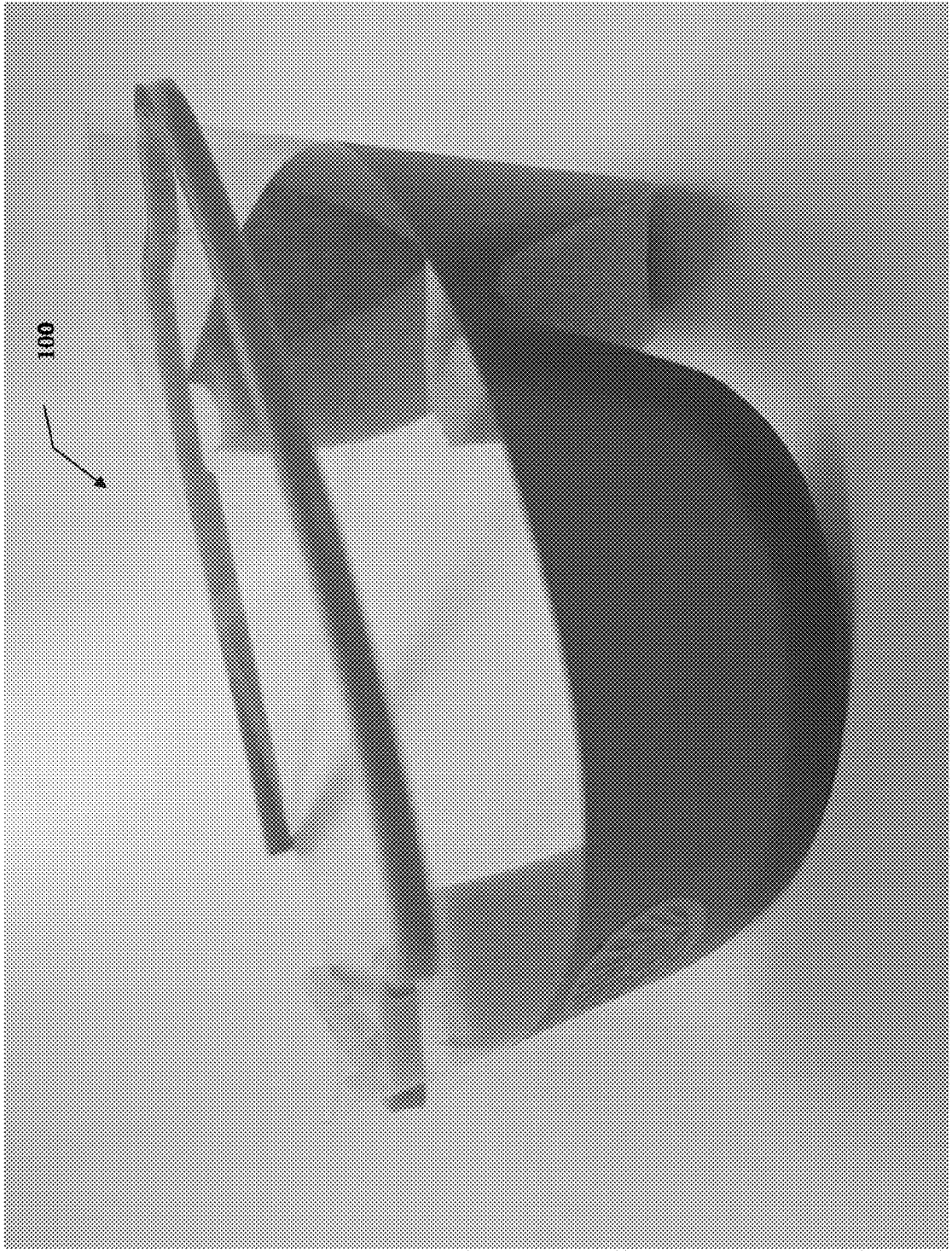

A perspective view of the exemplary embodiment of FIG. 28A from a different viewing angle.

FIG. 29

Front elevational view of the embodiment of FIG. 28A.

FIG. 30

Back elevational view of the embodiment of FIG. 28A.

FIG. 31

Top plan view of the embodiment of FIG. 28A.

FIG. 32

Bottom plan view of the embodiment of FIG. 28A.

FIG. 33

Side view of the embodiment of FIG. 28A.

FIG. 34

Opposite side view of the embodiment of FIG. 28A.

FIGS. 35A-E

Views illustrating aspects of one non-limiting method of making/assembling an exemplary embodiment of an eyewear devices according to one or more aspects of the present.

DETAILED DESCRIPTION OF EXEMPLARY EMBODIMENTS ACCORDING TO ONE OR MORE ASPECTS OF THE INVENTION

FIG. 1—Perspective—Procedure Setup Without Eyewear

Depicts a patient (140 positioned for a vascular access or interventional procedure, shown without the application of the vision-restricting eyewear apparatus. The clinician 142 is positioned adjacent to the subject in preparation for performing the procedure. The procedural region 141, located below the subject's horizontal line of sight 130, remains fully visible. This area 141 includes any portion of the body likely to be accessed for the procedure and represents the region where visual stimuli may trigger discomfort, anxiety, or physiological distress.

The example procedural apparatus 143 is shown for illustrative purposes only. It provides patient support, imaging guidance, and instrument positioning for conducting the procedure. The subject's lower visual field remains unobstructed in this baseline configuration, highlighting the contrast with later figures in which the vision-restricting apparatus is in place. It also illustrates the entire field of view of the patient along viewing direction 130 is unobstructed, including direct view of the patient's own frontal plane anatomy (including the procedural area 141 on the patient where the procedure will be performed), the procedural equipment 143 used during the procedure, and attending clinician(s) 142.

FIG. 2—Perspective—Application of Eyewear Apparatus

Depicts a clinician 142 applying the vision-restricting apparatus 100 to a subject 140 positioned for a medical procedure. The procedural region 141 lies within the subject's lower field of vision. The application of the apparatus represents a method step in which the subject's view of the procedural region is partially obstructed. A zone of visual obstruction 133 is created, blocking visibility below a forward gaze 130 while preserving some forward or ambient awareness (e.g., outside blocked field of view 133).

This visual obstruction does not begin at the forward gaze line 130, but rather begins below it, allowing for a natural and comfortable field of vision while eliminating exposure to potential procedural triggers. The procedural setup includes an example non-limiting procedural apparatus 143 shown for context and example only. In this example, patient 140 is supported, positioned, and oriented in an upright (inclined and not supine) sitting posture and, as a result, the shown example of partial field of view blockage generally downward is engineered to effectively block any chance of patient view of the procedure area 141 on the patient when the patient remains in the appropriate position shown in FIG. 2, but also if the patient turns his/her head in other directions. Thus, the embodiment is engineered to effectively block when the patient stays in the appropriate position and orientation, but also for head movements away from the same. A variety of possible procedures or treatments are relevant, whether or not they include just a tool (e.g., needle or the like) or a machine, or both.

FIG. 3—Perspective—Procedure Performed with Eyewear in Place

Depicts a subject 140 undergoing a vascular access or interventional procedure with the vision-restricting apparatus 100 in place. The clinician 142 is actively engaged with the procedural region 141, while the subject's lower visual field is obstructed by the apparatus.

A zone of visual obstruction 133 is present below the subject's forward gaze 130, fully blocking visibility of the procedural region. The subject's awareness of their surroundings is preserved above the blocked field, allowing for comfort and orientation without visual exposure to the procedure itself.

The example procedural apparatus 143 remains visible for contextual reference, but is not a required element of the claimed invention. This figure illustrates the method step of performing the procedure while the vision-restricting apparatus remains in place. In some examples (see also FIG. 18A), the procedure can involve a needle-based tool 144 for invasive biopsy, venous or arterial access for drawing blood, giving blood, or receiving blood, catheter insertion, infusion, irrigation, suction, or other medical processes or treatments that use a tool to interface with patient anatomy either invasively or not. In this example, body 152 of patient 140 is supported with torso and head 151 in an upright position in chair 145. In some examples, the procedure can include a tool hooked up to ancillary or affiliated components or equipment, or use other tools and/or equipment. Non-limited examples include aspiration, laparoscopic, camera insertion, infusion, irrigation, suction, or other. Some non-limiting examples of such equipment can include monitors, displays, meters, or readouts.

FIG. 4—Diagram—Goldmann Visual Field Obstruction Limits

Depicts a Goldmann-style visual field chart centered on the subject's gaze. The horizontal meridian 130 represents the left-to-right axis of forward gaze, dividing the superior visual field 131 from the inferior visual field 132.

The blocked or visually obstructed region 133 represents the minimum fully obstructed portion of the subject's visual field required by the claimed method and apparatus. This region begins at a lower limit 136 and extends downward toward the bottom of the visual field.

The top boundary of the opaque lower region 134 may be positioned anywhere within a defined vertical range that spans from an upper limit 135, located 45 degrees superior to the horizontal meridian, to a lower limit 136, located 45 degrees inferior. The position of this boundary varies between embodiments but must always be selected such that the fully obstructed region 133 is present.

The upper transparent or visually unobstructed region 137 lies above the top boundary and remains visible to the subject in all embodiments, allowing for partial forward gaze or ambient visual awareness.

This figure supports the embodiment by illustrating how visual obstruction is delivered consistently to a specific portion of the inferior field, while allowing flexibility in where that obstruction begins, and preserving visibility above for user orientation and comfort.

FIG. 5—Section—Visual Field Obstruction Caused by Apparatus

Depicts a vertical section through the subject's 140 visual field while wearing the vision-restricting apparatus 100. The horizontal meridian 130 represents the subject's forward gaze axis, dividing the superior visual field 131 from the inferior visual field 132.

The blocked region 133 represents the minimum fully obstructed portion of the subject's visual field required by the claimed method. This region begins at a lower limit 136 and extends downward toward the bottom of the visual field.

The lower opaque region of the apparatus 101 begins at a top boundary 134 and extends downward toward the lower field of vision. The top boundary may be placed within a vertical range defined by an upper limit 135 (approximately 45° superior) and a lower limit 136 (approximately 45° inferior), depending on the embodiment.

The apparatus 100 includes a lower opaque region 101 responsible for creating the visual obstruction, and a foam interface 102 that conforms to the user's face to maintain continuous contact and prevent gaps. The upper transparent or unobstructed region 137 remains visible to the subject in all embodiments.

This figure demonstrates how the claimed apparatus physically generates the blocked visual field region 133, supports the claim scope for partial inferior visual field obstruction, and emphasizes the apparatus components responsible for producing the visual obstruction depicted in FIG. 4.

FIG. 6—Perspective—Cone of Blocked Lower Visual Field

Depicts the vision-restricting apparatus 100 in a perspective view as it would appear relative to the subject's face and visual field. The horizontal meridian 130 represents the wearer's forward gaze axis. Dashed lines 136 extend downward from the eye to indicate the upper angular extent of the claimed visual obstruction, which begins at a top boundary located between 45 degrees inferior and continues through 90 degrees inferior- or to the lower limit of the subject's visual field.

The opaque lower region 101 of the apparatus is positioned to fully obstruct this inferior region when worn. The foam interface 102 conforms to the user's face, ensuring a continuous seal and uninterrupted blockage throughout the obstructed zone.

This figure illustrates the spatial volume of visual obstruction produced by the apparatus, reinforcing the claim that the inferior field between 45° and 90° below the horizontal meridian is completely blocked in all embodiments, while the field above the top boundary remains visible.

FIG. 7—Perspective View of Eyewear Apparatus in Use

Depicts the vision-restricting apparatus 100 including an opaque lower region 101 and a foam interface 102. The apparatus is shown adjacent to a subject 140 for illustrative purposes only.

In this embodiment, the opaque lower region 101 is configured as part of a lens or shield structure intended to obstruct visual stimuli from the lower field of vision. The foam interface 102 is positioned along the rear surface of the opaque region and is composed of a compressible material configured to deform adaptively under pressure. This material enables the apparatus to conform to variable adjacent surfaces, allowing it to form a continuous optical seal even across curved or irregular topographies.

The conforming properties of the foam interface represent a functional enhancement over rigid designs by supporting a reliable visual barrier across diverse surface geometries without requiring fixed alignment or rigid structural fit.

This figure illustrates one example of structural arrangement of components that form an embodiment according to one or more aspects of the present disclosure, emphasizing how the interface contributes to continuous optical coverage independent of a specific user anatomy.

FIG. 8—Isometric View of Apparatus with Flexible Lens Wrapping Around Contour Depicts the vision-restricting apparatus 100 including an opaque lower region 101 and a foam interface 102, shown adjacent to a subject 140 for illustrative purposes. In this embodiment, the lens is formed from a flexible material, allowing it to deform and wrap around contoured surfaces, such as those near the nasal bridge and cheek, while maintaining continuous coverage.

Label 101I identifies a flexure capacity, where the lens bends to follow the shape of an adjacent surface. The foam interface 102 maintains optical coverage by conforming along the inner surface. The apparatus in this embodiment achieves visual obstruction through its flexible lens geometry and surface engagement, though additional structural elements such as adhesives or frame supports may be present in other configurations.

The subject 140 is for illustrative purposes and can, of course, have a variety of facial and head form factors.

FIG. 9—Embodiments of Foam Interface Against Contoured Surface

Depicts a magnified view of the vision-restricting apparatus 100 focused on the central nasal interface. The apparatus includes an opaque lower region 101 and a transparent or at least substantially unobstructed upper region 103, together forming a continuous shield or lens structure. Along the rear surface, a compressible foam interface 102 is configured to form a continuous visual barrier when applied to an adjacent surface.

In this embodiment, the foam interface comprises a left U-cup segment 102A and a right U-cup segment 102B, each curving inward toward a central bridge notch 102C. This central relief zone accommodates geometric variation and enables the two foam segments to flex and converge while maintaining full contact along the apparatus base.

The design includes inner folded surfaces 102D on both 102A and 102B for vertical compression along central contours, and outer folded surfaces 102E on both 102A and 102B for lateral expansion and coverage across broader edge regions. Optional adhesive backing or other adhesive material 105 may be applied to skin-facing surfaces of 102 to promote better effective blocking of vision to better secure the device 100 to the skin of patient 140 and, thus, promote continuous and complete vision blockage including at any possible gaps between device 100 and the patient's face. Suggested inward conforming forces 102F and surface contact zones 102G may be shown to represent the natural deformation and contact behavior of the foam when applied.

This figure supports the apparatus claims by demonstrating how the dual foam segments create a continuous, adaptable barrier beneath the visual field, ensuring consistent obstruction without gaps and allowing for structural flexibility across multiple configurations.

FIG. 9a—Foam Embodiment—High Compression

Illustrates a high-compression state of the foam interface 102, wherein opposing inward forces 102F act upon the edges of the foam segments 102B. This compression causes the foam to fold along the outer surface 102E about a contour line 102H, resulting in the outer surface 102E becoming the sole contact area against the user's skin. The foam segments collapse onto themselves, creating a continuous, gapless barrier while enhancing conformity to more prominent facial contours.

FIG. 9b—Foam Embodiment—Low Compression

Illustrates a low-compression configuration of the foam interface 102. In this embodiment, the foam segments 102B retain much of their original shape, relying primarily on foam compression to create sealing contact along surface contact zones 102G. Limited inward folding occurs only near the nasal bridge region where inner surfaces 102D partially collapse, resulting in the inner surface 102D becoming the primary contact area against the user's skin. This embodiment is particularly effective for users with smaller nasal ridges or narrower profiles, maintaining comfort while preserving visual obstruction.

FIG. 10—Isometric View of Apparatus Embodiment with Transparent Upper Lens and Frame Presents an isometric view of an assembled embodiment of the vision-restricting apparatus 100, illustrating the relationship between the lens structure, foam interface, and frame.

The lens includes two functional regions: an opaque lower region 101, which obstructs the inferior visual field, and an upper transparent polymeric region 101E, which remains optically clear to preserve forward and upward visibility. These zones may be formed within a single polymeric lens body, with the lower region treated or pigmented for opacity and the upper region left untreated.

The foam interface 102 is affixed to the inner surface of the lens to maintain visual blockage through conforming surface contact. Though shown as a continuous part in this figure, the foam may consist of bilateral U-cup segments as described in prior embodiments.

The frame assembly 106 is coupled to the upper edge of the lens structure, providing retention around the head. The frame is shaped to support the lens without obstructing the upper transparent region and may be semi-flexible to accommodate different surface contours.

This figure demonstrates a fully assembled apparatus designed to block the inferior visual field while preserving ambient awareness through a transparent upper lens region.

FIG. 11—Exploded Isometric View of Vision—Restricting Apparatus Components provides an exploded isometric view of a representative embodiment of the vision-restricting apparatus 100, showing the distinct component layers and their relative positions prior to assembly.

The frame assembly 106 is shown at the top of the exploded stack and comprises a flexible frame body 106A designed to bend or flex around a contoured surface. Integrated into the frame are lens retention mechanisms 106B, which engage with mounting apertures in the lens to hold the structure in place without the need for adhesives (which can make manufacturing/assembly quicker and cheaper). Adhesives, or other fastening techniques, might be used alternatively or in addition to the mounting apertures.

Beneath the frame is the foam interface 102, which includes a left U-cup segment 102A and a right U-cup segment 102B. These foam pads are compressible and configured to form a continuous visual barrier by conforming to adjacent surfaces. Each foam segment is secured to the lens through a corresponding adhesive cup segment— left 104A and right 104B—which together form the adhesion interface zone 104. This zone ensures that the foam remains affixed during assembly and use.

The lens structure 101 is composed of multiple integrated layers, each contributing to optical performance and structural support:

The opaque film layer 101A represents a surface-applied obstruction zone made from vinyl or printed ink.

The polymeric lens substrate 101B forms the structural base of the lens, typically made from clear thermoplastic such as polycarbonate or PETG.

Mounting apertures 101C are formed in the lens substrate to allow coupling with the frame retention mechanisms 106B.

The integral coloration zone 101D represents an alternative or supplemental obstruction method, in which the polymeric lens is pigmented during manufacturing to create a permanent opaque region.

Finally, the upper transparent polymeric region 101E remains optically clear, preserving forward and upward visibility to maintain spatial orientation and ambient awareness.

This layered assembly enables the apparatus to fully obstruct the inferior visual field while providing structured support and flexible integration of surface-conforming components.

FIG. 12—Isometric View of Split-Lens Embodiment with Tensile Strap Frame

Illustrates an isometric view of a fully assembled split-lens embodiment of the vision-restricting apparatus 100. In this configuration, the apparatus comprises two discrete opaque lens segments 101, each configured to block the inferior visual field of one eye.

The interior-facing surface of each lens is affixed to a portion of the foam interface 102.

The foam segments conform to adjacent surfaces and support continuous visual obstruction by maintaining secure contact during wear. Although shown here as an integrated structure, the foam may correspond to left and right U-cup segments as described in prior figures.

The apparatus is held in place by a tensile strap frame 106, which encircles the user's head or cars to maintain positioning without the need for a rigid structural chassis. This flexible frame can be made from elastic or tensioned material, allowing the apparatus to adapt to varying head shapes and sizes while applying enough force to keep the lens components in proper alignment.

This figure demonstrates a minimal, conformable embodiment in which visual obstruction is achieved through the combined action of separate lens segments, adhesive or mechanical foam fixation, and a flexible strap-based retention system. The visual obstruction is related to patient anatomy (patient procedure area 141) involved with a specific medical procedure or treatment, or more generally to any procedure or treatment that involves a procedure area 141 below a transverse plane through the eye level of a patient. The engineering of the specific blocked field of view 133 can be informed by the foregoing. As a general matter, an effectively blocked field of view 133 angling downwardly and outwardly forwardly and peripherally from at or just below patient eye level should block patient view of his/her anatomy below eye level and, thus, may allow such an embodiment of 100 to be useful for many, most, and maybe all, anatomical procedures below the head, at least when the patient is positioned, postured, and oriented in an inclined and not supine or prone position.

FIG. 13—Exploded Isometric View of Split-Lens Embodiment

Depicts an exploded isometric view of a split-lens embodiment of the vision-restricting apparatus 100, in which each eye is shielded independently by a separate lens segment. This design supports flexible placement and minimized structure while preserving inferior field blockage.

The frame assembly 106 consists of a flexible tension chord 106C, which may be elastic or adjustable, and is configured to wrap around the user's head or cars. The tension chord is optionally terminated with end coupling mechanisms 106B that assist in anchoring the structure to the lens, foam, or both. Indicated diagrammatically in FIG. 13, mechanisms 106B can take any of a variety of forms and techniques to tie together the components into a final assembled device 100. Mechanisms 106B could include hardware such as buttons, rivets, caps, beads, or other structures that allow the opposite ends of tension chord 106C to be threaded through appropriate apertures in the components and then terminated to prevent chord 106C from backing out. But 106B could also include adhesives, knots, or other techniques of tying off or terminating a chord to prevent it from separating from or passing through an aperture in the lens or frame of the eyewear.

The foam interface 102 includes a left U-cup segment 102A and a right U-cup segment 102B, each designed to provide conforming surface contact around the lower and lateral facial contours. These foam elements ensure consistent visual obstruction through passive deformation against the surface.

Each foam segment is secured to the corresponding lens segment via an adhesive interface zone 104. The left adhesive cup 104A and right adhesive cup 104B may include conventional pressure-sensitive adhesive, but are not limited to permanent solutions. The structure allows for alternative affixation methods, including hook-and-loop systems (e.g., Velcro®), removable bonding agents, or other flexible attachment strategies.

The apparatus includes a split-lens system 101 with a left opaque lens segment 101F and right opaque lens segment 101G. Each lens segment is configured to individually obstruct the inferior visual field of one eye, forming a bilateral visual occlusion zone when worn. The use of separate lens units permits greater flexibility in frame tensioning, positioning, and surface adaptation across variable head geometries. As will be appreciated by those skilled in the art, nose bridge 106D could take different forms and embodiments, and can be connected to (or integrated with) other pieces of device 100 in a variety of ways. If a wire, 106D could operatively connect to 101F and 101G through through-holes like chord 106C (and terminated similarly). Alternatively, it might be fixed in place with adhesive or other fastening techniques.

This figure demonstrates an alternate embodiment where the inferior field obstruction is achieved through split-lens geometry and a tension-based retention system.
FIG. 14—Isometric View of Rigid Frame Embodiment with Opaque Lower Shield and Foam Provides an isometric view of a rigid frame embodiment of the vision-restricting apparatus 100. In this configuration, the lower visual field obstruction and frame structure arc unified into a rigid visor body 101H.

The rigid visor body 101H may be injection molded or thermoformed from a single material-such as polycarbonate or another structural thermoplastic. This unit combines both the lower opaque visual-blocking region and the lateral arms or temple extensions typically associated with eyewear. Its geometry resembles conventional wraparound safety glasses but is configured specifically to obstruct the inferior field of view.

Affixed to the inner surface of the visor body is a foam interface 102, positioned along the lower inner edge. This foam provides surface contact to maintain the visual obstruction and may also contribute to user comfort. The foam may be bonded with pressure-sensitive adhesive, a molded groove interface, or alternative attachment methods.

This embodiment eliminates the need for a separate frame or lens coupling system by integrating all structural and optical-blocking features into a single rigid body. It provides a streamlined design suitable for mass production and repeatable positioning.
FIG. 15—Isometric View of Rigid Visor Embodiment with Integrated Frame and Lens Shows an isometric view of an alternative embodiment of the vision-restricting apparatus 100, featuring a monolithic or rigid-body configuration. In this embodiment, the lower lens region and frame structure are combined into a single integrated unit labeled 101H.

The rigid visor body 101H is formed from a continuous material—such as polycarbonate or another molded polymer—and serves the dual function of obstructing the lower visual field and structurally supporting the device during use. The geometry of the visor may include curvature to wrap around the facial surface, while its upper portion functions as a built-in frame.

A foam interface 102 is affixed to the interior surface of the visor body. This foam element provides conforming contact with adjacent surfaces to maintain optical coverage and may be segmented into left and right portions or formed as a continuous pad.

This embodiment simplifies the assembly by eliminating the need for a separate frame component 106, relying instead on the rigidity and form of the visor body 101H to maintain shape, fit, and optical obstruction in a single structural unit.
Full Label Descriptions
Lens and Optical Components An eyewear apparatus configured to obstruct the lower visual field, comprising a lower opaque lens and contact interface.

Opaque Lower Region of Lens. The portion of the lens or shield that is non-transparent and configured to block visibility in the lower visual field.

(101B)—Polymeric Lens Substrate. The structural lens body formed from optically clear thermoplastic (e.g., polycarbonate or PETG) which provides mechanical support and flexibility.

(101C)—Mounting Apertures. Pre-formed holes or notches in the lens substrate 101B used for mechanical coupling to the frame 106B.

(101D)—Integral Coloration Zone of Polymeric Lens. A pigmented or dyed portion of the lens substrate itself, where opacity is built into the base material to achieve visual obstruction without requiring an affixed film.

(101E)—Upper Transparent Polymeric Region. A portion of the polymeric lens substrate 101B that remains optically clear and unobstructed, configured to preserve forward and upward visibility during use. This region maintains ambient awareness, allows for verbal and non-verbal interaction with medical staff, and helps reduce disorientation by preserving spatial orientation above the horizontal meridian.

(101F)—Opaque Left Lens Segment. A first individual lens portion configured to obstruct the inferior field of the left eye.

(101G)—Opaque Right Lens Segment. A second individual lens portion configured to obstruct the inferior field of the right eye.

(101H)—Rigid Visor Body. A unified or monolithic structure that combines the lower opaque region 101 and the structural frame 106 into a single, rigid-body element. This visor-like body may be molded from a single material (e.g., tinted polycarbonate) and configured to serve both as the visual obstruction and the retention structure. Foam pads or other interface materials may be affixed to the interior surface.

(101I)—Flexible Opaque Lower Region. A deformable or pliable section of the lens structure configured to provide inferior field visual obstruction while conforming to curved or irregular surfaces. This region may be formed from a flexible material such as an opaque vinyl film or ink layer, applied or laminated to the underlying lens body. The flexible nature allows the obstruction layer to bend or wrap around adjacent surfaces, maintaining continuous optical coverage without requiring a rigid frame structure.

Foam Interface and Adhesion

Foam Interface (General). A compressible, non-rigid element affixed to the inner surface of the apparatus and configured to maintain optical obstruction by conforming to an adjacent surface.

(102A)—Foam Pad-Left U-Cup Segment. A curved segment of the foam interface extending from the left side and configured to fold inward toward a central relief notch.

(102B)—Foam Pad-Right U-Cup Segment. A complementary curved foam segment on the right side, forming a dual structure with the left U-cup to maintain continuity across the nasal region.

(102C)—Bridge Notch/Nasal Relief Channel. A recessed gap or channel between the left and right foam segments, configured to accommodate geometric variation at a central surface contour (e.g., nose bridge).

(102D)—Inner Folded Surface of Foam Pad. The surface of each U-cup segment that bends inward to compress against vertical relief zones.

(102E)—Outer Folded Surface of Foam Pad. The outward-bending portion of each foam segment that wraps across broader surfaces such as the cheek or lower shield edge.

(102F)—Suggested Inward Force Direction Arrows. Diagrammatic indicators representing the passive deformation of the foam interface when pressed against a surface.

(102G)—Surface Contact Zones. A shaded region representing where the foam interface engages an adjacent surface to maintain optical blockage. As the foam conforms under compression, it effectively folds from one surface to another-such as from the outer surface at the nasal bridge, to the inner surface down the cheek, and back to the outer surface near the temple-forming a continuous, adaptable seal.

(102H)—Foam Transition Fold Line. A hinge-like axis or bend line along the foam interface where each U-cup segment transitions from the inner surface 102D to the outer surface 102E. This line represents the approximate zone of material flexure and directional change during compression.

(102I)—Inward Pressure Zone. A region of the foam on the outer surface 102E that applies directed pressure toward a central adjacent surface. This pressure contributes both to continuous visual occlusion and to mechanical stabilization of the apparatus during use.

(103) Substantially Unobstructed Region. A region that at least substantially is visually unobstructed (104)—Adhesion Interface Zone. A bonding region between the foam and the rear surface of the lens, facilitating affixation.

(104A)—Adhesive Cup Segment-Left. A discrete or patterned adhesive area securing the left foam segment 102A to the lens.

(104B)—Adhesive Cup Segment-Right. The corresponding right-side adhesive region securing foam segment 102B.

(105) Adhesive (optional). Medically or skin-safe adhesives can optionally be used on the skin-facing surfaces of foam interface 102 to assist in installation and retention of device 100 for effective blocking of a partial field of view of patient 140. Such adhesives are well-known by those skilled in the art and can be reversible adhesives, e.g., similar to used on Post-It® Notes or Band-Aids®.

Frame Assembly (106)—Frame Assembly. A structural component configured to support and retain the lens in position relative to the user's face. May be flexible or rigid depending on embodiment.

(106A)—Flexible Frame Body. A one-piece molded frame structure, typically made from a hypoallergenic plastic or polymer, capable of flexing slightly to conform to facial curvature and assist in comfort and placement.

(106B)—Lens Retention Mechanism. Integrated slots, tabs, or projections designed to receive and secure the mounting apertures 101C of the lens, allowing mechanical coupling without adhesives.

(106C)—Tension Chord. A flexible or elastic cord configured to wrap around the head or ear region to retain the lens elements in position during use.

(106D)—End Coupling Mechanisms (Optional). Terminations, hooks, or friction fits at the ends of the tension chord that optionally engage the lens or foam structure.

User Anatomy and Visual Field References (130)—Horizontal Meridian. The subject's left-to-right forward gaze axis dividing superior and inferior visual fields.

(131)—Superior Visual Field Region. The portion of the visual field above the horizontal meridian.

(132)—Inferior Visual Field Region. The portion of the visual field below the horizontal meridian.

(133) Minimum Fully Blocked Region. The portion of the inferior visual field that is claimed and completely obstructed in all embodiments.

(134)—Top Boundary of Blockage. The fixed starting point of the blocked region in a given embodiment.

(135)—Upper Limit for Top Boundary Placement. The highest permissible location for the top boundary (~45° superior).

(136)—Lower Limit for Top Boundary Placement. The lowest permissible location for the top boundary (~45° inferior).

(137)—Upper Transparent Region. The portion of the visual field above the top boundary 134 that remains visible to the subject.

Procedure/Environment References (for Method Diagrams)

(140)—Subject (Patient). A person undergoing a vascular access or interventional procedure.

(141)—Procedural Region. An area of the body located within the subject's lower visual field.

(142)—Clinician. A medical professional preparing to perform the procedure.

(143)—Example Procedural Apparatus. An illustrative system used to support and perform the medical procedure.

How It's Made: An Optimal Embodiment of an Apparatus of Eyewear for Blocking Lower Field of Vision The disposable eyewear according to at least some exemplary embodiments of the invention is crafted with a meticulous selection of materials and a precise manufacturing process to ensure optimal performance and comfort for medical professionals. The frame, made from durable plastic, is both robust and lightweight. This material choice ensures hypoallergenic properties as it is free from natural rubber latex. The frames are injection molded to achieve consistent dimensions and then colored during the molding process to provide a range of color options. Each frame undergoes a rigorous quality inspection to guarantee structural integrity and adherence to quality standards. Dersu, Inci et. al. Understanding Visual Fields, Part I; Goldmann Perimetry, January 2006, and June 2006, cited supra and incorporated by reference herein, and U.S. Pat. No. 10,702, 345 to Saito et al entitled "Surgical Face Guard, Surgical Frame, Surgical Polarization Shield, and Surgery System", incorporated by reference herein, describe lightweight plastic frames and lenses, as well as some ways to vary the opacity of portions of the lenses which teachings might be applicable to certain aspects or embodiments of the present invention. Lightweight, one-use, throw-away plastic frames and non-optical lenses are available commercially, including for medical procedures, and can form the starting point for eyewear according to aspects of the invention. It is to be appreciated that variations to the above are possible. The lenses of the eyewear according to at least some exemplary embodiments of the invention are made from optically clear polyester, chosen for its superior clarity and durability.

These lenses are formed into thin sheets, cut into the desired shapes, and have small holes punched into them to facilitate secure attachment to the frame. The lenses may also receive additional coatings to enhance durability, scratch resistance, and anti-fog properties. Each lens is meticulously inspected for optical clarity before the lower opaque section is applied. It is to be appreciated that variations to the above are possible. The lower opaque section is typically created using a vinyl sticker, which is cut to fit the lower section of the lens and carefully applied to ensure an even and bubble-free adhesion. Alternative methods for creating the opaque section could be applying a tinted coating during the lens manufacturing process, using non-toxic paint, or laminating a pre-cut opaque film onto the lower part of the lens. It is to be appreciated that variations to the above are possible. Comfort is a critical consideration, and a medical-grade polyurethane or similar soft foam is used for the foam pads. These pads are designed to provide cushioning where the eyewear contacts the face, enhancing user comfort. The foam is cut into the necessary shapes and has an adhesive backing applied for easy attachment during assembly. It is to be appreciated that variations to the above are possible. During the assembly process, the lenses are securely attached to the frames by aligning the holes in the lenses with the corresponding connectors on the frame. This method ensures a secure fit without the need for additional adhesives. The vinyl sticker or alternative opaque application is verified for proper alignment and adhesion. The foam pads are then attached to designated areas on the frame, ensuring they are securely placed and correctly aligned for maximum comfort. It is to be appreciated that variations to the above are possible. The final assembly stage involves cleaning and polishing the eyewear to remove any manufacturing residues and ensure clear visibility through the lenses. Each unit undergoes a final quality inspection to confirm the secure assembly of the frame and lenses, the correct application of the opaque section, and the proper attachment of the foam pads. This detailed and precise process ensures that the disposable embodiment of the eyewear provides reliability, comfort, and optimal performance for medical professionals during procedures.

Use During Upright Biopsy Procedure

The eyewear device 100 is specifically designed to enhance patient comfort and reduce anxiety during medical procedures, such as the Upright biopsy. Before the procedure begins, the medical staff explains the procedure to the patient and introduces the eyewear device, highlighting its purpose in blocking the view of the biopsy site to reduce anxiety and discomfort. The patient is then seated in the Upright biopsy chair, and the eyewear device is carefully positioned on the patient's face. The lower opaque section is aligned to block the lower field of vision, effectively obstructing the view of the medical procedure taking place. The continuous compressible pad is adjusted to conform to the contours of the patient's face, eliminating any gaps around the cheekbones, nose bridge, and temples, ensuring complete obstruction of the lower field of vision and providing a secure, comfortable fit. Once the patient is properly fitted with the eyewear, they are guided into the correct position in the Upright biopsy chair, with their head positioned to ensure they are looking forward and slightly upwards, minimizing the view of the biopsy area. The medical staff then proceeds with the biopsy, reassured that the patient's view of the procedure site is fully obstructed by the eyewear. This setup helps to reduce the patient's anxiety and potential for vasovagal responses. Throughout the procedure, the medical staff monitors the patient's comfort and adjusts the eyewear if needed to maintain optimal coverage and comfort. After the biopsy is completed, the eyewear device is gently removed. The patient is assisted in adjusting to normal vision and is given time to recover from the procedure. The medical staff seeks feedback from the patient on the comfort and effectiveness of the eyewear, which can be used to make any necessary adjustments for future use. Depending on whether the eyewear is reusable or disposable, it is either cleaned and sanitized according to medical hygiene standards or properly disposed of in accordance with medical waste protocols. For reusable eyewear, a thorough inspection is conducted to ensure all components, especially the compressible pad, remain in good condition for future use.

By blocking the patient's view of the biopsy site, the eyewear helps to reduce anxiety and discomfort, leading to a calmer and more cooperative patient. With the patient's anxiety reduced, the medical staff can perform the biopsy more efficiently and with fewer interruptions. The comfort and reassurance provided by the eyewear contribute to a more positive overall experience for the patient. This step-by-step guide ensures that the eyewear device is used effectively to enhance patient comfort and procedural efficiency during the Upright biopsy procedure. As mentioned previously, subtle but important benefits of the technical solution according to the invention when applied in medical application is that it promotes better patient experiences and outcomes. For example, sudden or unexpected patient movements during a sensitive medical procedure, including invasive procedure, are deterred to minimize risk of adversely affecting the effectiveness of any part of the procedure or the medical professional's application of the procedure on the patient. Another example is that adverse effects to the patient are deterred (e.g., vasovagal reaction or dangerously raised blood pressure or heart rate). Another example is better outcomes for the patient because the medical professionals have less risk of patient movement or anxiety delays or problems.

Other Use Cases

Medical Procedures: The eyewear device is particularly useful during medical procedures, as it prevents patients from seeing their body and the ongoing procedure, thereby reducing discomfort and anxiety.

Sports Training: The device can be employed in sports training, such as dribbling a basketball, to block the lower field of vision and enhance focus on upper body movements.

It can also be used in other sports to improve hand-eye coordination by limiting visual distractions from the lower field of vision.

Therapeutic Activities: In therapeutic settings, the eyewear can help users concentrate on specific tasks without visual distractions from their lower field of vision. This can be beneficial for individuals undergoing cognitive or physical therapy.

Educational Tools: The device can be used in educational environments to help students focus on visual tasks presented at eye level or above, minimizing distractions from their immediate surroundings.

Safety Applications: The device can be used in environments where it is crucial to block out distractions from the lower field of vision to ensure safety, such as during the operation of certain machinery or vehicles. Art and Creative Activities: Artists and creators can use the eyewear to focus on their work at eye level or above, reducing the influence of peripheral distractions and enhancing their creative process.

Options and Alternatives

The foregoing disclosures and descriptions are non-limiting examples of exemplary embodiments according to one or more aspects of the invention. The invention can take various forms and embodiments. For example, variations obvious to those skilled in the art will be included within the various aspects of the invention.

A unifying aspect of the present disclosure is restriction of wearer field of view by a wearable device removably mountable to the head of a user, where the restricted field of view is engineered to effectively partially block that field of view for a relevant application. Examples of relevant applications include medical interventions, procedures, or treatments on a patient's body below the level of the patient's eyes or below the patient's head. The wearable device has portion(s) that extend across the face at and below eye gaze direction when on the user. The field of view restriction can be by the device itself (vision obstruction by its form factor, structure, and materials), or by vision obstruction added to or integrated into an eyewear framework and eyeshield (e.g., strips or coatings), or a combination of the same.

As can be appreciated, this concept can be implemented in a variety of ways with a variety of techniques and structures. The exemplary embodiments are non-limiting examples of just some.

The restricted field of view obstruction can be a separate piece or pieces, an overlay, a film, a coloring, or other ways to effectively block vision.

The unobstructed vision can be light transmissive structure or open air (no structure).

The manner of removably mounting to a subject user can be like typical eye wear (e.g., frame with appropriate temple pieces and frontal plane eyeshield). The frame and eye shield can be separate pieces operatively connected or can be integrated together.

An interface with at least the subjects nose bridge, check bones, and temples can be configured to conform closely to these facial features of a user. This can be by the frame and eyeshield themselves, or by a frame and eyeshield (full or partial coverage of a subject's eyes) with added or integrated partial field of vision blockage. The partial field of vision blockage can include an interface between the frame and/or eyeshield and the user's facial antimony to promote "filling any gaps" between the frame/eyeshield and the user's face when installed on the user.

An example is a resilient and at least substantially effective vision blocking material like foam or rubber. Such materials can be low-cost, easy to shape and mount to the frame or eye shield, and promote the ability for the eyewear to be one-size fits all and effectively block the desired field of view for a range of face form factors, sizes, and shapes. Alternatively, the eyewear can be made in a set of different sizes/form factors, with each of the set engineered to better fit a particular facial size and form factor (similar to typical eyeglasses that have different frame sizes). As previously mentioned, some embodiments can be configured to effectively operably fit on a patient's head concurrently over the patient's optical eyewear.

To further help illustrate the possible variations of embodiments according to one or more aspects of the disclosure, reference is taken to FIGS. 16A-B, 17A-B, 18A-C, 19A-D, 20A-B, 21A-B to 27, 28A-B to 34, and 35A-E.

FIGS. 16A-B, 17A-B

A comparison of FIGS. 16A and 17A to FIGS. 16B and 17B help illustrate how embodiments of the disclosure can be engineered to partially block a relevant part of a subject's field of view. Taken in conjunction with other Figures in this disclosure that assign an XYZ axes with an origin at or near the nose bridge of a user, and the resulting XY frontal plane, XZ transverse plane, and YZ sagittal plane relative the wearer, by effectively blocking just a partial field of view at or near the patient's eyes, A variety of factors must be considered including what an unobstructed field of view is, what the end application for the disclosed eyewear and method is, and that blockage at or near the eyes has both an outsized effect of restriction of field of view away from the eyes, but also blockage at or near has challenges for completely or effectively blocking vision.

FIG. 18A

This diagrammatical illustration of one non-limiting medical procedure (e.g., breast biopsy), illustrates other challenges to effective management of patient field of view. They include not only where the procedure area is on the person's anatomy, the tools and equipment used and the clinician's involved, and the preferred or desired position, posture, and orientation of the patient during the procedure.

Such variables can result in variations on design of the solution of the present disclosure.

FIG. 18B

Variations in how the technical solution of the disclosure is designed, sourced, manufactured and assembled are, of course, possible. One example is method 200.

The designer must balance the various relevant factors, some of which are antagonistic to one another, to select materials effective for partial field of view blockage for a given end use application (step 202). A few non-limiting examples of materials are given in this disclosure. In one embodiment, the materials are cheap, readily available, and sufficiently durable for at least single use for the intended purpose. Plastics are a prime candidate, but others are possible.

The designer must balance factors involved with an eyewear configuration for an end use application. In one non-limiting example of a medical procedure or treatment on a patient's body, this can include consideration of the preferred or desired location and orientation of the patient during the procedure (step 204), as such must be evaluated relative to the normal field of view of the patient in that position and orientation versus the area on the patient's body that is involved in the procedure. For example, as in FIGS. 1-3 and FIG. 18A, the preferred or desired position and orientation is inclined in an upright sitting posture.

A design of the eyewear that functions according to need or desire is informed by the foregoing (step 206).

A manufacturing/assembly technique can be selected by the designer based on the foregoing. In one non-limiting example, plastic components can be economically mass produced and assembled by hand or machine, or a combination of both to produce a low-cost device. Any frame, eyeshield, and resilient gap-blocking components or portions can be mass produced, assembled, and packaged for an overall cost conducive to them being disposable after one-time use according to techniques well-known to those skilled in the art (step 208).

FIG. 18C

Variations in methods for the technical solution of the disclosure are, of course, possible. One example is method 220.

A patient for a medical procedure or treatment on his/her body would go through typical intake and initialization for a specific procedure or treatment (explanation and consent for the procedure by a clinician or staff) (step 222). This typically would include a best practices position and orientation of the patient. Again, in the non-limiting example of breast biopsy, this is upright and seated.

At the procedure/treatment location, the clinician(s) would typically use the best-practices patient positioning (step 224) and provide the patient with an eyewear device 100 designed for a restricted field of view relative to the area of the patient's body that is relevant to the procedure or treatment (step 226). The provided eyewear is installed on the patient (step 228).

The treatment or procedure is then conducted on the patient (step 230). The installed eyewear promotes effective blocking of patient vision of the procedure area on his/her body. The installed eyewear, according to design of the eyewear, can simultaneously provide at least substantially unobstructed field of view for the patient in a different direction. As discussed above, one example is in a direction that the patient can directly see at least one clinician during the procedure or treatment.

FIGS. 19A-D and FIGS. 20A-B

For one embodiment of eyewear 100, FIGS. 19A-D and FIGS. 20A-B (with annotations) help illustrate how they would restrict field of view when installed on a wearer relative to frontal plane XY, transverse plane XZ, and sagittal plane YZ. They also illustrate how this embodiment has eyeshields covering the wearer's eyes when installed, but with field of view blocking on lower frontal and peripheral portions of the eyeshields while simultaneously providing light transmissive top portions of the eyeshields to allow partial unobstructed field of view.

Figure 21A:
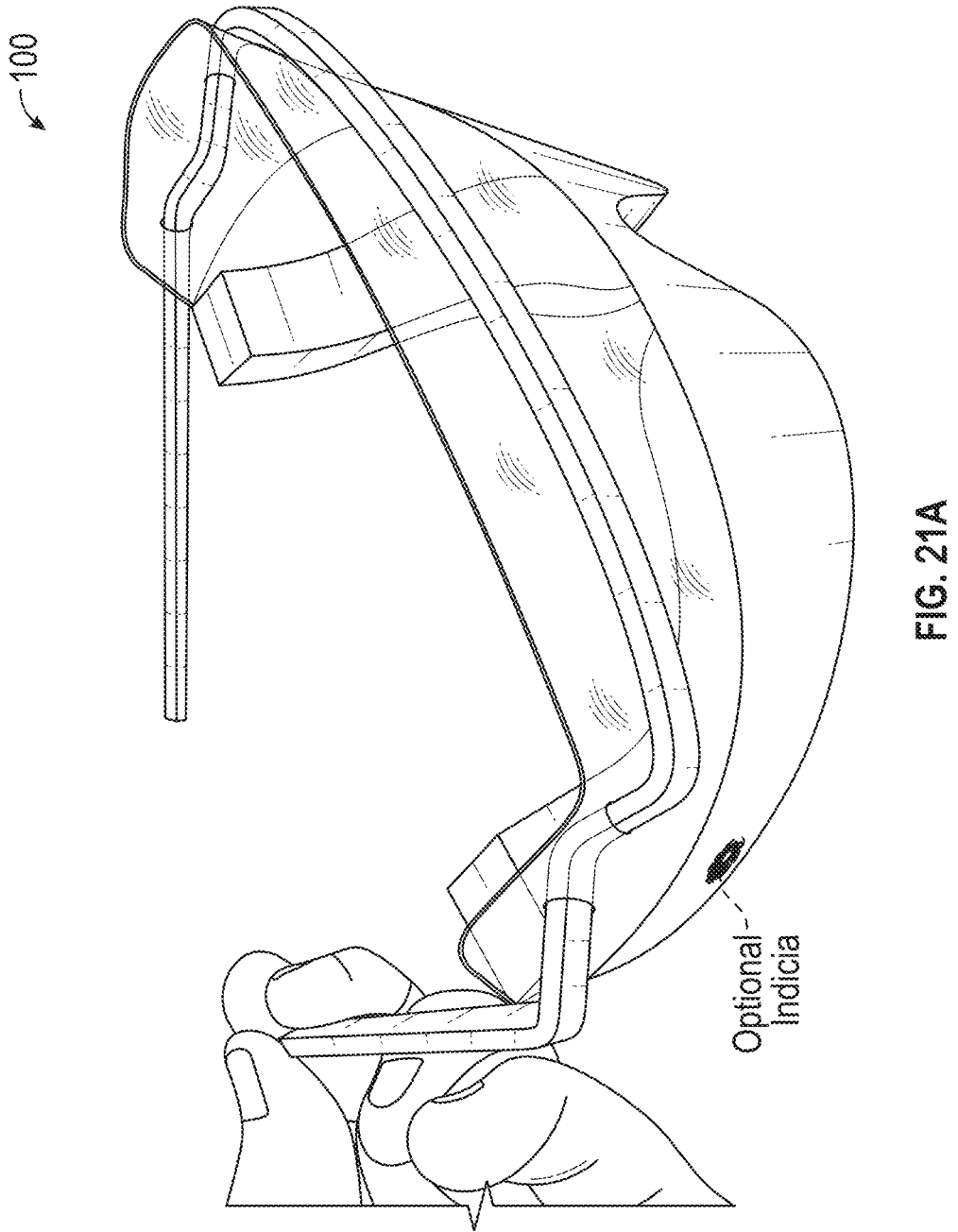
Figure 21B:
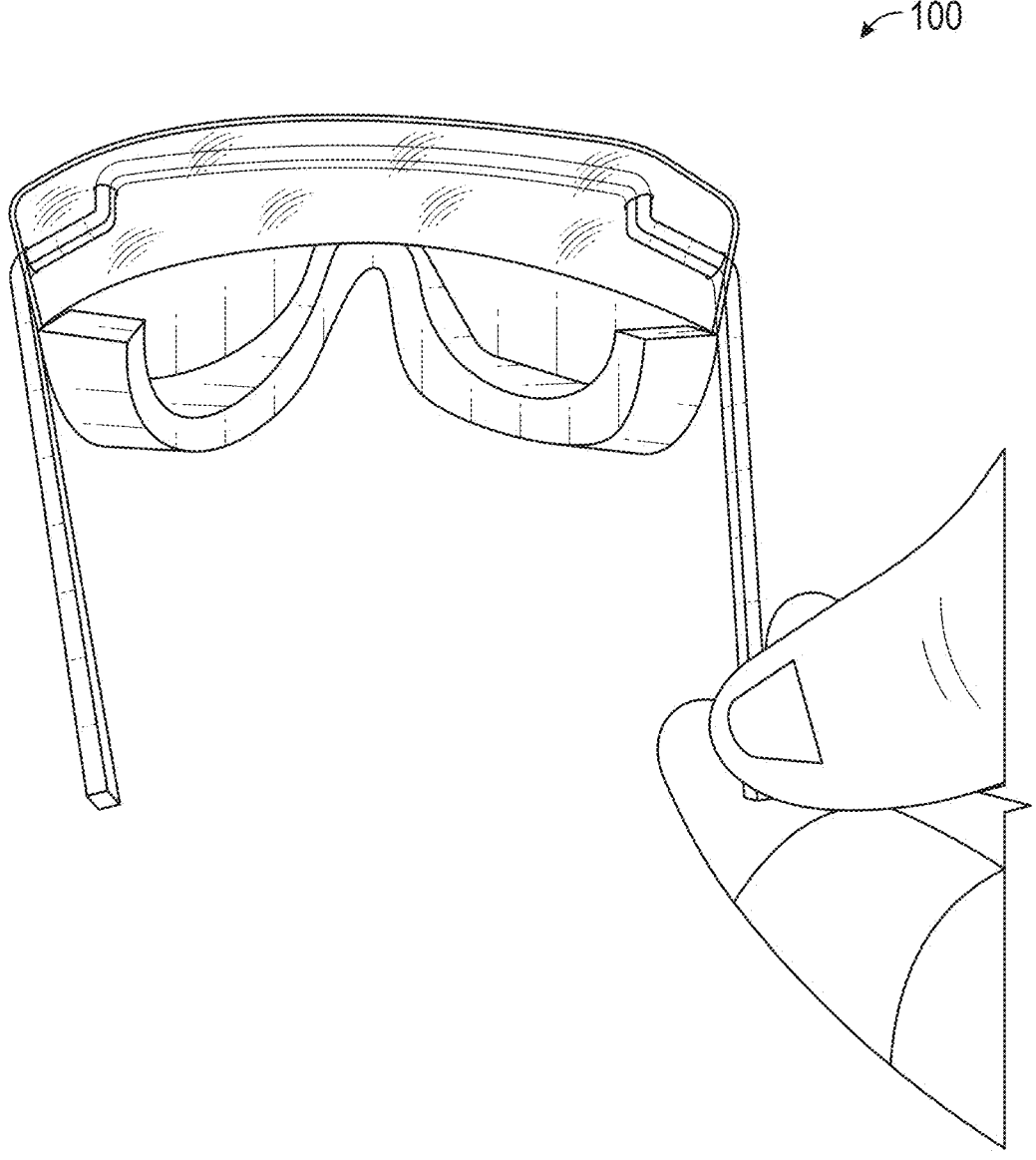
Figure 22:
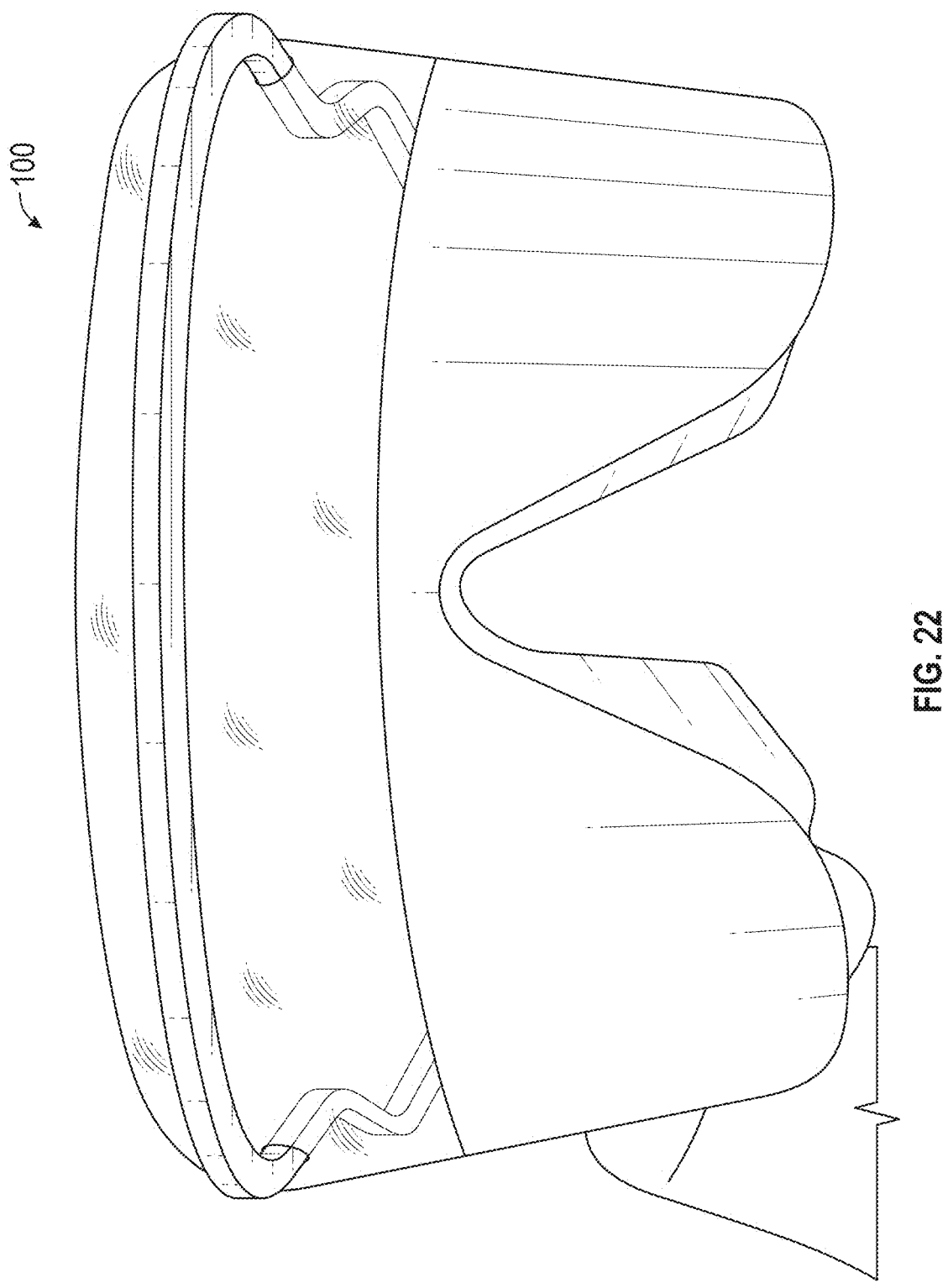
Figure 23:
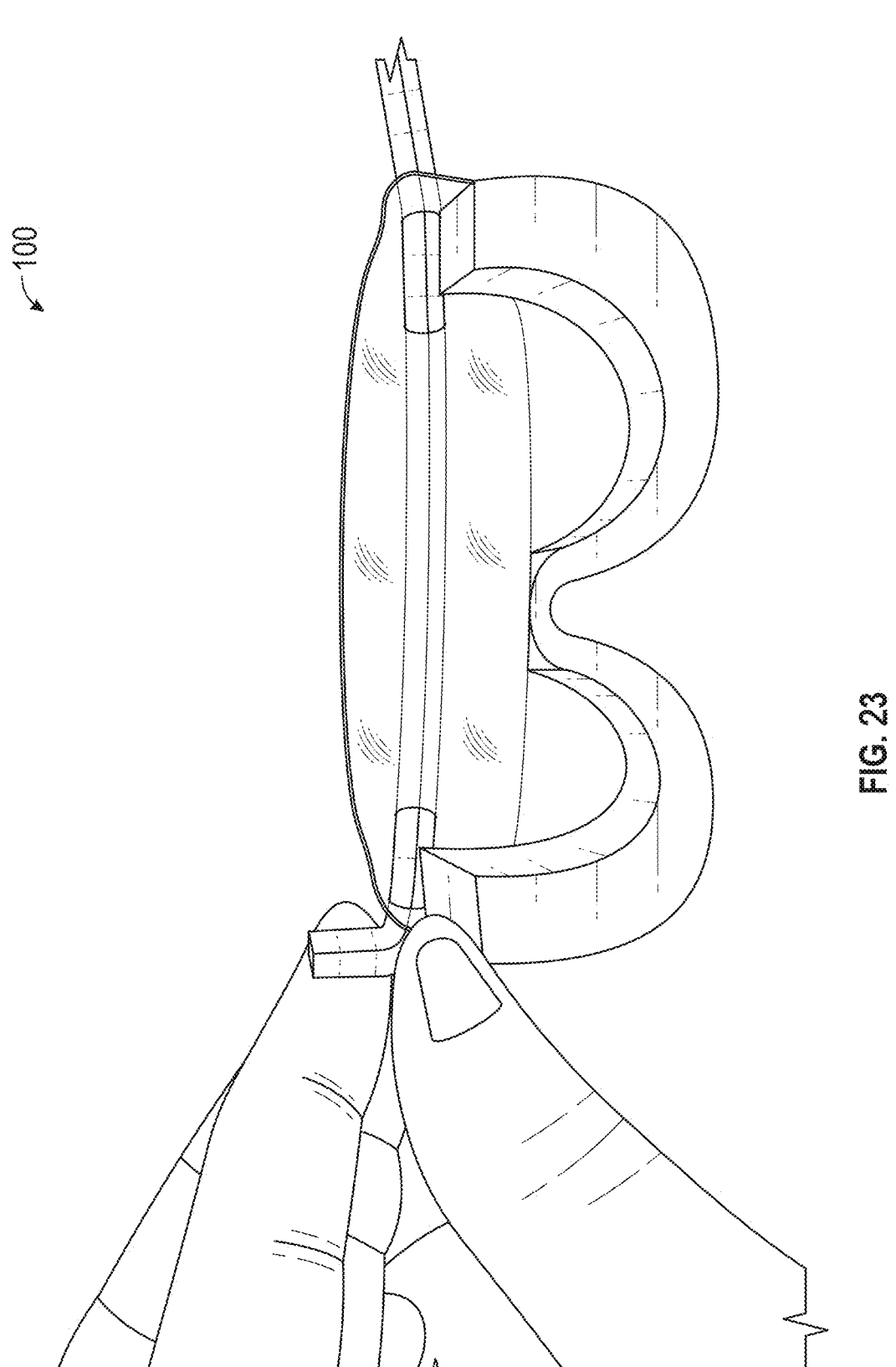
Figure 24:
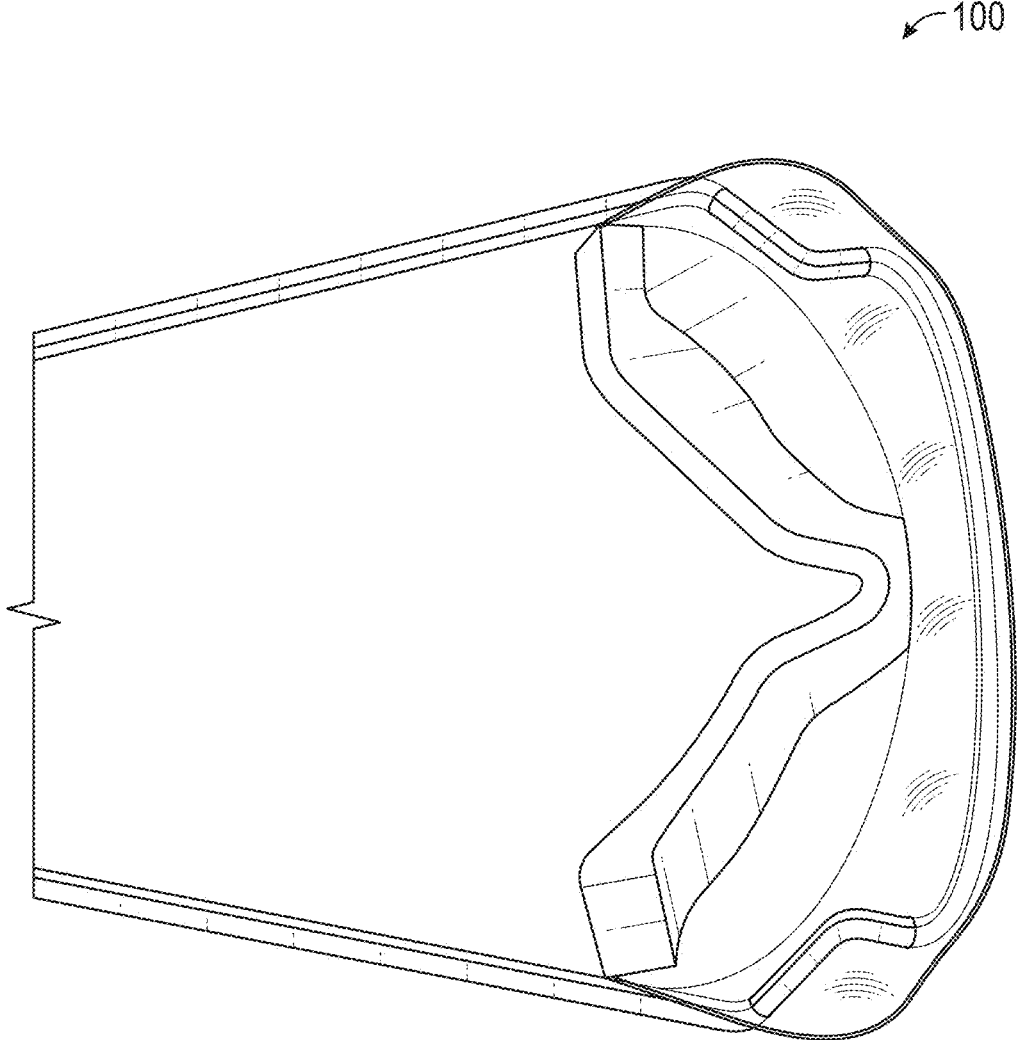
Figure 26:
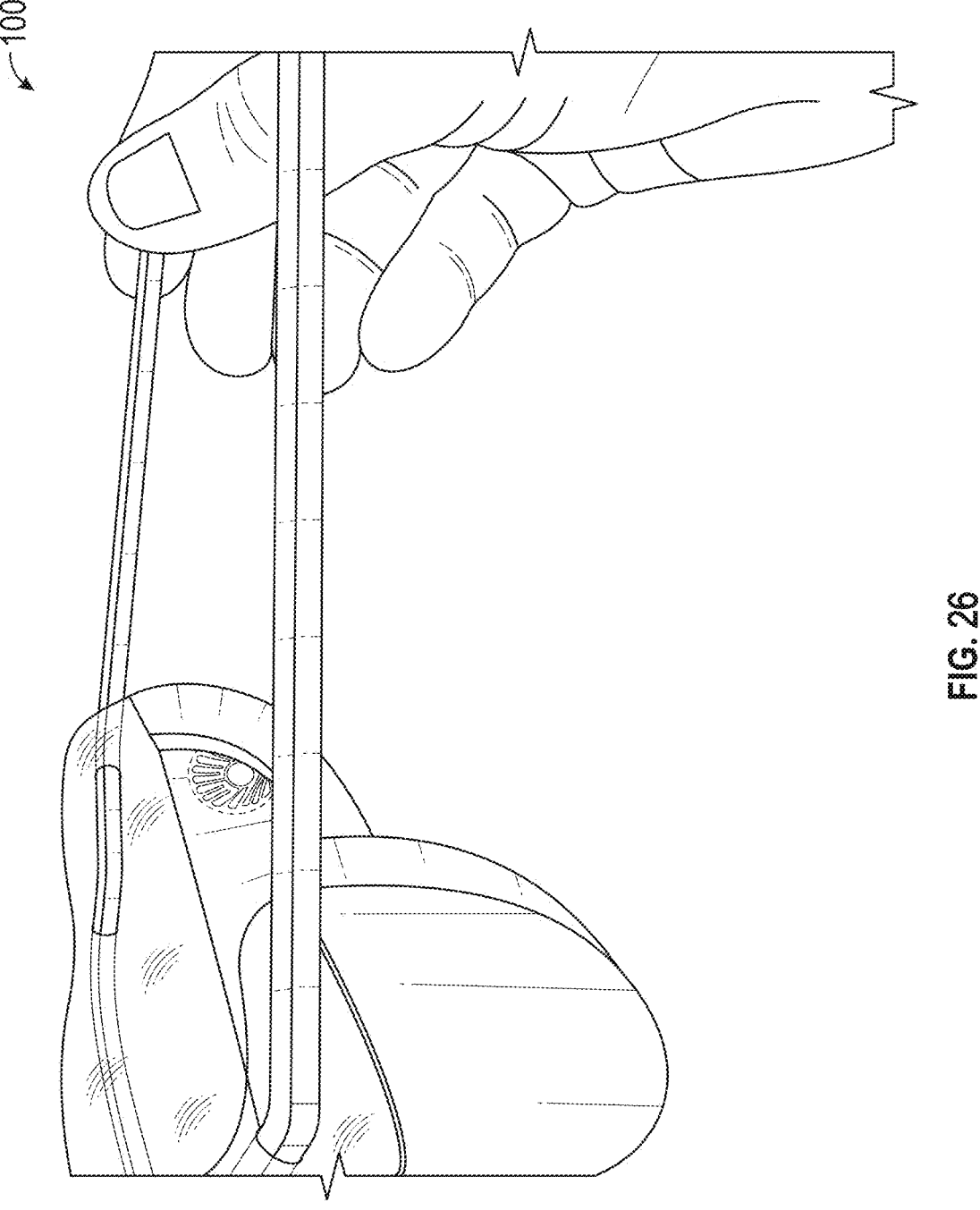
Figure 27:
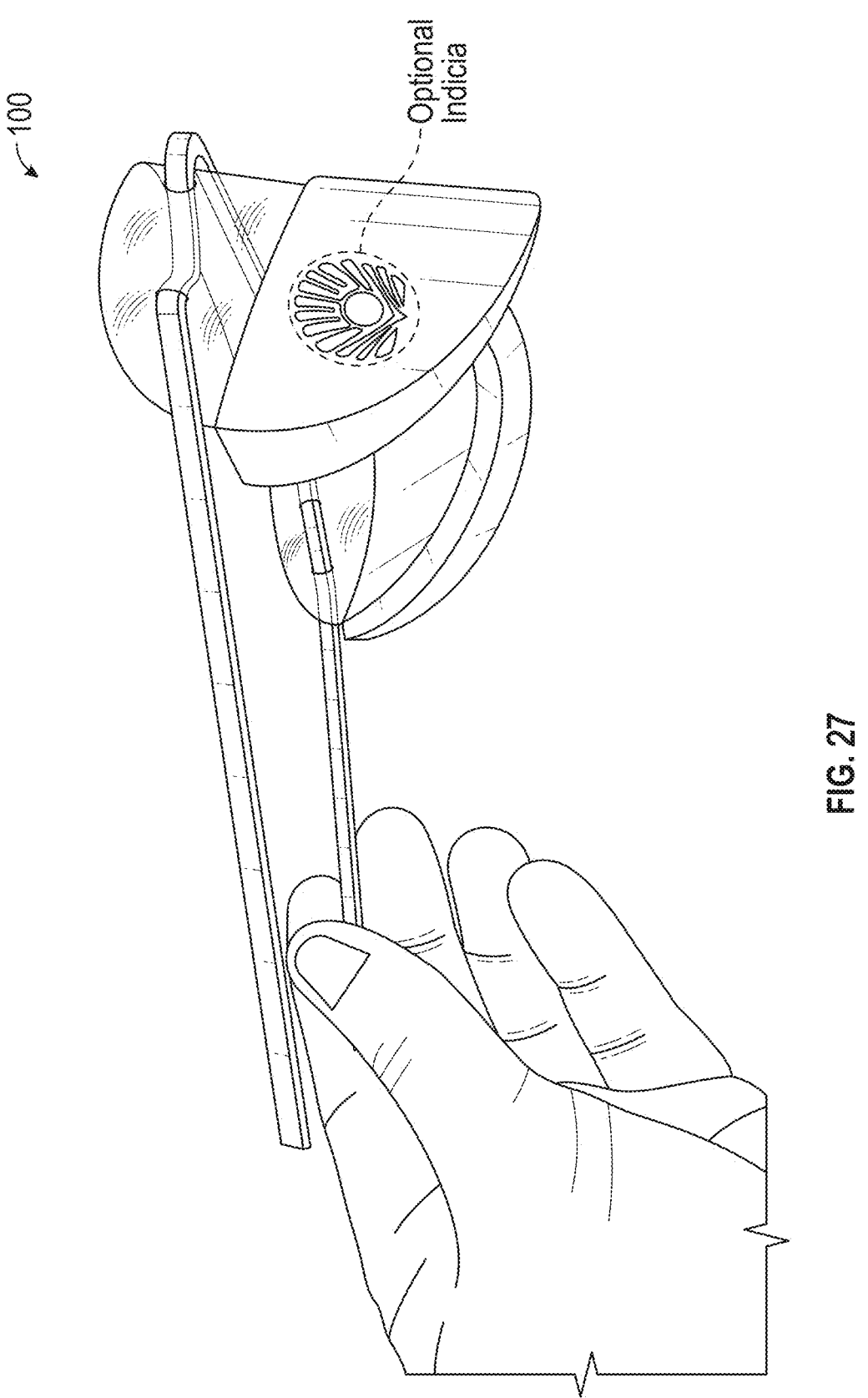

FIGS. 21A-B to 27

As mentioned, the particular form factor, components, and arrangement of an eyewear 100 according to one or more aspects of the invention can vary widely. One particular non-limiting embodiment is shown at the various views of FIGS. 21A-B to FIG. 27. These views show the embodiment in two perspective views (FIGS. 21A-B) and in isometric views of FIG. 21A (see FIGS. 22-27).

Form factor of frame, eye shield, and gapblocking interface along the lower eyeshield edge have a specific aesthetic appearance, including shapes and proportions, to make the overall appearance aesthetically pleasing.

Optionally, the embodiment can include indicia. Non-limiting examples of such indicia can be text, graphics, or both. For instance, the indicia could provide instructions of use. Alternatively, or in addition, such indicia could be a source indicator of the manufacturer such as trademark term or terms, logos, or color combination. Alternatively, the source indicating indicia could be of a customer of the manufacturer; for example, a hospital or medical clinic of clinicians that use the technical solution of the present disclosure with their patients.

Figure 28B:
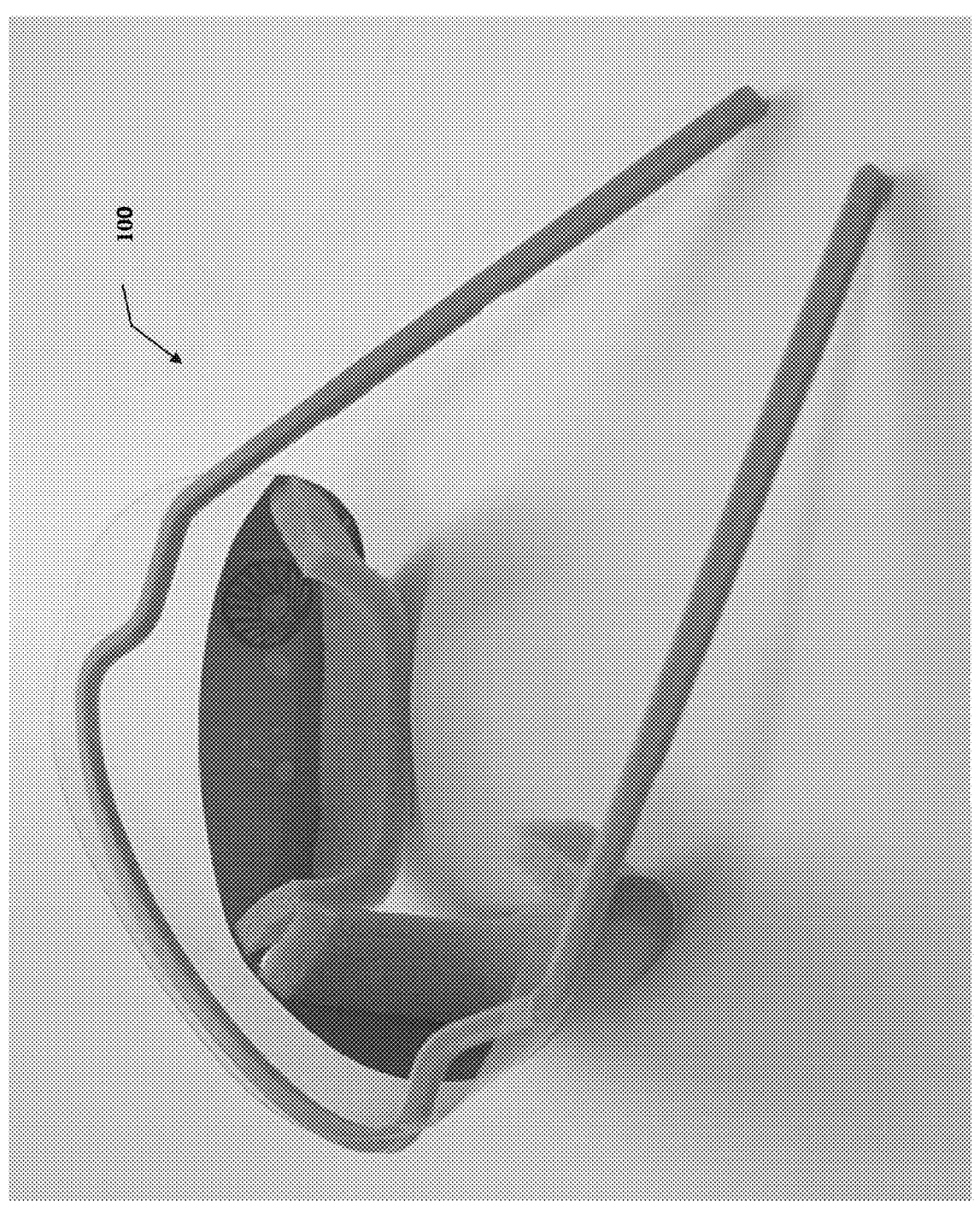
Figure 29:
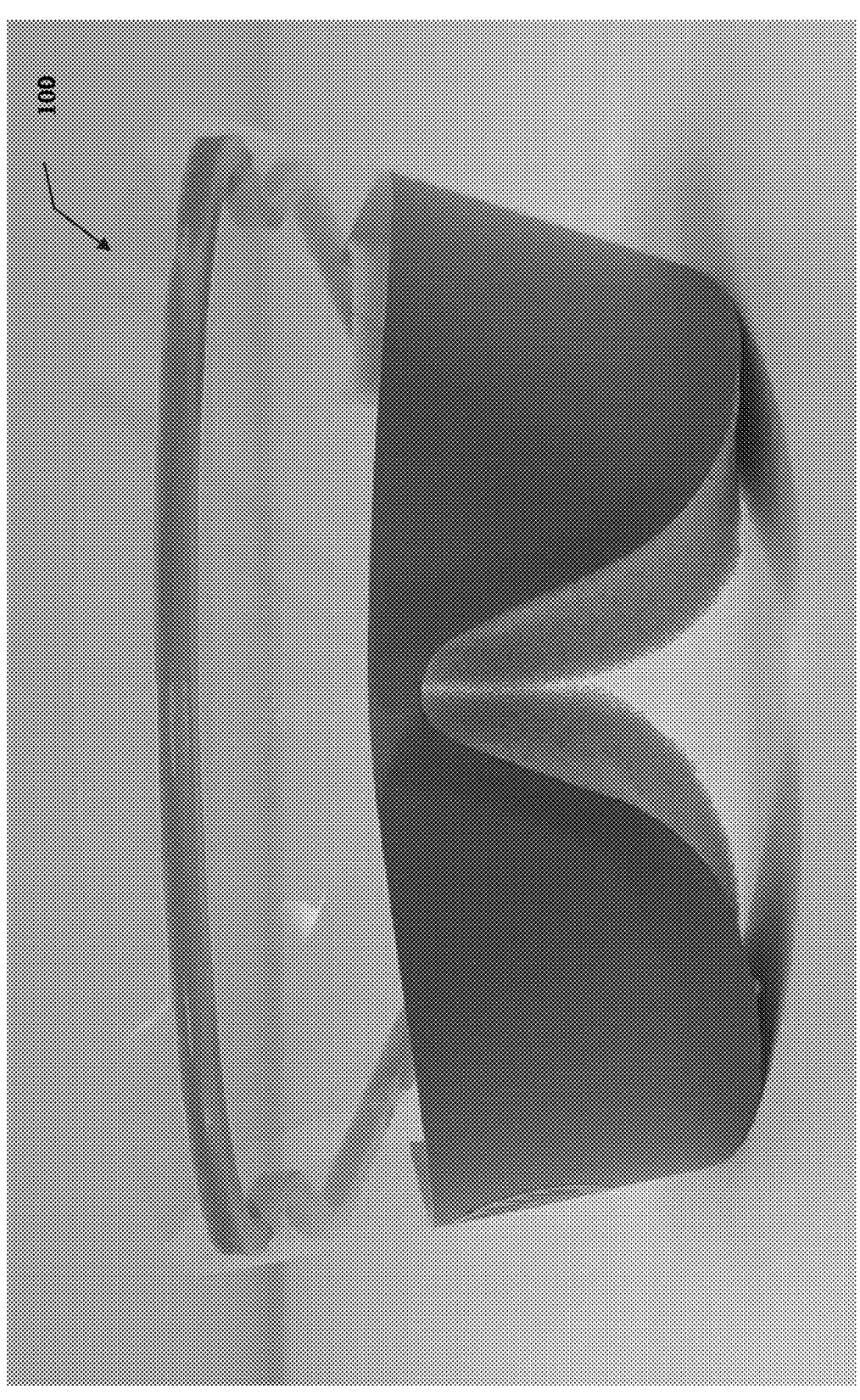
Figure 30:
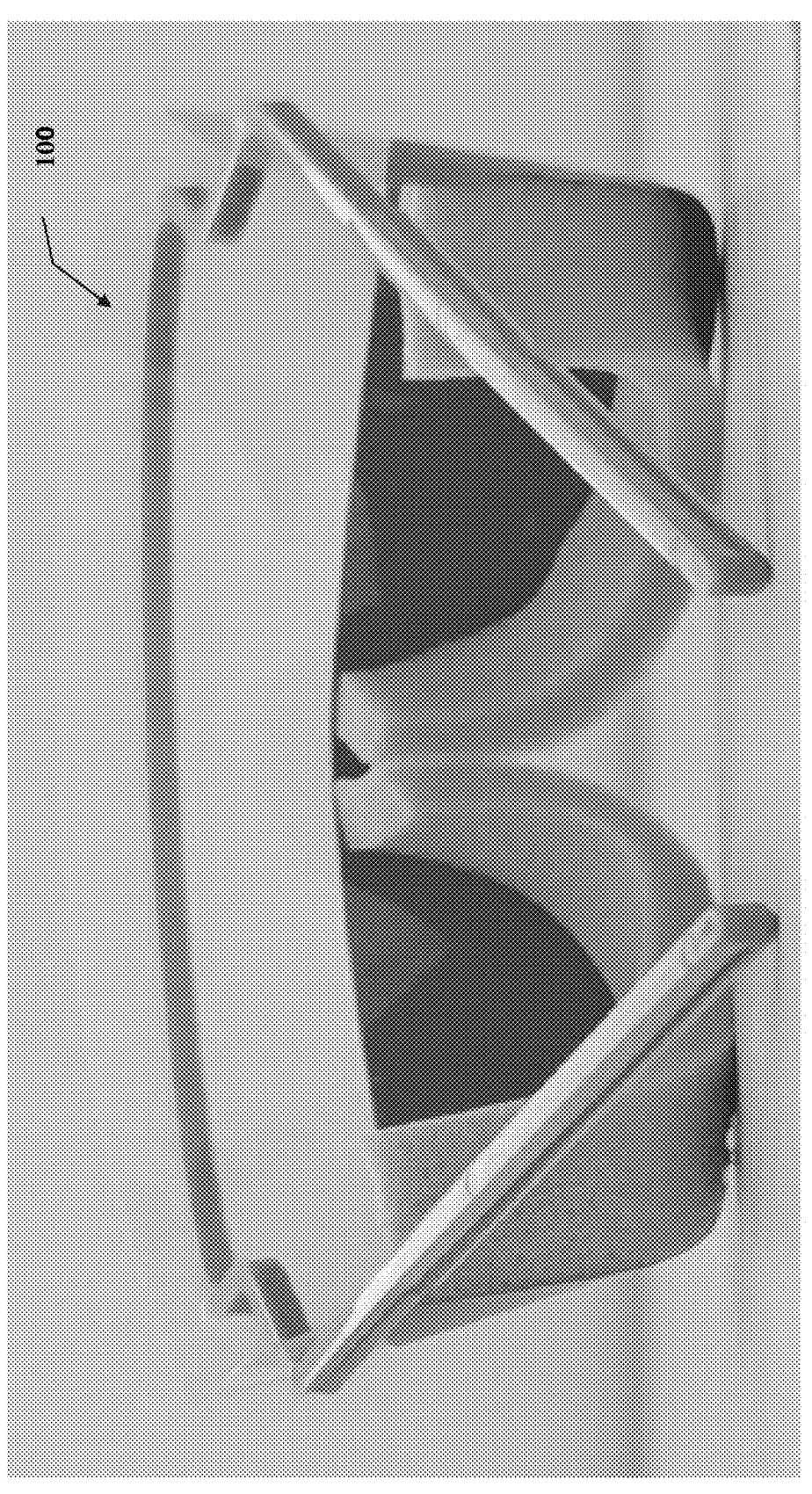
Figure 31:
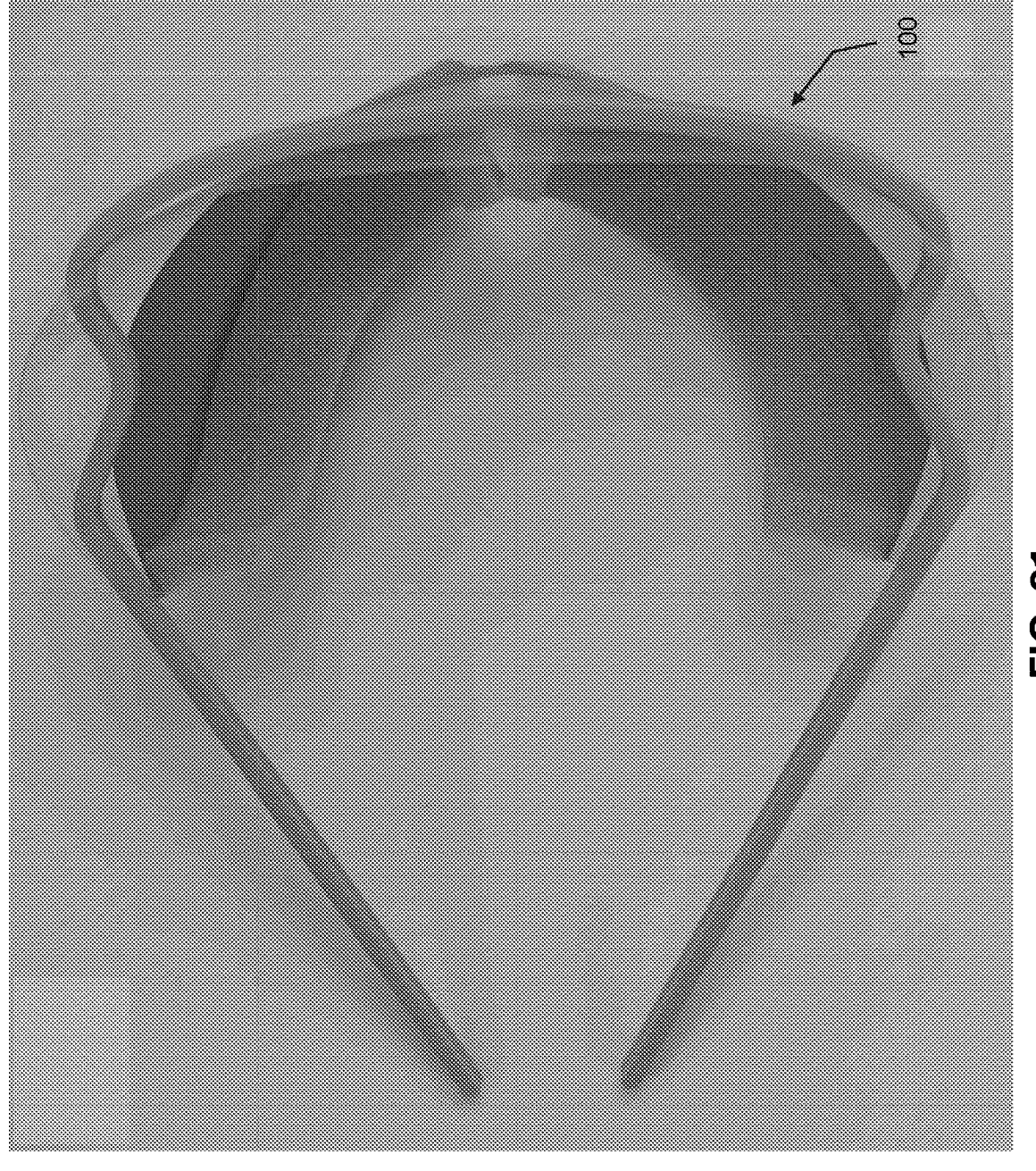
Figure 32:
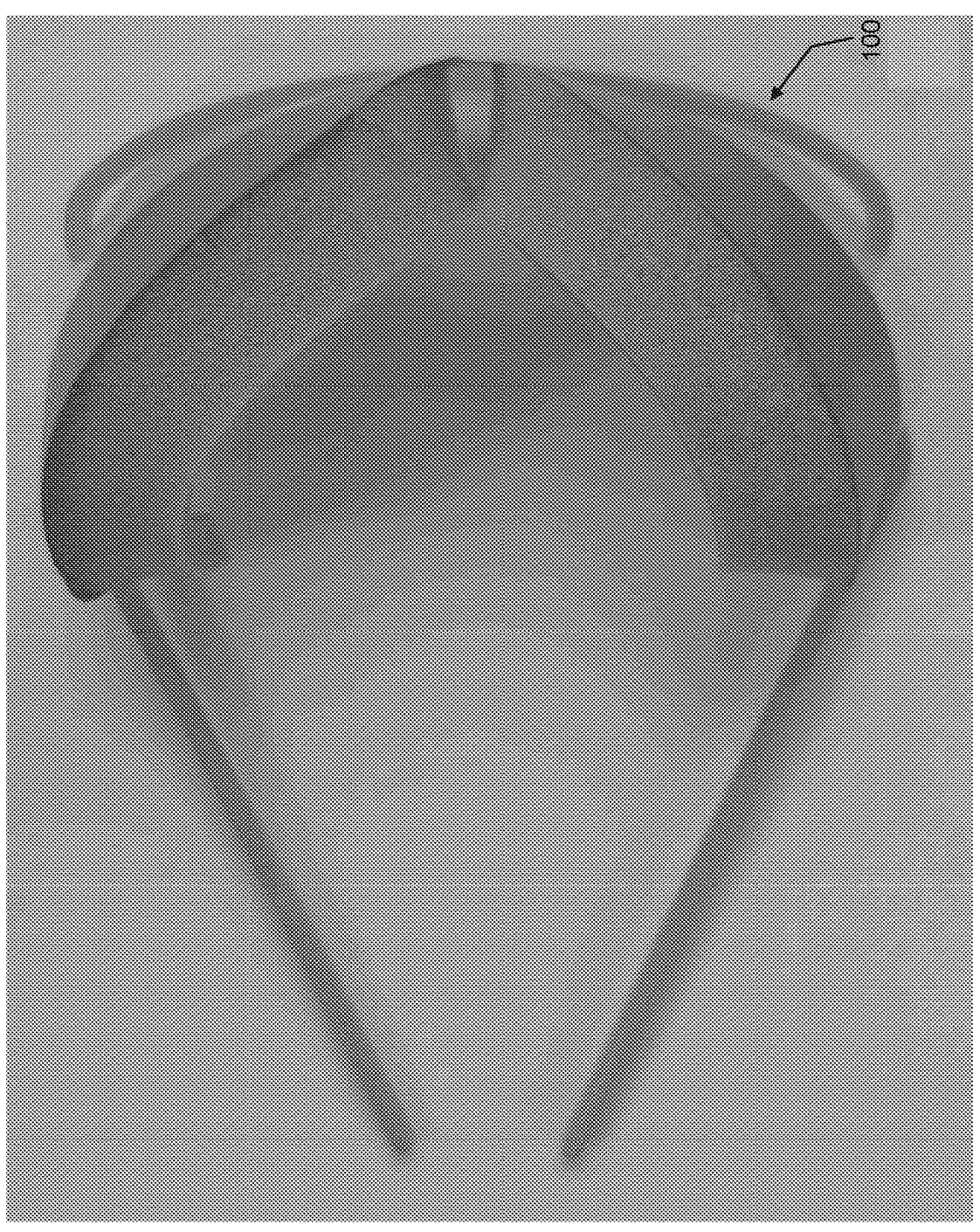
Figure 33:
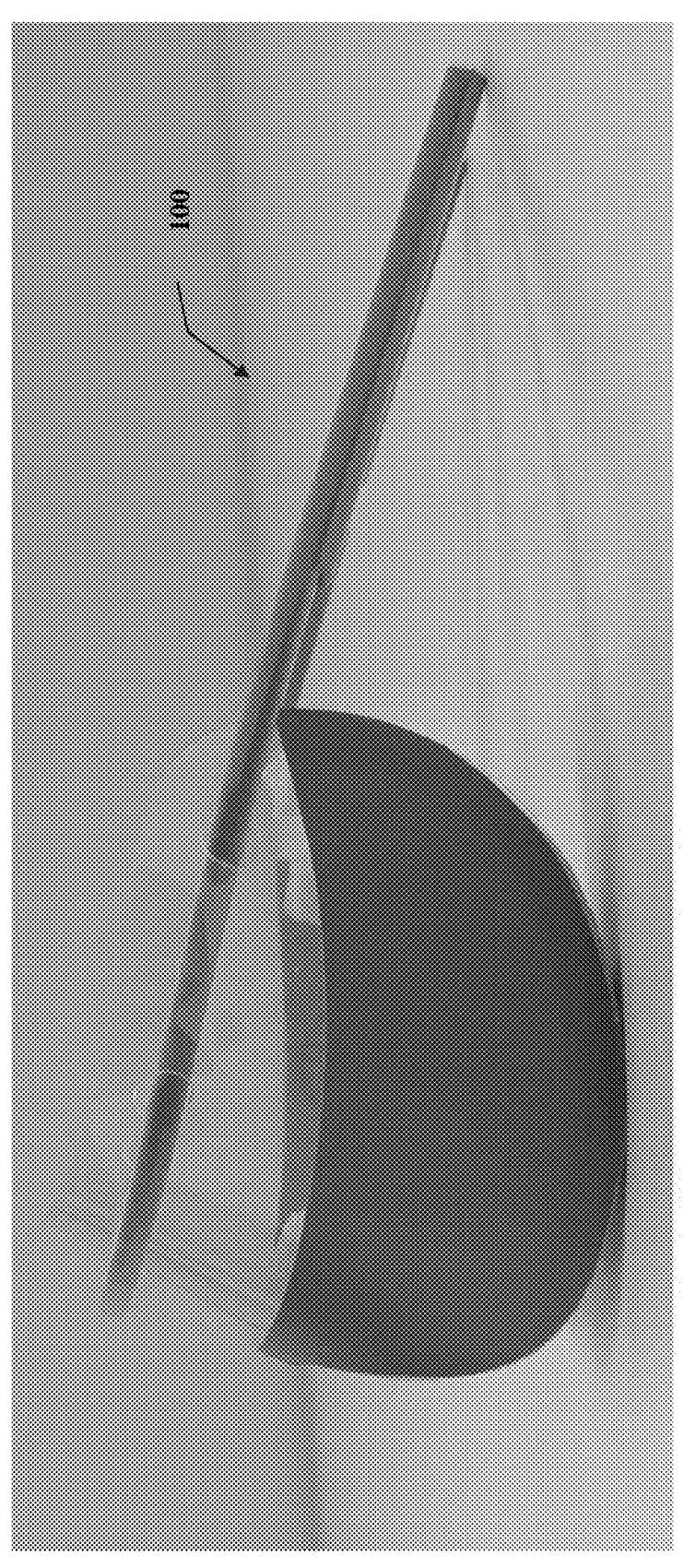
Figure 34:
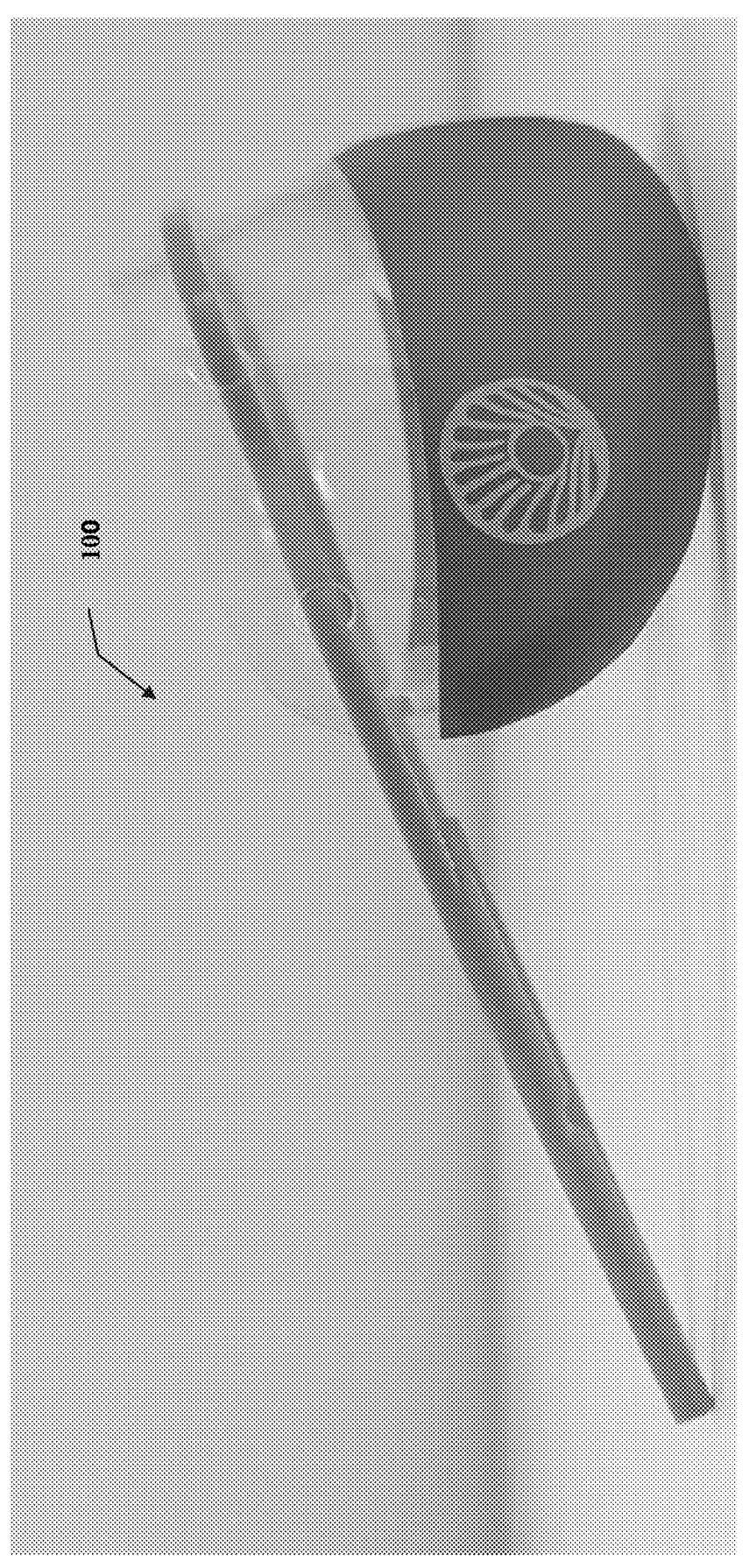

FIGS. 28A-B to 34

FIGS. 28A-B to FIG. 34 are pictures of a similar embodiment to FIGS. 21A-B to 27. They illustrate that color or color combinations can also be designed into the eyewear as another aesthetic feature, here the color pink.

FIGS. 35A-E

These illustrations can be referred to in conjunction with the other figures and descriptions in this disclosure to assist the reader in understanding one non-limiting way to make eyewear 100 according to one or more aspects of the present disclosure.

These figures illustrate that the frame could be made of a length of relatively small diameter lightweight, plastic rod pre-shaped as shown to have two opposite over-the-ear, temple-hugging portions and a front crossing portion.

An eyeshield can be made of clear plastic with a set of apertures punched or otherwise formed along near the top.

Figure 35A:
Figure 35B:

A vision blocking sheet or film material can be cut from bulk material and strategically added to the bottom of the eyeshield (FIG. 35A).

Gap-blocking interface material (e.g., foam) can be added to the user-facing side along the bottom of the eye shield. A jig (FIG. 35B) could be used with pegs matching a flat eyeshield to hold the eyeshield in place while adhering the foam to it.

Figure 35C:
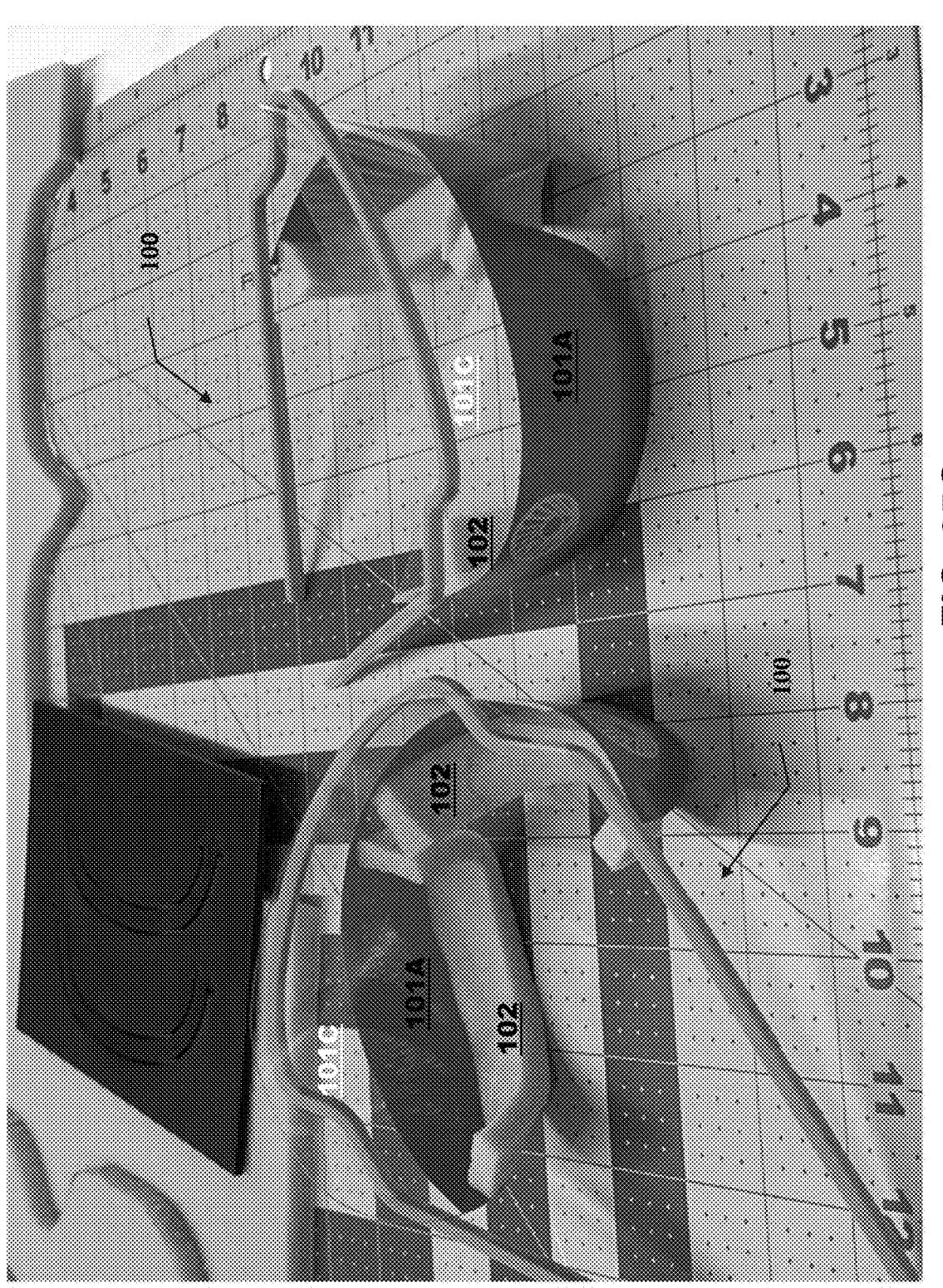
Figure 35D:
Figure 35E:

The form factor of the pre-bent frame with the spacing of the apertures in the eyeshield cooperate such that when each side of the frame is threaded through a pair of the apertures as shown, the eyeshield is held in a curved shape (FIGS. 35C-E). The subtle bends at the temple positions on opposite sides of the frame assist in deterring the eyeshield from moving or backing out of the apertures.

Thus, the completed eyewear has a frame that is rigid enough to hold the eyeshield in curved shape but has enough flexibility to splay the free ends of the temple portions if needed when installing on a person's head.

The eye shield is of economical, thin, light weight, non-optical grade transparent plastic having enough rigidity and robustness to hold its curved position on the frame and support both the vision blocking film and the gap blocking foam, and any adhesive used to fix those in place. Collectively, the eyewear is robust enough for at least one time use but is economical enough to be disposable. And the components can be manufactured by mass and economical production.

What is claimed is:

1. A method for conducting a vascular access or interventional procedure, the method comprising:

applying a vision-restricting apparatus to a subject, wherein the apparatus is applied in the form of eyewear, the apparatus being configured and positioned to obstruct the subject's lower field of vision while preserving at least partial forward or upward visibility; and performing the vascular access or interventional procedure while the apparatus remains in place.

2. The method of claim 1 wherein the apparatus is positioned at the subject's face.

3. The method of claim 1 wherein the apparatus is applied in a way that preserves ambient visual awareness through an unobstructed upper visual field.

4. The method of claim 1 wherein the apparatus is applied to provide a lower visual field blockage that appears gapless and continuous such that no form can be visually discerned beyond the obstruction of the subject's lower field of vision.

5. The method of claim 4 wherein the apparatus is positioned to fully block the subject's visual field from 45 degrees to 90 degrees inferior to a horizontal meridian based on prior perimetry mapping.

6. The method of claim 4 wherein the apparatus includes a lens, lenses, or eyeshield that, when positioned on a subject, provide a region between 45 degrees superior and 45 degrees inferior from the apparatus that includes partial or complete opaque coverage that provides the lower visual field blockage.

7. The method of claim 4 wherein the apparatus is positioned such that the subject's visual field above 45 degrees superior remains fully unobstructed by the lower visual field blockage.

8. The method of claim 4 wherein the apparatus includes a conformable interface along a bottom of a front and sides of a lower visual field blockage structure configured to provide the lower visual field blockage of the eyewear that, when applied to a face of the subject, forms a continuous visual barrier between the apparatus and the subject's face by extending laterally and vertically along the subject's face.

9. The method of claim 8 wherein the conformable interface comprises one or more foam segments that fold, rotate, or bend against themselves when compressed, thereby assisting in elimination of gaps between the one or more foam segments and one or more adjacent facial surfaces comprising a nasal bridge, cheeks, or temples.

10. The method of claim 8 wherein the conformable interface comprises one or more foam segments and is applied to the subject's face in a manner that allows it to fold inward toward an interior-facing surface of the lower visual field blockage structure, such that the one or more foam segments collapse in a direction extending from a facial surface of the subject toward the lower visual field blockage structure, wherein the facial surface comprises one or more of a nose bridge, cheek regions, or temple regions of the subject.

11. The method of claim 1 wherein the apparatus includes an adhesive-backed interface that, when applied to the subject's face, assists in maintaining continuous contact of the apparatus with the subject's face.

12. The method of claim 1 wherein the apparatus is worn during the vascular access or interventional procedure, wherein the vascular access or interventional procedure comprises a breast biopsy procedure performed under ultrasound guidance or stereotactic imaging.

13. The method of claim 1 wherein the apparatus is applied prior to the vascular access or interventional procedure, wherein the vascular access or interventional procedure comprises a needle-based procedure, wherein the needle-based procedure is one of venipuncture, intravenous placement, blood draw, plasma donation, or soft-tissue biopsy.

14. The method of claim 1 wherein the apparatus is applied in a way that accommodates anatomical variation across different nose bridge profiles without compromising the obstruction of the subject's lower field of vision.

15. The method of claim 1 wherein the procedure includes preoperative wire localization for non-palpable breast lesions, wherein a wire is inserted into a breast of the subject prior to surgery to guide a surgeon to a lesion site.

16. The method of claim 1 wherein the apparatus is applied as a single-use disposable device.

17. The method of claim 1 wherein the application of the apparatus is configured to reduce physiological or psychological distress associated with procedural visual triggers including one or more of vasovagal response, dizziness, or emotional discomfort.

18. A method according to claim 1 for reducing visual triggers during the vascular access or interventional procedure on the subject having a face, nasal bridge, cheeks, and temples wherein the vision-restricting apparatus comprises:
    a. an opaque or effectively vision blocking lower region comprising:
        i. a flexible lens, lenses, eyeshield, or vision block made of a polymeric material, the lens, lenses, eyeshield, or vision block being optically non-transmissive such that no discernible form is visible through it; and
        ii. a face-conformable interface along a lower portion of the lens, lenses, eyeshield, or vision block, the interface configured to fold inward or bend against itself when compressed, thereby promoting a continuous, gapless visual barrier along the nasal bridge, cheeks, and temples when installed on the subject's face;
        wherein the vision blocking lower region is configured to obstruct visual input from a top boundary located between 0 degrees and 45 degrees inferior to a horizontal meridian, the obstruction extending downward to between 45 and 90 degrees inferior;
    b. an upper region above a top boundary of the vision blocking lower region which is free of vision obstruction to preserve forward or upward visual awareness of the subject.

19. A method for conducting a vascular access or interventional procedure, the method comprising:
    applying a vision-restricting apparatus to a subject, the apparatus being configured and positioned to obstruct the subject's lower field of vision while preserving at least partial forward or upward visibility; and
    performing the vascular access or interventional procedure while the apparatus remains in place, wherein the apparatus is worn during an interventional procedure comprising a breast biopsy procedure performed under ultrasound guidance or stereotactic imaging.

20. The method of claim 19 wherein the procedure further includes preoperative wire localization for non-palpable breast lesions, wherein a wire is inserted into a breast of the subject prior to surgery to guide a surgeon to a lesion site.

21. A method for conducting a vascular access or interventional procedure, the method comprising:
    applying a vision-restricting apparatus to a subject, the apparatus being configured and positioned to obstruct the subject's lower field of vision while preserving at least partial forward or upward visibility, wherein the apparatus is applied to provide a lower visual field blockage that appears gapless and continuous such that no form can be visually discerned beyond the obstruction of the subject's lower field of vision, wherein the apparatus is applied with a conformable interface that forms a continuous, gapless visual barrier extending laterally and vertically along the subject's face; and
    performing the vascular access or interventional procedure while the apparatus remains in place.

22. The method of claim 21 wherein, to assist the gapless and continuous lower field visual blockage, the conformable interface comprises one or more foam segments that fold, rotate, or bend against themselves when compressed, thereby assisting in an elimination of gaps between the one or more foam segments and adjacent facial surfaces comprising one or more of a nasal bridge, cheeks, or temples.

23. The method of claim 21 wherein the apparatus includes a lens, lenses, or eyeshield and the conformable interface comprises one or more foam segments and is applied in a manner that allows it to fold inward toward an interior-facing surface of the lens, lenses, or eyeshield such that the one or more foam segments collapse in a direction extending from a facial surface of the subject's face toward the lens, lenses, or eyeshield, including at one or more of a nasal bridge, cheek regions, or temple regions of the subject's face.

24. The method of claim 21 wherein the apparatus is positioned such that a region of the apparatus between 45 degrees superior and 45 degrees inferior includes partial or complete opaque lens, lenses, or eyeshield coverage.

25. A method for reducing visual triggers during a vascular access or interventional procedure on a subject having a face, nasal bridge, cheeks, and temples, the method comprising:

applying a vision-restricting apparatus to a subject, the apparatus being configured and positioned to obstruct the subject's lower field of vision while preserving at least partial forward or upward visibility, wherein the vision-restricting apparatus comprises:

a. an opaque or effectively vision blocking lower region comprising:

b. a flexible lens, lenses, eyeshield, or vision block made of a polymeric material, the lens, lenses, eyeshield, or vision block being optically non-transmissive such that no discernible form is visible through it; and c. a face-conformable interface along a lower portion of the lens, lenses, eyeshield, or vision block, the interface configured to fold inward or bend against itself when compressed, thereby promoting a continuous, gapless visual barrier along one or more of the nasal bridge, cheeks, and temples when installed on the subject's face;

wherein the vision blocking lower region is configured to obstruct visual input from a top boundary located between 0 degrees and 45 degrees inferior to a horizontal meridian, the obstruction extending downward to between 45 and 90 degrees inferior;

wherein an upper region above a top boundary of the vision blocking lower region is free of vision obstruction to preserve forward or upward visual awareness of the subject; and performing the vascular access or interventional procedure while the apparatus remains in place on the subject.

* * * * *